(12) United States Patent
Li et al.

(10) Patent No.: US 8,716,237 B2
(45) Date of Patent: May 6, 2014

(54) METHODS FOR THE TREATMENT OR PREVENTION OF HEMORRHAGIC CONDITIONS

(75) Inventors: Jian-Dong Li, Pittsford, NY (US); Jae Hyang Lim, Rochester, NY (US)

(73) Assignee: University of Rochester, Rochester, NY (US)

( * ) Notice: Subject to any disclaimer, the term of this patent is extended or adjusted under 35 U.S.C. 154(b) by 273 days.

(21) Appl. No.: 12/670,778

(22) PCT Filed: Jul. 22, 2008

(86) PCT No.: PCT/US2008/070731
§ 371 (c)(1),
(2), (4) Date: May 11, 2010

(87) PCT Pub. No.: WO2009/018010
PCT Pub. Date: Feb. 5, 2009

(65) Prior Publication Data
US 2010/0215668 A1    Aug. 26, 2010

Related U.S. Application Data

(60) Provisional application No. 60/953,289, filed on Aug. 1, 2007.

(51) Int. Cl.
*A61K 38/36*  (2006.01)
*A61K 38/55*  (2006.01)
*A61K 38/16*  (2006.01)

(52) U.S. Cl.
USPC ................. 514/20.3; 514/13.7; 514/21.2

(58) Field of Classification Search
None
See application file for complete search history.

(56) References Cited

U.S. PATENT DOCUMENTS

| | | | |
|---|---|---|---|
| 2003/0082532 | A1 | 5/2003 | Ni et al. |
| 2004/0022740 | A1* | 2/2004 | Baker et al. .................. 424/45 |
| 2004/0229315 | A1* | 11/2004 | Lee et al. .................. 435/69.1 |
| 2005/0042227 | A1 | 2/2005 | Zankel et al. |
| 2006/0030531 | A1 | 2/2006 | Rojkjaer |
| 2006/0089305 | A1 | 4/2006 | Rest et al. |
| 2006/0292119 | A1 | 12/2006 | Chen et al. |
| 2007/0224663 | A1* | 9/2007 | Rosen et al. .................. 435/69.1 |

OTHER PUBLICATIONS

Olomu et al. "Treatment of severe pulmonary hemorrhage with activated recombinant Factor VII (rFVIIa) in very low birth weight" J Perinatology, 2002, 22, 672-674.*
Primack et al. "Diffuse pulmonary hemorrhage: clinical, pathologic, and imaging features" AJR 1995, 164, 295-300.*
Schattauer "Challenges and innovations in the treatment of bleeding disorders" Thrombosis and Haemostasis, 2010, 104.5, pp. IX-XIV.*
Marchiori et al. "Pulmonary hemorrhage syndrome associated with dengue fever, high-resolution computed tomography findings: a case report" Orphanet J. of Rare Diseases, 4:8, 2009, pp. 1-4.*
Rubins et al. "Toxicity of pneumolysin to pulmonary endothelia cells in vitro" Infection and Immunity, 60(5), May 1992, 1740-1746.*
Yanagihara et al. "Effects of specific neutrophil elastase inhibitor, sivelestate sodium hydrate, in murine model of severe neumonococcal pneumonia" Experimental Lung Research, 33, 2007, 71-80.*
Biomerieux International Newsletter, "Identifying resistance" No. 5, Feb. 2005, pp. 1-6.*
Seki et al. "Immunokinetics in severe pneumonia due to influenza virus and bacteria coinfection in mice" Eur Respir J. 2004, 24(1): 143-9.*
PCT International Search Report and Written Opinion for PCT/US2008/070731 (Dec. 9, 2008).
Berkenpas et al., "Molecular Evolution of Plasminogen Activator Inhibitor-1 Functional Stability," EMBO J 14:2969-2977 (1995).
Renckens et al., "The Role of Plasminogen Activator Inhibitor Type I in the Inflammatory Response to Local Tissue Injury," J Throm Haemost 3:1018-1025 (2005).
Arndt et al., "Regulation of Lipopolysachcaride-Induced Lung Inflammation by Plasminogen Activator Inhibitor-1 Through a JNK-Mediated Pathway," J Immunol 175:4049-4059 (2005).
Lijnen, H.R., "Pleiotropic Functions of Plasminogen Activator Inhibitor-1," J Throm Haemost 3:35-45 (2005).
Johnson et al., "Fibrin-Mediated Protection Against Infection-Stimulated Immunopathology," J Exp Med 197:801-806 (2003).
Mullarky et al., "Infection-Stimulated Fibrin Deposition Controls Hemorrhage and Limits Hepatic Bacterial Growth During Listeriosis," Infect Immun 73:3888-3895 (2005).
Renckens et al., "Plasminogen Activator Inhibitor Type 1 is Protective During Severe Gram-Negative Pneumonia," Blood 109:1593-1601 (2007).
Rijneveld et al., "Plasminogen Activator Inhibitor Type-1 Deficiency Does Not Influence the Outcome of Murine Pneumococcal Pneumonia," Blood 102(3):934-939, 2003.
Schuster, D.P., "Acute Lung Injury and Predictors of Mortality," Am J Physiol Lung Cell Mol Physiol 285:L18-L19 (2003).
Kolls, J. K., "Balancing Mucosal Immunity: Caught Between CYLD and Charybdis," Immunity 27:187-189 (2007).
Lim et al., "Tumor Suppressor CYLD Acts as a Negative Regulator for Non-Typeable Haemophilus Influenza-Iduced Inflammation in the Middle Ear and Lung of Mice," PLoS One at www.plosone.org 10(e1032):1-10 (2007).
Lim et al., "Tumor Suppressor CYLD Regulates Acute Lung Injury in Lethal *Streptococcus pneumoniae* Infections," Immunity 27:349-360 (2007).

* cited by examiner

*Primary Examiner* — Daniel E Kolker
*Assistant Examiner* — James Rogers
(74) *Attorney, Agent, or Firm* — LaClairRyan, a Professional Corporation

(57) ABSTRACT

The present invention relates to a method for treatment or prevention of a hemorrhagic condition in a patient by administering plasminogen activator inhibitor-1 ("PAI-1") and/or an inhibitor of deubiquitinating enzyme CYLD ("CYLD") to a patient. Pharmaceutical compositions that include one or both of PAI-1 and an inhibitor of CYLD are also disclosed.

28 Claims, 13 Drawing Sheets

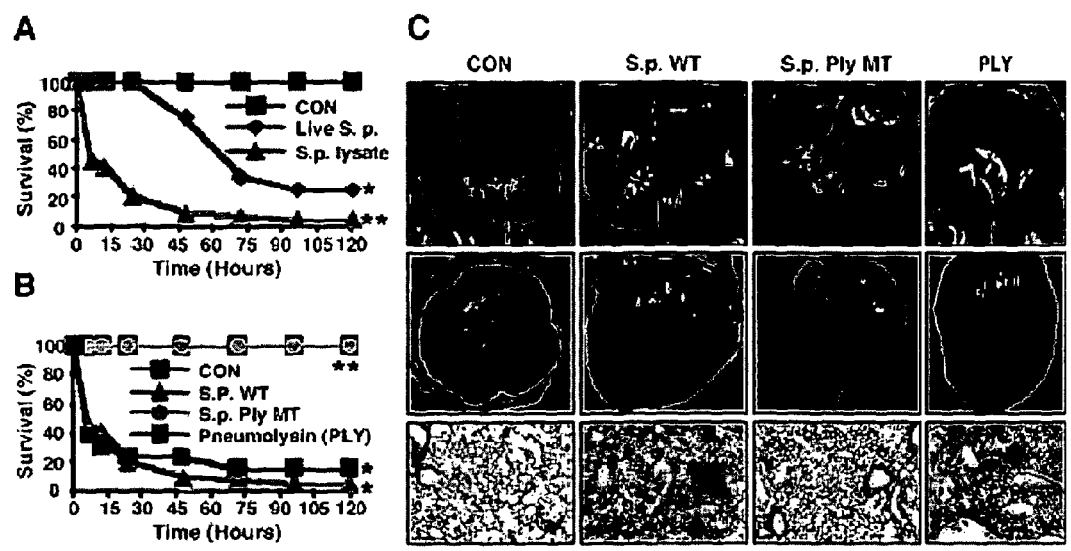
Figures 2A–C
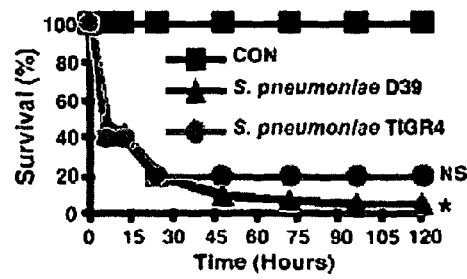
Figures 3

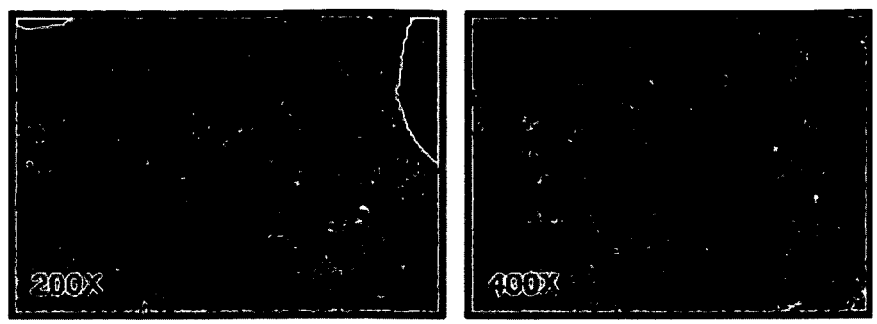
Figure 4
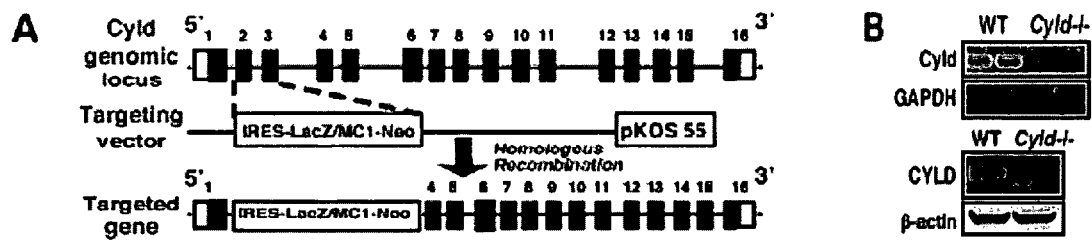
Figures 5A–B

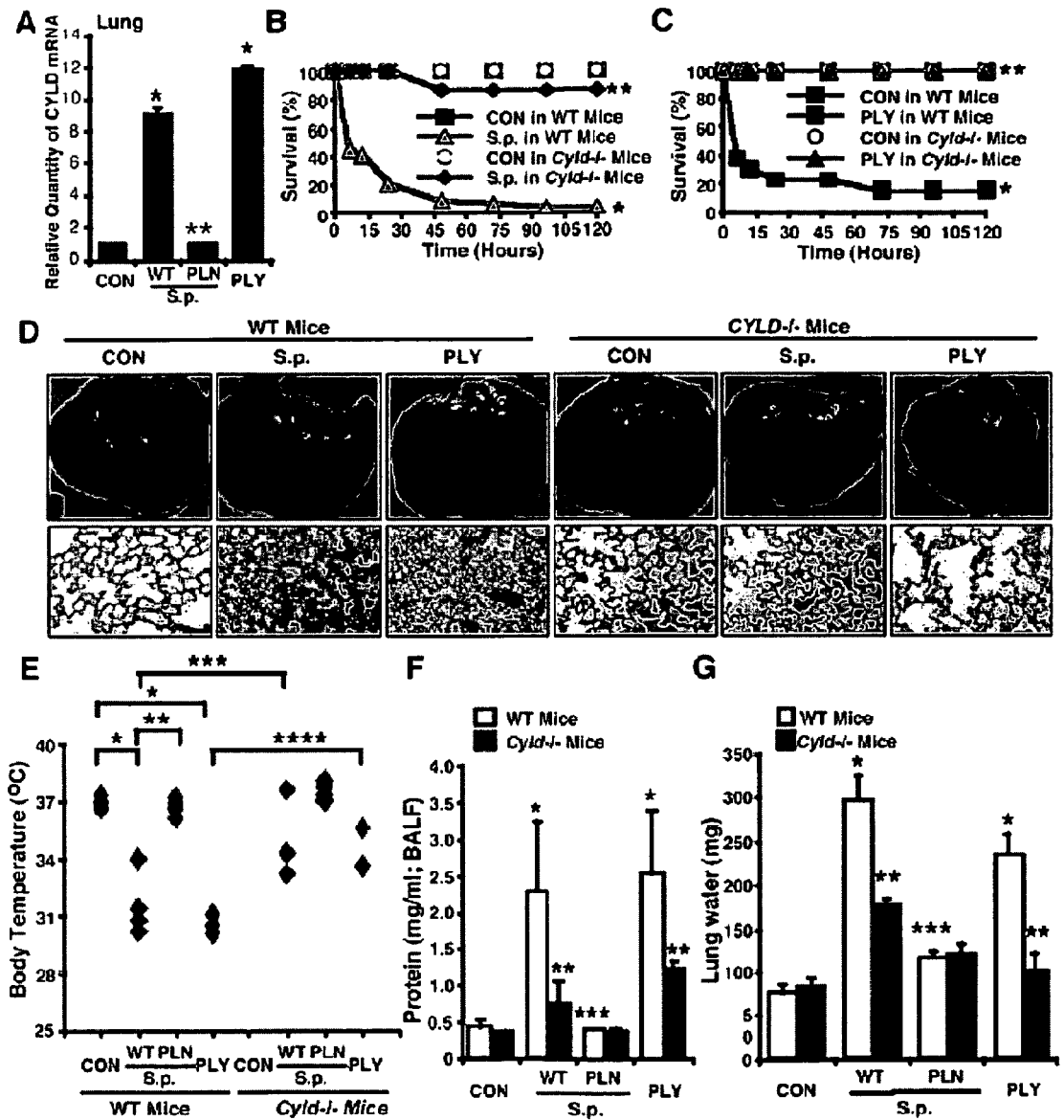
Figures 6A–G

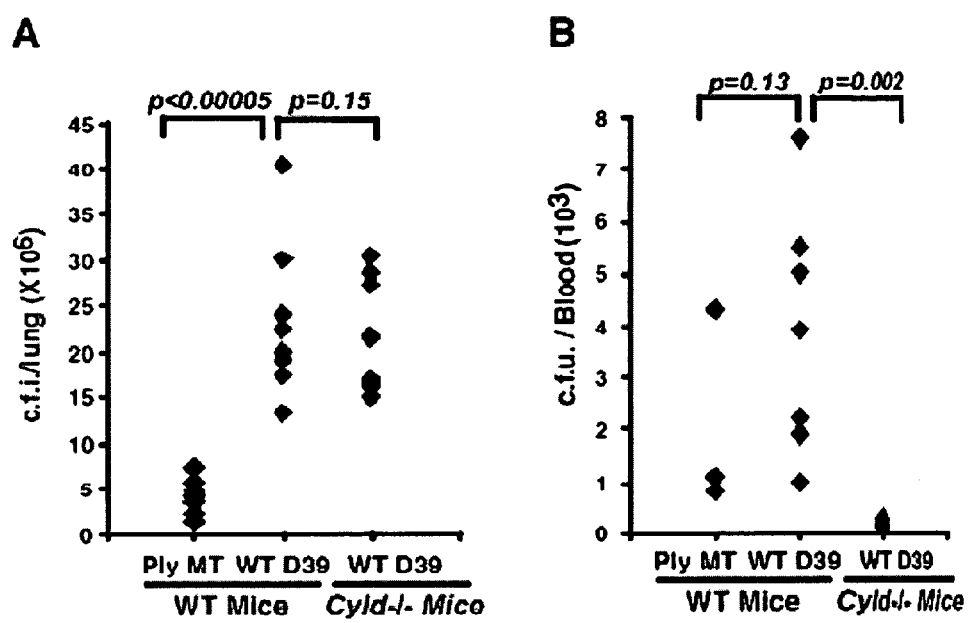
Figures 7A–B

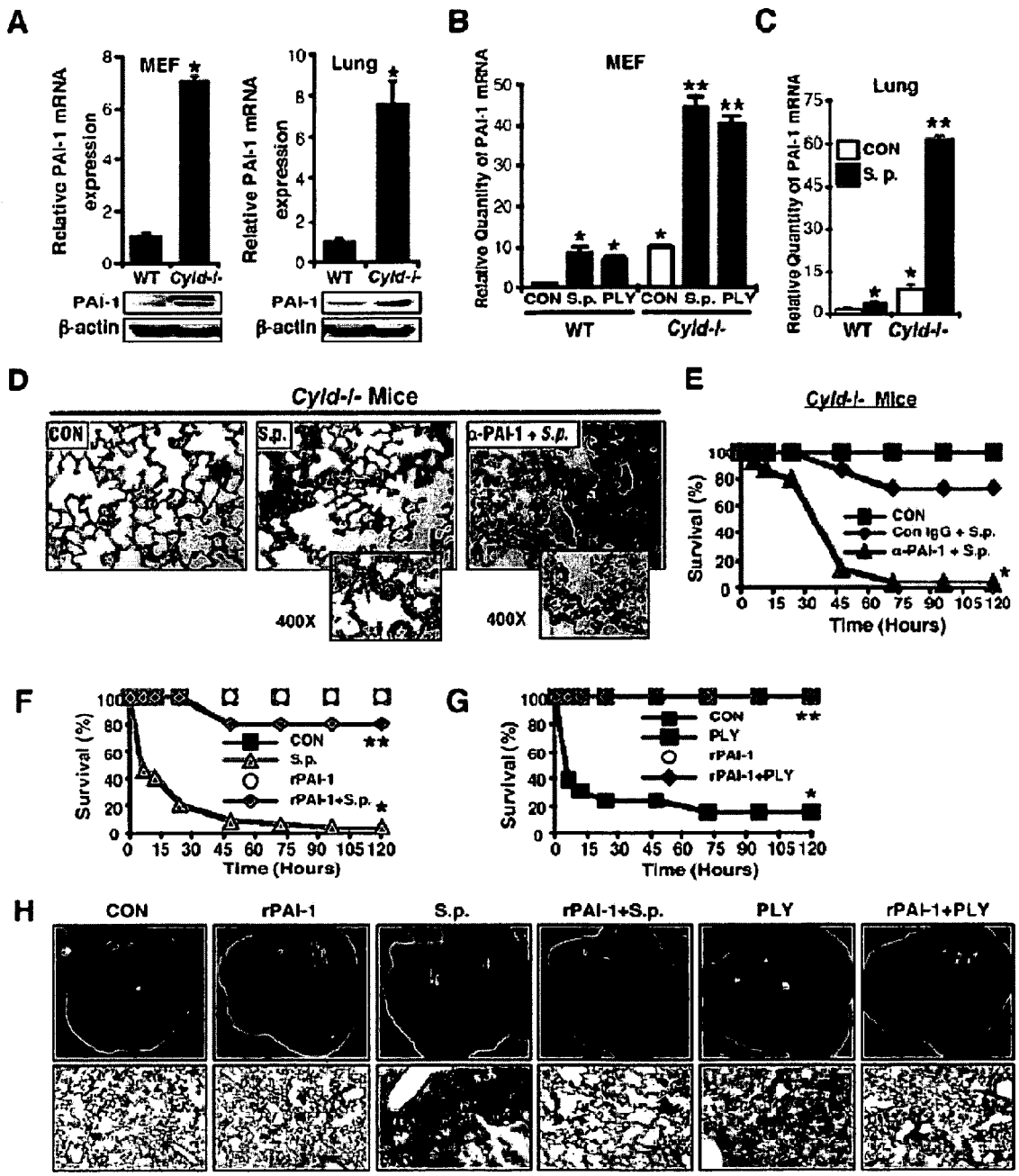
Figures 8A–H

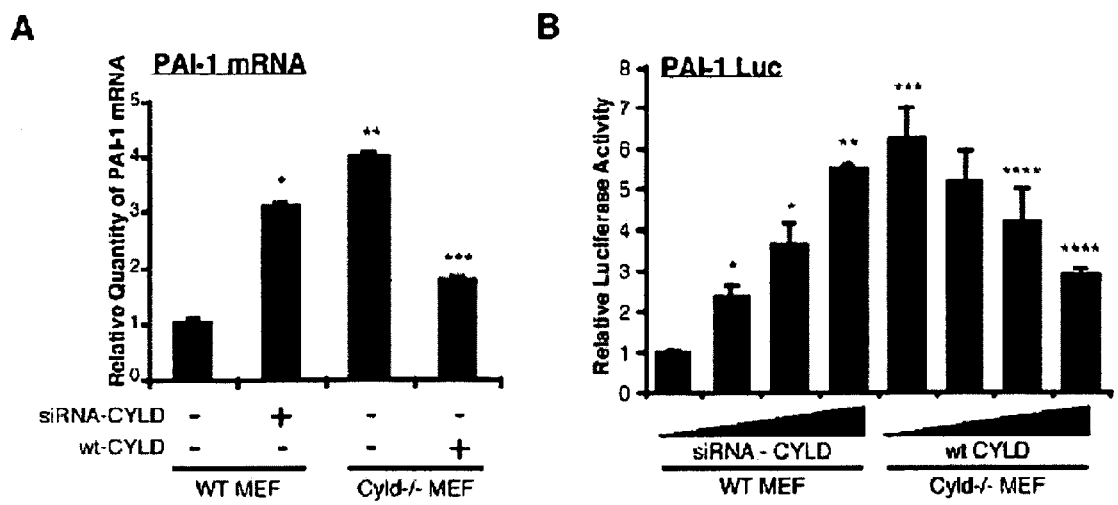
Figures 9A–B
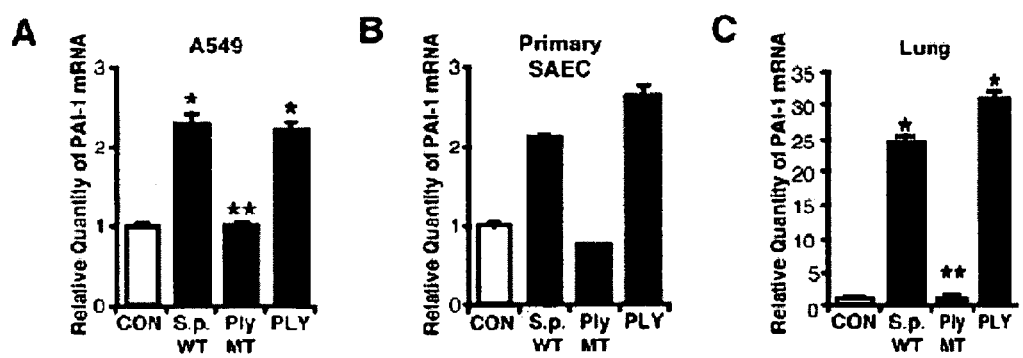
Figures 10A–C

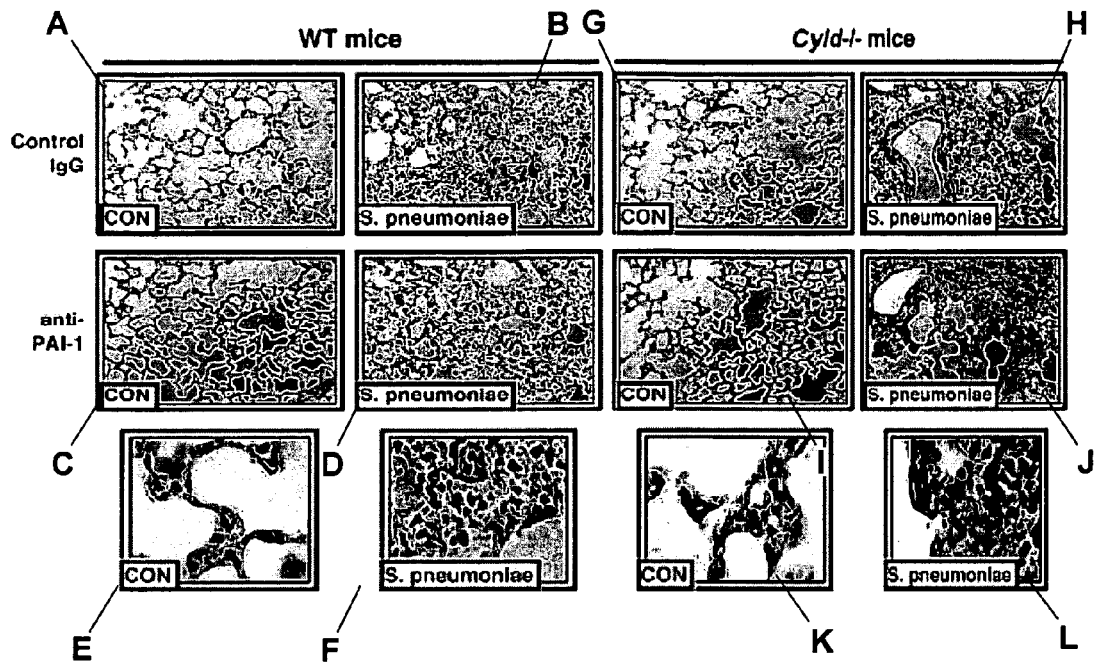
Figures 11A–L
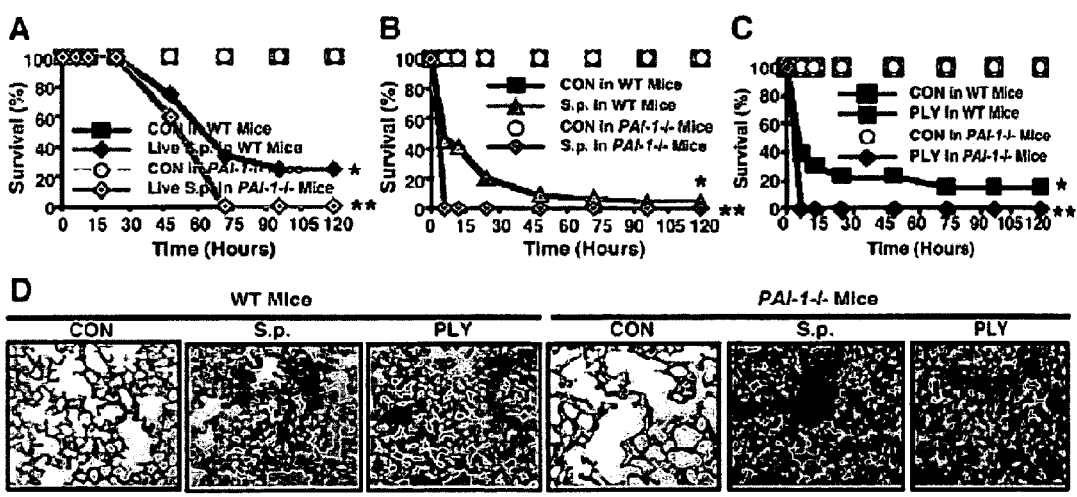
Figures 12A–D

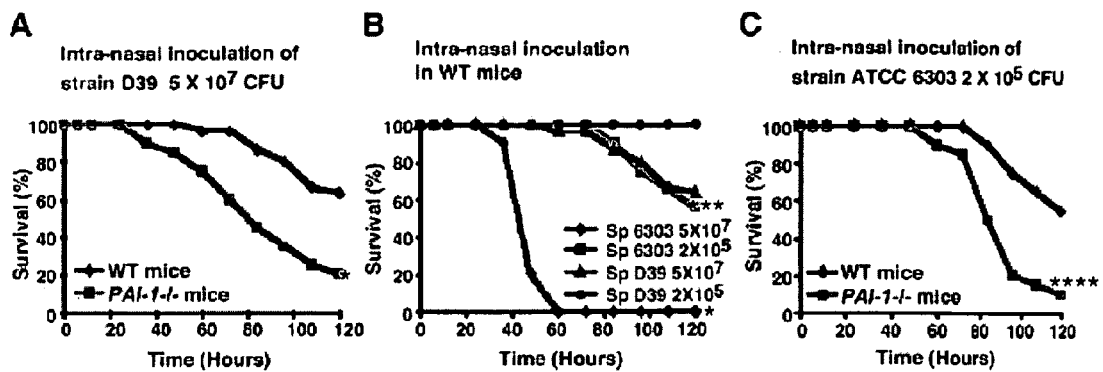
Figures 13A–C
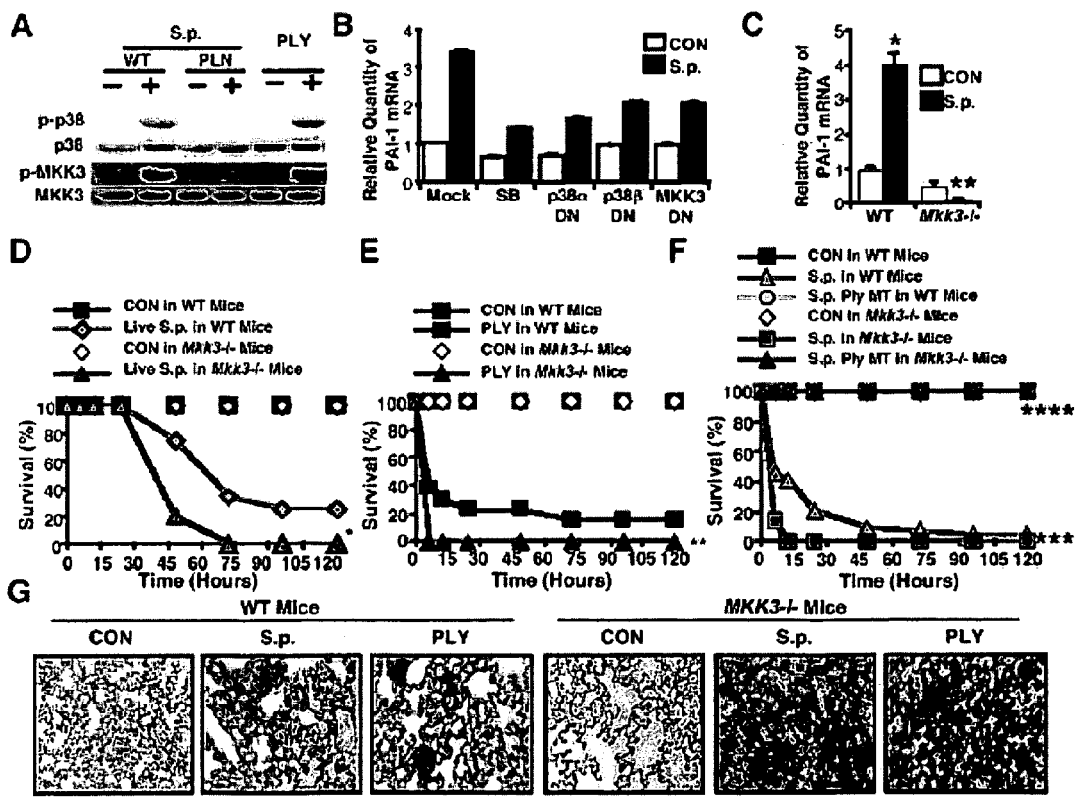
Figures 14A–G

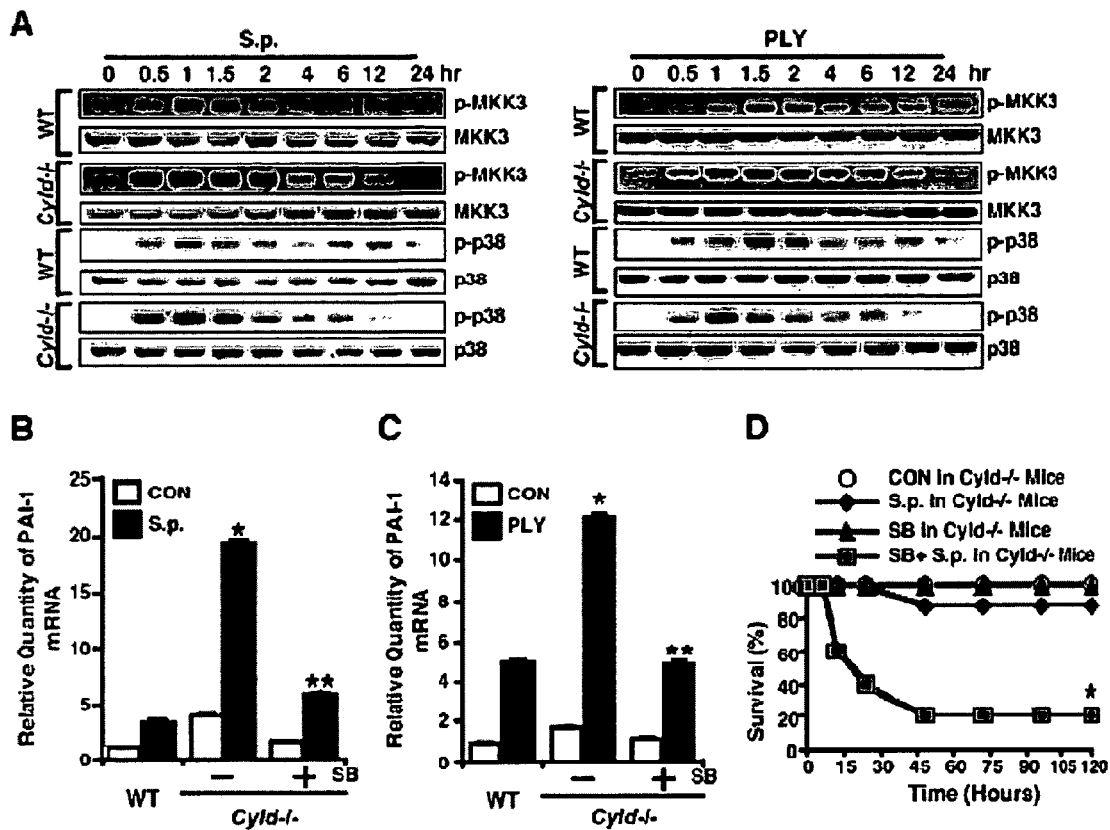
Figures 15A–D
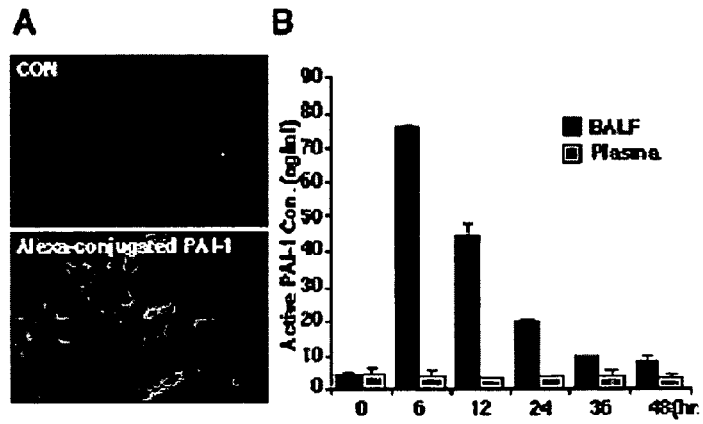
Figures 16A–B

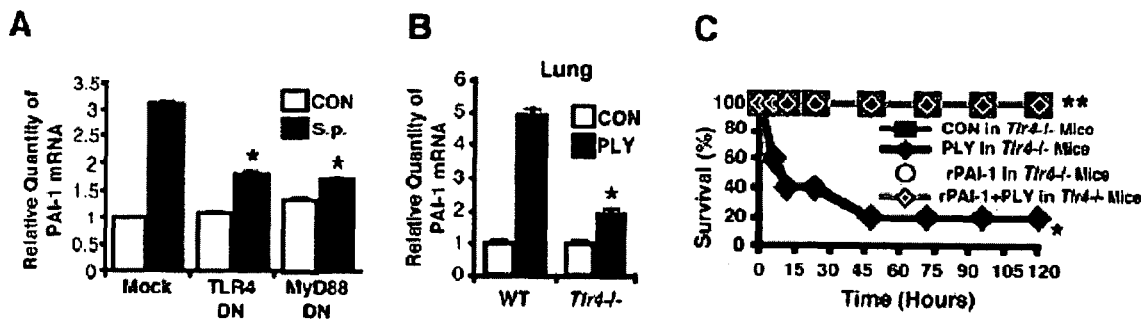
Figures 17A–C
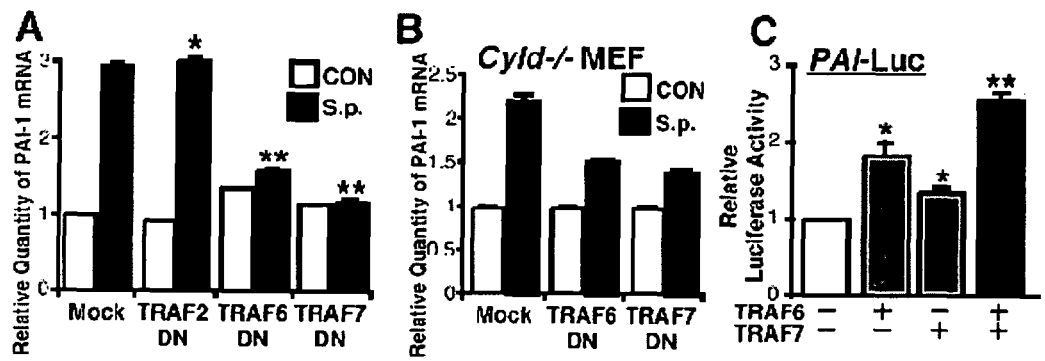
Figures 18A–C
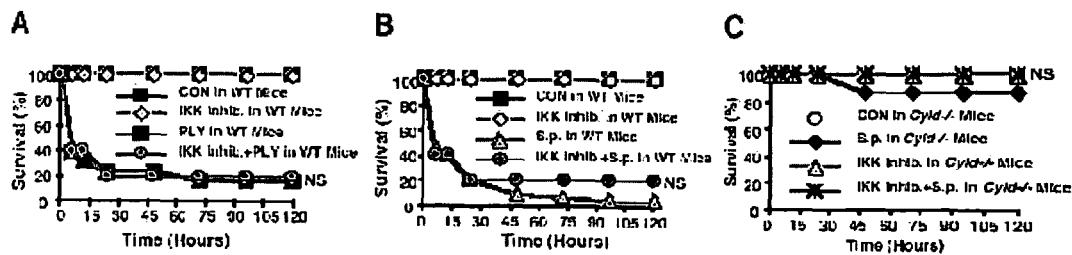
Figures 19A–C

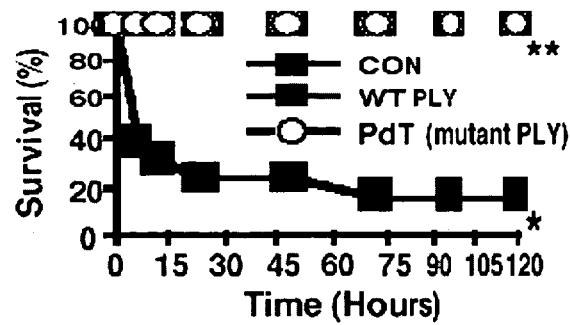
Figure 20
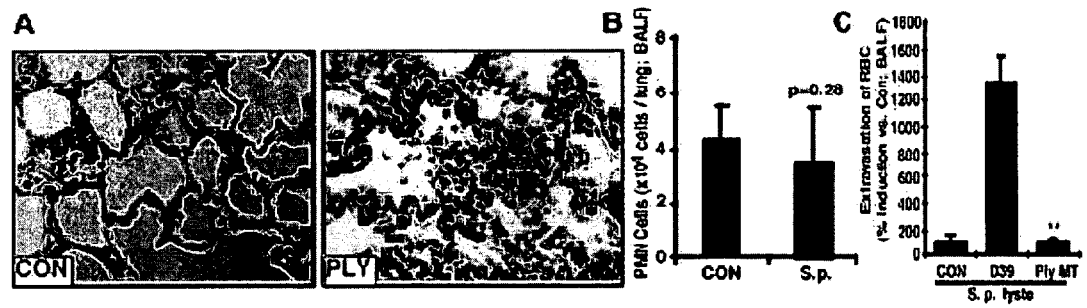
Figures 21A–C

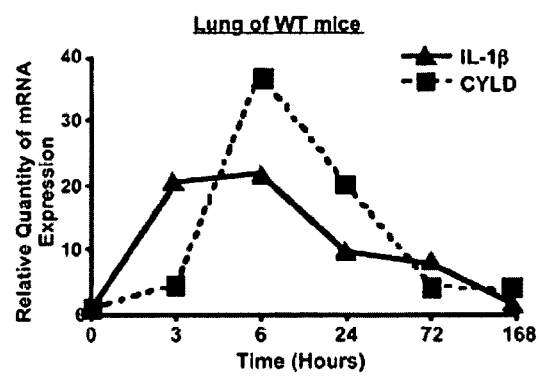
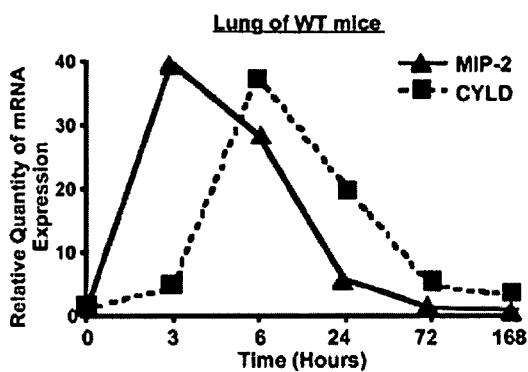
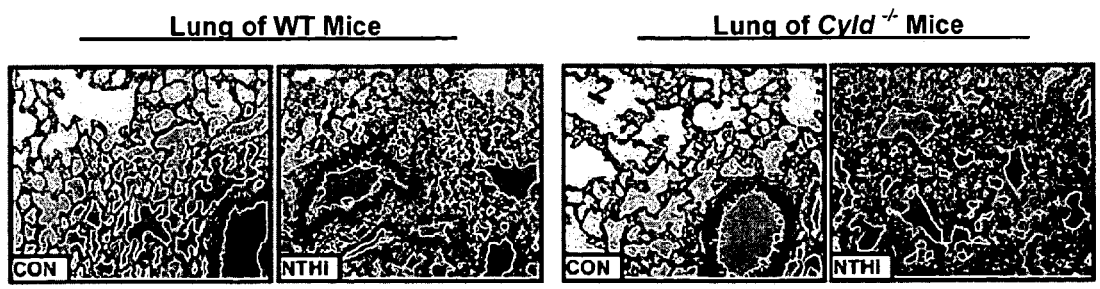
Figures 22A-C

METHODS FOR THE TREATMENT OR PREVENTION OF HEMORRHAGIC CONDITIONS

This is a national stage application under 35 U.S.C. 371 of PCT/US2008/070731, filed Jul. 22, 2008, and claims the priority benefit of U.S. Provisional Patent Application Ser. No. 60/953,289, filed Aug. 1, 2007, which is hereby incorporated by reference in its entirety.

This invention was made with government support under grants DC005843 and DC004562, awarded by the National Institutes of Health. The government has certain rights in this invention.

FIELD OF THE INVENTION

The present invention relates to methods of treating or preventing hemorrhagic conditions, particularly though not exclusively hemorrhagic conditions of the lung.

BACKGROUND OF THE INVENTION

*Streptococcus pneumoniae* ("S.p.") is an important human pathogen that colonizes the upper respiratory tract. It is a major cause of morbidity and mortality worldwide (Hollingshead & Briles, "*Streptococcus pneumoniae*: New Tools for an Old Pathogen," *Curr. Opin. Microbiol.* 4:71-7 (2001)). It causes invasive diseases such as pneumonia, meningitis and bacteraemia, as well as otitis media and sinusitis. Despite the widespread use of antibiotics, the mortality rate from severe *S. pneumoniae* pneumonia remains highest during the first 48 hours of hospitalization and has not decreased appreciably over the past 30 years (Brandenburg et al., "Clinical Presentation, Processes and Outcomes of Care for Patients with Pneumococcal Pneumonia," *J. Gen. Intern. Med.* 15:638-46 (2000); Hollingshead & Briles, "*Streptococcus pneumoniae*: New Tools for an Old Pathogen," *Curr. Opin. Microbiol.* 4:71-7 (2001)). Moreover, successful treatment of S.p.-induced pneumonia has been further hampered by the increasing prevalence of antibiotic resistant strains worldwide. The earliest stage is seldom recognized and is most likely to be found in patients who die after illness lasting only a short time period because of the very rapid progress of the disease in some of the infected individuals (Loeschcke, *Beitr. Path. Anat.* 86:201 (1931)). The molecular mechanism underlying the high early mortality, however, remains unknown (Grigoryev et al., "Science Review: Searching for Gene Candidates in Acute Lung Injury," *Crit. Care* 8:440-7 (2004); Kadioglu & Andrew, "The Innate Immune Response to Pneumococcal Lung Infection: The Untold Story," *Trends Immunol.* 25:143-9 (2004)).

Histologically, the initial phase of pneumococcal pneumonia is characterized by acute lung injury ("ALI"). ALI is defined as an inflammatory disorder of the lung, which is characterized by hypoxemia, diffuse bilateral infiltrates on chest radiograph, and absence of atrial hypertension. Although numerous bacteria are present in an actively spreading lesion, few inflammatory cells are seen in serous exudates of these lesions because leukocytes have not had time to reach the alveoli in the advancing edema zone, suggesting that alveolar epithelial cell injury may be caused directly by pneumococcal toxins rather than by leukocytes themselves or their products (Hasleton, "Pulmonary Bacterial Infection," in SPENCER'S PATHOLOGY OF THE LUNG 189-256 (Philip S. Hasleton ed., 5$^{th}$ ed. 1996); Tuomanen et al., "Pathogenesis of Pneumococcal Infection," *N. Engl. J. Med.* 332:1280-4 (1995); Wood, W. B., "Studies on the Mechanism of Recovery in Pneumococcal Pneumonia: I. The Action of Type Specific Antibody Upon the Pulmonary Lesion of Experimental Pneumonia," *J. Exp. Med.* 73:201-22 (1941)).

Despite the importance of pneumococcal diseases, little is known about the molecular mechanisms by which S.p.-induced lethality is regulated (Tuomanen et al., "Pathogenesis of Pneumococcal Infection," *N. Engl. J. Med.* 332:1280-4 (1995); Kadioglu & Andrew, "The Innate Immune Response to Pneumococcal Lung Infection: The Untold Story," *Trends Immunol.* 25:143-9 (2004)). Among a variety of virulence factors that have been identified, pneumolysin, a 53 kDa protein produced by virtually all clinical isolates of *S. pneumoniae*, plays an important role in mortality associated with *S. pneumoniae* infections (Cockeran et al., "The Role of Pneumolysin in the Pathogenesis of *Streptococcus pneumoniae* Infection," *Curr. Opin. Infect. Dis.* 15:235-9 (2002)) by inducing important pathological processes, including hemorrhage, mainly due to its well-established hemolytic cytotoxicity. Pneumolysin is located in the cytoplasm, but is released when pneumo cocci undergo spontaneous autolysis (Cockeran et al., "The Role of Pneumolysin in the Pathogenesis of *Streptococcus pneumoniae* Infection," *Curr. Opin. Infect. Dis.* 15:235-9 (2002); Tuomanen et al., "Pathogenesis of Pneumococcal Infection," *N. Engl. J. Med.* 332:1280-4 (1995); Paton, "The Contribution of Pneumolysin to the Pathogenicity of *Streptococcus pneumoniae*," *Trends Microbiol.* 4:103-6 (1996); Jedrzejas, "Pneumococcal Virulence Factors: Structure and Function," *Microbiol. Mol. Biol. Rev.* 65(2):187-207 (2001); Paton et al., "Molecular Analysis of the Pathogenicity of *Streptococcus pneumoniae*: The Role of Pneumococcal Proteins," *Annu. Rev. Microbiol.* 47: 89-115 (1993)). Pneumolysin is classically defined as a pore-forming hemolysin and is able to lyse the plasma membrane of virtually any mammalian cell.

There has been growing evidence indicating that pneumolysin plays an important role in inducing acute lung hemorrhage and mortality, especially during the early stages of lethal S.p. infections. Pathologically, the initial phase of S.p.-induced pneumonia is mainly characterized by pulmonary alveolar hemorrhage, edema, and intra-alveolar bacterial multiplication but minimal numbers of inflammatory cells, suggesting that pneumolysin is capable of disrupting the normal alveolar-capillary barrier (Rubins & Janoff, "Pneumolysin: A Multifunctional Pneumococcal Virulence Factor," *J. Lab. Clin. Med.* 131:21-7 (1998); Wood, W. B., "Studies on the Mechanism of Recovery in Pneumococcal Pneumonia: I. The Action of Type Specific Antibody Upon the Pulmonary Lesion of Experimental Pneumonia," *J. Exp. Med.* 73:201-22 (1941)). Indeed, pneumolysin has been shown to be cytotoxic to alveolar epithelial cells and pulmonary endothelial cells in vitro (Rubins et al., "Toxicity of Pneumolysin to Pulmonary Endothelial Cells in Vitro. *Infect. Immun.* 60:1740-6 (1992); Rubins et al., "Toxicity of Pneumolysin to Pulmonary Alveolar Epithelial Cells," *Infect. Immun.* 61:1352-8 (1993)) and disrupts the alveolar-capillary barrier in isolated perfused lungs (Rubins et al., "Toxicity of Pneumolysin to Pulmonary Alveolar Epithelial Cells," *Infect. Immun.* 61:1352-8 (1993)). Moreover, histopathological change of pneumococcal pneumonia was reproduced with pneumolysin in vivo (Maus et al., "Pneumolysin-induced Lung Injury Is Independent of Leukocyte Trafficking into the Alveolar Space," *J. Immunol.* 173: 1307-12 (2004)). Electron microscopy revealed that instilled pneumolysin caused widespread lung injury. Direct cytotoxic effect of pneumolysin to the alveolar epithelium, as well as to the pulmonary endothelium, may produce alveolar flooding and hemorrhage during the earliest stages of pneumococcal pneumonia. The resulting serous exudates may in turn promote the rapid multiplication of *S. pneumoniae* within the alveoli. The lesion progresses to the state known as red hepatization, which results from leakage of erythrocytes into the alveoli (Rubins et al., "Toxicity of Pneumolysin to Pulmonary Alveolar Epithelial Cells," *Infect. Immun.* 61:1352-8 (1993)).

Despite the availability of antibiotic and intensive supportive therapy, this early mortality has not been significantly reduced over the past 30 years. Moreover, successful treatment of S.p.-induced pneumonia has been further hampered by the increasing prevalence of antibiotic resistant strains worldwide. Therefore, currently there is an urgent need for developing novel therapeutic strategies for controlling S.p. pneumolysin-induced lung hemorrhage and reducing mortality.

The present invention is directed to overcoming these and other deficiencies in the art.

SUMMARY OF THE INVENTION

The present invention relates to a method for treatment or prevention of a hemorrhagic condition in a patient. This method involves administering to a patient an amount of plasminogen activator inhibitor-1 ("PAI-1"), an inhibitor of deubiquitinating enzyme CYLD (hereinafter "CYLD," which is also known as deubiquitinase), or a combination thereof, under conditions effective to treat or prevent the hemorrhagic condition in the patient.

Another aspect of the present invention relates to a pharmaceutical composition that includes a pharmaceutically acceptable carrier and an amount of one or both of PAI-1 and an inhibitor of CYLD, which is effective to treat a hemorrhagic condition, preferably hemorrhagic lung conditions.

*S. pneumoniae* is a major cause of high early mortality in pneumococcal pneumonia, which is characterized by acute lung injury ("ALI"). The molecular mechanisms underlying ALI and the high early mortality remain unknown. Despite recent studies that identify deubiquitinating enzyme CYLD as a key regulator for T cell development, tumor cell proliferation, and NF-κB signaling, its role in regulating bacteria-induced lethality had—prior to the present invention—remained unclear. The present invention shows that CYLD deficiency protects mice from *S. pneumoniae* pneumolysin ("PLY")-induced ALI and lethality. CYLD, highly induced by PLY, inhibits MKK3-p38 MAPK-dependent expression of PAI-1 in lung, thereby potentiating ALI and mortality. The present invention identifies CYLD as a crucial negative regulator for host survival, thereby unveiling a novel mechanism underlying the high early mortality of pneumococcal pneumonia. The present invention provides novel therapeutic strategies for reducing high early mortality in otherwise lethal *S. pneumoniae* infections.

BRIEF DESCRIPTION OF THE DRAWINGS

FIGS. 2A-C demonstrate that *S. pneumoniae* pneumolysin induces acute lung injury and lethality in vivo. FIG. 2A is a graph of the survival rates of wild type mice after intratracheal inoculation of saline ("CON"), live *S. pneumoniae* D39 ("Live S.p."), or *S. pneumoniae* D39 lysate ("S.p. lysate"). *$p<0.0005$ compared with CON; **$p<0.0005$ compared with live *S. pneumoniae* (n=10 to 44). FIG. 2B is a graph of the survival rates of wild type mice after intratracheal inoculation of saline ("CON"), wild type *S. pneumoniae* D39 lysate ("S.P. WT"), *S. pneumoniae* pneumolysin mutant lysate ("S.p. Ply MT"), or purified pneumolysin ("Pneumolysin (PLY)"). *$p<0.0005$ compared with CON; **$p<0.0005$ compared with wild type *S. pneumoniae* D39 lysate (n=10 to 44). FIG. 2C is a series of representative images relating to the pathological and histological analysis of the lungs of mice inoculated with saline ("CON"), wild type *S. pneumoniae* D39 lysate ("S.p. WT"), *S. pneumoniae* pneumolysin mutant lysate ("S.p. Ply MT"), or purified pneumolysin ("PLY") (bottom panels: H&E-stained sections at 100× magnification).

FIG. 3 is a graph of the survival curves of wild type mice after intratracheal inoculation of saline ("CON"), *S. pneumoniae* strain D39 lysate, or *S. pneumoniae* strain TIGR4 lysate. Wild type mice were inoculated with $5 \times 10^7$ CFU of *S. pneumoniae* D39 lysate or TIGR4 lysate and the survival rate was recorded for 5 days after inoculation. Viability was assessed using Kaplan-Meier Survival analysis and compared by log-rank test (n=10 to 44). *$p<0.0005$ compared with CON; non significant ("NS") compared to *S. pneumoniae* D39 inoculation.

FIG. 4 is a pair of images of an H&E-stained section of necropsy lung tissue from an 18-year old male who died from pneumococcal lobar pneumonia with massive alveolar hemorrhage but few polymorphonuclear leukocytes.

FIGS. 5A-B relate to the generation of Cyld-deficient mice. FIG. 5A is a diagram of the mouse Cyld gene shown with the targeting vector and the targeted allele. Homologous recombination resulted in deletion of exons 1 and 2 and insertion of a lacZ reporter. FIG. 5B is a Southern blot (top) and immunoblot (bottom) of mouse embryonic fibroblasts from wild-type ("WT") and Cyld-deficient ("Cyld-/-") mice. Glyceraldehyde 3-phosphate dehydrogenase ("GAPDH") (top) and β-actin (bottom) were used as controls. RT-PCR and western blot analysis were performed, respectively, to assess Cyld mRNA and protein expression.

FIGS. 6A-G demonstrate that Cyld deficiency protects mice from acute lung injury and reduces mortality in lethal *S. pneumoniae* infections. FIG. 6A is a graph of the relative quantity of CYLD mRNA in the lungs of mice inoculated with saline ("CON"), wild type *S. pneumoniae* D39 lysate ("WT"), *S. pneumoniae* pneumolysin mutant lysate ("PLN"), or purified pneumolysin ("PLY"). As assessed by Q-PCR, CYLD expression at the mRNA level in lung tissues from wild type mice was greatly up-regulated by the *S. pneumoniae* wild type lysate and by pneumolysin, but not by the *S. pneumoniae* pneumolysin mutant lysate. *$p<0.05$ compared with CON; **$p<0.05$ compared with wild type lysate. Data are the means±S.D. (n=3). FIGS. 6B and 6C are graphs of the survival rates of wild type ("WT") and Cyld-deficient ("Cyld-/-") mice after intratracheal inoculation of saline ("CON"), *S. pneumoniae* D39 lysate ("S.p.") (FIG. 6B), or purified pneumolysin ("PLY") (FIG. 6C). *$p<0.0005$ compared with CON in wild type mice; **$p<0.0005$ compared with *S. pneumoniae* lysate and pneumolysin in wild type mice (n=10 to 44). FIG. 6D is a series of representative images relating to the pathological and histological analysis of the lungs of wild type ("WT") and Cyld-deficient ("CYLD-/-") mice inoculated with saline ("CON"), *S. pneumoniae* D39 lysate ("S.p."), or purified pneumolysin ("PLY") (bottom panels: H&E-stained lung sections at 100× magnification). FIG. 6E is a plot showing the changes in body temperature of wild type ("WT Mice") and Cyld-deficient ("Cyld-/-Mice") mice inoculated with saline ("CON"), wild type *S. pneumoniae* D39 lysate ("WT"), *S. pneumoniae* pneumolysin mutant lysate ("PLN"), or purified pneumolysin ("PLY"). *$p<0.005$;

p<0.005; *p<0.05; ****p<0.005 (n=3 to 6). FIG. 6F is a graph of the total protein concentrations of bronchoalveolar lavage fluid ("BALF") from the mice of FIG. 6E. *p<0.05 compared with CON in wild type mice; p<0.05 compared with the wild type lysate or mutant lysate in wild type mice; *p<0.05 compared with the wild type lysate in wild type mice (n=3 to 6). FIG. 6G is a graph of the lung water weight of the mice of FIGS. 6E and 6F. *p<0.00001 compared with CON in wild type mice; p<0.005 compared with the wild type lysate and pneumolysin in wild type mice; *p<0.00001 compared with the wild type lysate in wild type mice (n=3 to 6).

FIGS. 7A-B are plots of the bacterial counts in the lung (FIG. 7A) and blood (FIG. 7B) of wild type ("WT") and Cyld-deficient ("Cyld-/-") mice at 24 hours after inoculation with 5×10$^7$ CFU of *S. pneumoniae* strain D39 ("WT D39") or *S. pneumoniae* Ply MT ("Ply MT") (n=10).

FIGS. 8A-H demonstrate that Cyld deficiency protects against pneumolysin-induced acute lung injury and death via enhancement of PAI-1 expression in lung. FIG. 8A is a pair of graphs (top) of the relative PAI-1 mRNA expression (assessed by Q-PCR analysis) in mouse embryonic fibroblasts ("MEF") and lung tissue ("Lung") of wild-type ("WT") and Cyld-deficient ("Cyld-/-") mice, and western blots (bottom panel) of the MEF and lung tissue of these mice. PAI-1 expression at the mRNA and protein levels was much higher in the MEF and lung tissue from the Cyld$^{-/-}$ mice than that from the wild type mice. *p<0.05 compared with wild type. FIG. 8B is a graph of the relative quantity of PAI-1 mRNA in MEF of wild type ("WT") or Cyld$^{-/-}$ ("Cyld-/-") mice inoculated with wild type *S. pneumoniae* D39 ("S.p.") or purified pneumolysin ("PLY"), or not inoculated ("CON"). FIG. 8C is a graph of the relative quantity of PAI-1 mRNA in lung tissue of wild type ("WT") or Cyld$^{-/-}$ ("Cyld-/-") mice inoculated with wild type *S. pneumoniae* D39 ("S.p.") or not inoculated ("CON"). As shown in FIGS. 8B-C, expression levels of PAI-1 mRNA were much higher in MEF (FIG. 8B, right) and lung tissue (FIG. 8C, right) of the Cyld$^{-/-}$ mice than in MEF (FIG. 8B, left) and lung tissue (FIG. 8C, left) of the wild type mice. *p<0.005 compared with control in wild type mice; **p<0.0005 compared with *S. pneumoniae* or pneumolysin in wild type mice (n=4). FIG. 8D is a series of representative images of H&E-stained lung sections from untreated Cyld$^{-/-}$ mice ("CON"), and from Cyld$^{-/-}$ mice after inoculation with *S. pneumoniae* alone ("S.p.") or with *S. pneumoniae* 2 hours after intraperitoneal pre-administration of α-PAI-1 mAb (25 μg/mouse) (200× magnification; insets, 400× magnification). FIG. 8E is a graph of the survival rates of Cyld$^{-/-}$ mice after intratracheal inoculation of *S. pneumoniae* D39 lysate with ("α-PAI-1 +S.p.") or without ("CON") pre-administration (2 hours before *S. pneumoniae* inoculation) of α-PAI-1 neutralizing mAb (50 μg/mouse), or inoculation of *S. pneumoniae* D39 lysate with pre-administration of IgG as a control ("Con IgG+S.p."). *p<0.005 compared with control IgG (n=10 to 30). FIGS. 8F and 8G are graphs of the survival rates of wild type mice inoculated with saline ("CON"), *S. pneumoniae* D39 lysate alone ("S.p."), purified pneumolysin alone ("PLY"), 12.5 μg/mouse of recombinant mouse PAI-1 alone ("rPAI-1"), *S. pneumoniae* D39 lysate with pre-administration of rPAI-1 (12.5 μg/mouse) 1 day before *S. pneumoniae* inoculation ("rPAI-1+S.p."), or purified pneumolysin with pre-administration of rPAI-1 (12.5 μg/mouse) 1 day before pneumolysin inoculation ("rPAI-1+PLY"). *p<0.0005 compared with CON; **p<0.0005 compared with *S. pneumoniae* and pneumolysin inoculation without rPAI-1 pre-administration (n=10 to 44). FIG. 8H is a series of representative images of the pathological and histological analysis of the lungs of wild type mice untreated ("CON") or treated with rPAI-1 alone ("rPAI-1"), *S. pneumoniae* D39 alone ("S.p."), purified pneumolysin alone ("PLY"), or *S. pneumoniae* D39 or purified pneumolysin with pre-administration of rPAI-1 ("rPAI-1+S.p." and "rPAI-1+PLY," respectively) (lower panels: H&E-stained sections at 100× magnification).

FIGS. 9A-B show that CYLD negatively regulates PAI-1 expression. FIG. 9A is a graph of the relative quantity of PAI-1 mRNA in MEF cells of wild type ("WT MEF") and Cyld-deficient ("Cyld-/-MEF") mice. Test cells optionally contained small interfering RNA against CYLD ("siRNA-CYLD"), or overexpressed CYLD ("wt-CYLD"). CYLD knock-down using siRNA-CYLD increased PAI-1 mRNA expression in MEF cells from wild type mice, and overexpression of CYLD reduced PAI-1 mRNA expression in MEF cells from Cyld$^{-/-}$ mice. *p<0.005 compared with wild type control MEF cells; p<0.05 compared with wild type control MEF cells; *p<0.05 compared with Cyld$^{-/-}$ control MEF cells. Data are the means±S.D. (n=3). FIG. 9B is a graph of the relative luciferase ("Luc") activity in MEF cells from wild type ("WT MEF") and Cyld-deficient ("Cyld-/-MEF") mice containing increasing amounts of siRNA against CYLD ("siRNA-CYLD"), or overexpressing wild type CYLD ("wt CYLD") at increasing levels. PAI-1 promoter activity was increased by siRNA-CYLD in MEF cells from wild type mice, but downregulated by wild type CYLD in MEF cells from Cyld$^{-/-}$ mice in a dose-dependent manner. *p<0.05 compared with wild type control MEF; p<0.005 compared with wild type control MEF; *p<0.0001 compared with wild type control MEF; ****p<0.05 compared with Cyld$^{-/-}$ MEF. Data are the means±S.D. (n=3).

FIGS. 10A-C show that *S. pneumoniae* induces PAI-1 expression through the cytoplasmic toxin pneumolysin. FIGS. 10A-C are graphs of the relative quantity of PAI-1 mRNA in human alveolar epithelial A549 cells ("A549") (FIG. 10A), primary human small airway epithelial cells ("SAEC") (FIG. 10B), and wild type mice lungs ("Lung") (FIG. 10C), inoculated with saline ("CON"), *S. pneumoniae* WT lysate ("S.p. WT"), *S. pneumoniae* Ply MT lysate ("Ply MT"), or purified pneumolysin ("PLY"). *S. pneumoniae* WT lysate and purified pneumolysin induced PAI-1 expression in A549, SAEC, and Lung, but *S. pneumoniae* Ply MT lysate did not. *p<0.05 compared with CON; **p<0.005 compared with *S. pneumoniae* WT lysate.

FIGS. 11A-L are a series of images relating to the immunohistochemical analysis of PAI-1 expression from wild type mice (FIGS. 11A-F) and Cyld-deficient mice ("Cyld-/-") (FIGS. 11G-L) after *S. pneumoniae* inoculation. Shown are lung tissue sections of mice inoculated with saline ("CON") or *S. pneumoniae*, and labeled with polyclonal anti-PAI-1 antibody ("anti-PAI-1") to detect PAI-1 protein expression or with IgG ("Control IgG") as a control. FIGS. 11E, 11F, 11K, and 11L show higher magnification sections of the corresponding anti-PAI-1 images.

FIGS. 12A-D demonstrate that PAI/-/-deficient ("PAI-1$^{-/-}$") mice are hyper-susceptible to severe *S. pneumoniae* infection. FIGS. 12A-C are graphs of the survival rates of wild type and PAI-1$^{-/-}$ mice after intratracheal inoculation of live *S. pneumoniae* (FIG. 12A), *S. pneumoniae* D39 lysate (FIG. 12B), or purified pneumolysin (FIG. 12C). "CON in WT Mice": wild type mice treated with saline; "Live S.p. in WT Mice," "S.p. in WT Mice," and "PLY in WT Mice": wild type mice inoculated, respectively, with live *S. pneumoniae*, *S. pneumoniae* lysate, or pneumolysin; "CON in PAI-1-/- mice": PAI-1$^{-/-}$ mice treated with saline; "Live S.p. in PAI-1-/- mice," "S.p. in PAI-1-/- mice," and "PLY in PAI-1-/- mice": PAI-1 mice inoculated, respectively, with live *S. pneumoniae*, *S. pneumoniae* lysate, or pneumolysin. *p<0.001 compared with CON in wild type mice; **p<0.05 compared with live *S. pneumoniae*, *S. pneumoniae* lysate, or pneumolysin in wild type mice (n=10 to 44). FIG. 12D is a series of representative images of H&E-stained lung sections from wild type and PAI-1$^{-/-}$ mice after treatment with saline ("CON") or inoculation with *S. pneumoniae* lysate ("S.p.") or purified pneumolysin ("PLY") (200× magnification).

FIGS. 13A-C are graphs of the survival rates of wild type and PAI-1-deficient ("PAI-1$^{-/-}$") mice inoculated with *S. pneumoniae* strain D39 or strain ATCC 6303. FIG. 13A shows the survival curves of wild type ("WT") and PAI-1$^{-/-}$ ("PAI-1-/-") mice intranasally inoculated with 5×10$^7$ CFU of *S. pneumoniae* strain D39. Viability was assessed for 5 days after inoculation. FIG. 13B shows the survival curves of wild type mice inoculated with 5×10$^7$ CFU of *S. pneumoniae* strain ATCC 6303 ("Sp 6303 5×10$^7$"), 2×10$^5$ CFU of *S. pneumoniae* strain ATCC 6303 ("Sp 6303 2×10$^5$"), 5×10$^7$ CFU of *S. pneumoniae* strain D39 ("Sp D39 5×10$^7$"), or 2×10$^5$ CFU of *S. pneumoniae* strain D39 ("Sp D39 2×10$^5$"). Viability was assessed for 5 days after inoculation. FIG. 13C shows the survival curves of wild type and PAI-1$^{-/-}$ ("PAI-1-/-") mice intranasally inoculated with 2×10$^5$CFU of *S. pneumoniae* strain ATCC 6303. Viability was assessed for 5 days after inoculation. *p<0.05 compared with wild type mice inoculated with 5×10$^7$ CFU of strain D39; p<0.05 compared with wild type mice inoculated with 5×10$^7$ CFU of strain D39; *p<0.05 compared with wild type mice inoculated with 2×10$^5$ CFU of strain D39; ****p<0.05 compared with wild type mice inoculated with 2×10$^5$ CFU of strain ATCC 6303. Survival rate was assessed using Kaplan-Meier Survival analysis and compared by a log-rank test (n=10 to 30).

FIGS. 14A-G show that *S. pneumoniae* pneumolysin induces PAI-1 expression via the MKK3-p38 MAPK signaling pathway. FIG. 14A is a blot of human alveolar epithelial A549 cell lysates inoculated with wild type *S. pneumoniae* ("WT"), the *S. pneumoniae* pneumolysin-deficient mutant ("PLN"), or purified pneumolysin ("PLY"). "p-p38" and "p38": phosphorylated and dephosphorylated p38, respectively; "p-MKK3" and "MKK3": phosphorylated and dephosphorylated MKK3, respectively. Wild type *S. pneumoniae* and pneumolysin both induced phosphorylation of p38 and MKK3 in A549 cells, but the pneumolysin-deficient mutant did not. FIG. 14B is a graph of the relative quantity of PAI-1 mRNA in mock-transfected A549 cells ("Mock"), A549 cells treated with the p38 inhibitor SB203580 ("SB"), and A549 cells expressing a dominant negative p38α mutant ("p38αDN"), a dominant negative p38β mutant ("p38βDN"), or a dominant negative MKK3 mutant ("MKK3DN"). All cells were treated with saline ("CON") or inoculated with *S. pneumoniae* ("S.p."). *S. pneumoniae*-induced PAI-1 mRNA expression was inhibited in A549 cells by SB203580 treatment and by expressing dominant-negative mutant forms of p38α, p38β, and MKK3. SB203580 is 4-(4-fluorophenyl-2-(4-methylsulfinylphenyl)-5-(4-pyridyl)-1H-imidazole, a known anti-inflammatory agent. FIG. 14C is a graph of the relative quantity of PAI-1 mRNA in lung of wild type ("WT") and Mkk3-deficient ("Mkk3$^{-/-}$") mice treated with saline ("CON") or inoculated with *S. pneumoniae* ("S.p."). *S. pneumoniae*-induced PAI-1 expression at the mRNA level was reduced in Mkk3$^{-/-}$ mouse lung compared with that in wild type mouse lung. *p<0.05 compared with CON; **p<0.0001 compared with *S. pneumoniae* in wild type mice (n=4). FIGS. 14D-F are graphs of the survival rates of wild type and Mkk3$^{-/-}$ mice after inoculation with saline ("CON") or live *S. pneumoniae* (FIG. 14D), saline ("CON") or purified pneumolysin (FIG. 14E), and either saline ("CON"), *S. pneumoniae* WT lysate, or *S. pneumoniae* pneumolysin mutant ("Ply MT") lysate (FIG. 14F). "CON in WT Mice" and "CON in Mkk3-/- Mice": wild type and Mkk3$^{-/-}$ mice, respectively, inoculated with saline; "Live S.p. in WT Mice," "PLY in WT Mice," "S.p. in WT Mice," and "S.p. PLY MT in WT Mice": wild type mice inoculated, respectively, with live *S. pneumoniae*, pneumolysin, *S. pneumoniae* WT lysate, or *S. pneumoniae* Ply MT lysate; "Live S.p. in Mkk3-/- Mice," "PLY in Mkk3-/- Mice," "S.p. in Mkk3-/- Mice," and "S.p. Ply MT in Mkk3-/- Mice": Mkk3$^{-/-}$ mice inoculated, respectively, with live *S. pneumoniae*, pneumolysin, *S. pneumoniae* WT lysate, or *S. pneumoniae* Ply MT lysate. *p<0.0005 compared with live *S. pneumoniae* in wild type mice; p<0.05 compared with pneumolysin in wild type mice; *p<0.05 compared with *S. pneumoniae* WT lysate in wild type mice; ****p<0.0005 compared with *S. pneumoniae* WT lysate in Mkk3$^{-/-}$ mice (n=10 to 44). FIG. 14G is a series of representative images of H&E-stained lung sections from wild type ("WT") and Mkk3-deficient mice ("MKK3-/-") after inoculation with saline ("CON"), *S. pneumoniae* lysate ("S.p.") or pneumolysin ("PLY") (100× magnification).

FIGS. 15A-D show that CYLD acts as a negative regulator for PAI-1 expression via negative cross-talk with the MKK3-p38 MAPK signaling pathway. FIG. 15A is a pair of blots of mouse embryonic fibroblasts ("MEF") from wild type ("WT") and Cyld-deficient ("Cyld-/-") mice at 0, 0.5, 1, 1.5, 2, 4, 6, 12, or 24 hours after inoculation with *S. pneumoniae* WT lysate (left) or purified pneumolysin (right), showing the kinetics of *S. pneumoniae*- and pneumolysin-induced phosphorylation of MKK3 and p38. "p-MKK3" and "MKK3": phosphorylated and dephosphorylated MKK3, respectively; "p-p38" and "p38": phosphorylated and dephosphorylated p38, respectively. FIGS. 15B and 15C are graphs of the relative quantity of PAI-1 mRNA in MEF cells from wild type ("WT") and Cyld-deficient ("Cyld-/-") mice inoculated with saline ("CON"), *S. pneumoniae* WT lysate ("S.p."), or purified pneumolysin ("PLY"), with (+) or without (−) pretreatment with SB203580 ("SB"). Pretreatment with SB203580 reduced PAI-1 mRNA expression in Cyld$^{-/-}$ cells, regardless of their treatment with *S. pneumoniae* (FIG. 15B) or pneumolysin (FIG. 15C). *p<0.05 compared with *S. pneumoniae* or pneumolysin in wild type MEF; **p<0.05 compared with *S. pneumoniae* or pneumolysin without SB203580 (n=4). FIG. 15D is a graph of the survival rates of Cyld$^{-/-}$ mice after inoculation with saline ("CON in Cyld-/- Mice"), *S. pneumoniae* with vehicle ("S.p. in Cyld-/- Mice"), or 10 mg/kg of SB203580 ("SB in Cyld$^{-/-}$ Mice"), and Cyld$^{-/-}$ mice inoculated with *S. pneumoniae* pretreated with 10 mg/kg of SB203580 2 hours before *S. pneumoniae* inoculation ("SB+ S.p. in Cyld-/- Mice"). *p<0.0005 compared with *S. pneumoniae* inoculation without SB203580 pretreatment (n=10 to 44).

FIGS. 16A-B illustrate that exogenous PAI-1 protects against alveolar hemorrhage and early lethality in WT mice. FIG. 16A is an image showing fluorescence detection of exogenously inoculated PAI-1 ("Alexa-conjugated PAI-1") in the lungs of WT mice, as compared to saline control ("CON"). Alexa Flour 488-conjugated PAI-1 was intratracheally inoculated into the lungs of WT mice (0.6 mg/kg BW), and localization of the PAI-1 was detected 6 hours after inoculation by using fluorescence microscopy. FIG. 16B shows the concentration of active PAI-1 measured from the BALF and blood ("Plasma") after intratracheal inoculation of active PAI-1 (0.6 mg/kg body weight) by using ELISA kit.

FIGS. 17A-C show that TLR4-MyD88 signaling is required for *S. pneumoniae* pneumolysin-induced PAI-1 expression. FIG. 17A is a graph of the relative quantity of PAI-1 mRNA in A549 cells Overexpressing a dominant-negative mutant of TLR4 ("TLR4DN"), A549 cells Overexpressing a dominant-negative mutant of MyD88 ("MyD88 DN"), and mock-transfected A549 control cells ("Mock"). Cells were inoculated with saline ("CON") or *S. pneumoniae* WT ("S.p."). Overexpressing a dominant-negative mutant of TLR4 or MyD88 inhibited *S. pneumoniae*-induced PAI-1 expression in A549 cells. *$p<0.005$ compared with control cells treated with *S. pneumoniae* (n=4). FIG. 17B is a graph of the relative quantity of PAI-1 mRNA in lung tissue of wild type ("WT") and Tlr4-deficient ("Tlr4-/-") mice inoculated with saline ("CON") or pneumolysin ("PLY"). Pneumolysin-induced PAI-1 mRNA expression was much lower in the lungs of Tlr4-deficient mice than in the lungs of wild type mice. *$p<0.05$ compared with wild type mice treated with pneumolysin (n=4). FIG. 17C is a graph of the survival rates of Tlr4-deficient ("Tlr4$^{-/-}$") mice after pneumolysin inoculation with or without pre-administration of mouse rPAI-1. "CON in Tlr4-/- Mice": Tlr4$^{-/-}$ mice inoculated with saline; "PLY In Tlr4-/- Mice": Tlr4$^{-1}$ mice inoculated with rPAI-1; "rPAI-1 in Tlr4-/- Mice": Tlr4$^{-/-}$ mice treated with rPAI-1; "rPAI-1+PLY in Tlr4-/- Mice": Tlr4$^{-/-}$ mice inoculated with pneumolysin after pre-administration with rPAI-1. *$p<0.0005$ compared with the control ("CON"); **$p<0.0005$ compared with pneumolysin inoculation without pre-administration of rPAI-1. Viability was assessed using Kaplan-Meier Survival analysis and compared by log-rank test (n=10 to 44).

FIGS. 18A-C are graphs showing that TRAF6 cooperates with TRAF7 to mediate S.p.-induced expression of PAI-1. Overexpression of a dominant negative ("DN") form of TRAF6 and TRAF7 but not TRAF2 inhibited *S. pneumoniae*-induced PAI-1 upregulation in human lung epithelial A549 cells (FIG. 18A) & Cyld$^{-/-}$ mouse embryonic fibroblasts (FIG. 18B). *$p<0.05$ compared with Mock transfected cells without *S. pneumoniae* ("CON"); **$p<0.05$ compared with Mock transfected cells treated with *S. pneumoniae* ("S.p."). FIG. 18C shows that TRAF6 cooperated with TRAF7 to induce PAI-1 in A549 cells. *$p<0.05$ compared with Mock transfected cells; **$p<0.05$ compared with cells transfected with TRAF6 or TRAF7 alone. Values are the means±SD (n=3).

FIGS. 19A-C are survival curves showing that CYLD deficiency protects against alveolar hemorrhage early lethality in severe *S. pneumoniae* infections independently of the NF-κB pathway. Survival curves of wild type ("WT") and Cyld$^{-/-}$ (Cyld-/-) mice after pneumolysin ("PLY") or *S. pneumoniae* ("S.p.") inoculation with vehicle ("CON") or the IKK inhibitor Wedelolactone ("IKK Inhib") (10 mg/kg, intraperitoneally) pretreatment 2 hours before pneumolysin or *S. pneumoniae* inoculation. NS=Non significant. Viability was assessed by using Kaplan-Meier Survival analysis and compared by log-lank test (n=10 to 44).

FIG. 20 is a graph illustrating that cytolytic activity of pneumolysin is required for pneumolysin-induced early lethality. It shows the survival curves of WT mice after intratracheal inoculation of saline ("CON"), wild type pneumolysin ("WT PLY"), or a cytolytic activity-deficient pneumolysin mutant ("PdT (mutant PLY)"). *$p<0.0005$ compared with CON; **$p<0.0005$ compared with WT PLY.

FIGS. 21A-C illustrate that alveolar hemorrhage is a hallmark of severe S.p. infection at the early stage of infection. FIG. 21A is an image of representative histological analysis of the lungs of mice inoculated with saline ("CON") or wild type pneumolysin ("PLY"). WT mice were intratracheally inoculated with 200 ng of PLY, and histological analysis of the lungs was assessed 6 hours after inoculation (H&E stain, 200×). FIG. 21B is a graph illustrating peripheral mononuclear cell ("PMN") counts from the bracheoalveolar lavage fluid ("BALF") of WT mice intratracheally inoculated with WT *S. pneumoniae* lysate ("S.p.") or saline control ("CON"). PMN cells were counted from the BALF 6 hours after inoculation. Values are the means±SD (n=3). FIG. 21C is a graph of the extravasation of red blood cells ("RBC") from WT mice intratracheally inoculated with saline control ("CON") wild-type *S. pneumoniae* D39 lysate ("D39"), or *S. pneumoniae* mutant pneumolysin lysate ("Ply MT"). Extravasation of RBC was measured from the BALF of inoculated mice 6 hours after inoculation. The percent increase of RBC leakage compared with the control was calculated by a standard curve obtained with mouse blood. Values are the means±SD (n=3 to 6). *, $p<0.001$ compared with CON; **, $p<0.001$ compared with D39.

FIGS. 22A-C illustrate the effect of nontypeable *Haemophilus influenza* ("NTHi") lung infection on CYLD expression and the resulting inflammatory response. FIGS. 22A-B show the NTHi-induced expression of CYLD and IL-1β (FIG. 22A) or MIP-2 (FIG. 22B) at the mRNA level in the lung of WT mice. FIG. 22C shows the effect of NTHi intratracheally inoculated into the lungs of WT (left panels) and Cyld (right panels) mice. Lung tissues were dissected from WT and Cyld$^{-/-}$ mice inoculated with NTHi and saline control ("CON") for histological analysis (H&E stain, 200×).

DETAILED DESCRIPTION OF THE INVENTION

Figure 1:
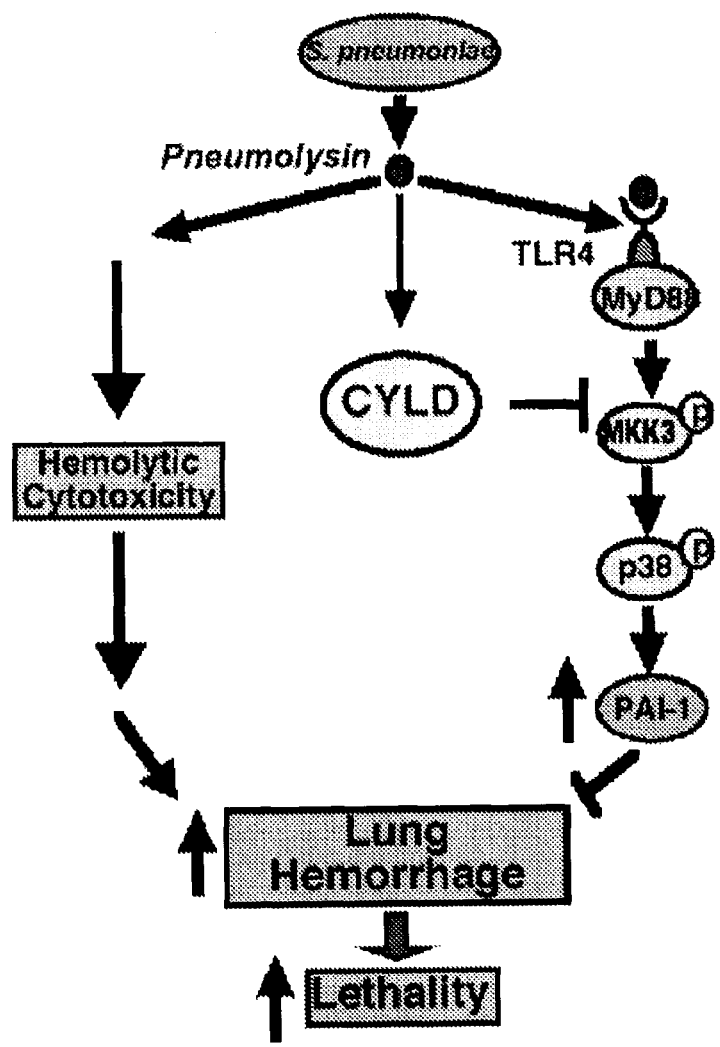
FIG. 1 is a schematic representation of the mechanism of *S. pneumoniae*-induced lethality. This mechanism includes the negative regulation of MKK3-p38 MAPK-dependent PAI-1 expression by CYLD in lung, leading to lung injuries (including hemorrhage) and increased mortality rate in lethal *S. pneumoniae* infections.

The present invention relates to a method for treatment or prevention of a hemorrhagic condition in a patient and pharmaceutical compositions that can be administered to patients for treating or preventing the hemorrhagic condition.

This method involves administering to a patient an amount of plasminogen activator inhibitor-1 ("PAI-1"), an inhibitor of the deubiquitinating enzyme CYLD (also known as deubiquitinase), or a combination thereof, under conditions effective to treat or prevent the hemorrhagic condition in the patient.

As shown in FIG. 1, PAI-1 is the principal inhibitor of tissue plasminogen activator ("tPA") and urokinase ("uPA"), the activators of plasminogen and hence fibrinolysis (the physiological breakdown of blood clots). The present invention shows that CYLD deficiency protects mice from *S. pneumoniae* pneumolysin-induced lung hemorrhage, bacterial translocation, and lethality, thus acting as a critical negative regulator for host survival during early *S. pneumoniae* infections. The present invention also demonstrates that CYLD, highly induced by pneumo lysin, negatively regulates MKK3-p38 MAPK-dependent expression of PAI-1 in lung tissue, which in turn leads to potentiation of lung hemorrhage and increased mortality. It also provides direct evidence for the efficacy of intratracheal inoculation of recombinant PAI-1 in lung. The present invention thus unveils a novel mechanism underlying the high early mortality of *S. pneumoniae* infections and novel therapeutic strategies for reducing high early mortality in lethal *S. pneumoniae* infections. These strategies are extendible to other hemorrhagic conditions.

As used herein, the term "hemorrhagic condition" refers to any disease or disorder that involves hemorrhage in one or more tissues, regardless of the underlying cause of such hemorrhage. The cause of hemorrhage can be, for example, pathogen infection (including pathogen toxins), a foreign body, auto-immune response, or hereditary (genetic) conditions. Exemplary hemorrhagic conditions that can be treated include, without limitation, hemorrhagic pathogen infections, hereditary hemorrhagic telangiectasia ("HHT"), Goodpasture's syndrome, Wegener's granulomatosis, toxoplasmosis, and listeriosis.

Particularly preferred treatments or preventative therapies are directed to hemorrhagic lung conditions, which can result from any of the above-noted causes, but particularly pathogen infection, HHT, Goodpasture's syndrome, Wegener's granulomatosis, lung neoplasm, pulmonary embolism, toxoplasmosis, listeriosis, and hemorrhage caused by a foreign body (e.g., particulate matter capable of being inhaled and causing damage to lung tissue).

Pathogen infections that cause or contribute to hemorrhagic conditions include Gram negative bacteria, Gram positive bacteria, atypical bacteria, fungi, and parasites. Such pathogens include, without limitation, rhinovirus, parainfluenza, influenza A and B, respiratory syncytial virus, coronavirus, *Mycoplasma pneumoniae, Bordetella pertussis, Chlamydia pneumoniae*, influenza virus, adenovirus, metapneumovirus, Herpes simplex virus, cytomegalovirus ("CMV"), virulent *S. pneumoniae, Staphylococcus* spp., *Staphylococcus aureus, Haemophilus influenzae, Klebsiella* spp., *Klebsiella pneumoniae, Escherichia coli, Pseudomonas aeruginosa, Moraxella catarrhalis, Legionella pneumophila, Histoplasma capsulatum, Cryptococcus neoformans, Pneumocystis jiroveci, Coccidioides immitis, Coccidioides posadasii, Toxoplasma gondii, Strongyloides stercoralis, Ascariasis, Aspergillus* spp., *Aspergillus fumigatus, Zygomycetes* spp., *Fusarium* spp., *Mycobacterium* spp., *Mycobacterium tuberculosis, Mycobacterium bovis, Mycobacterium africanum, Mycobacterium canetti, Mycobacterium microti*, and *Yersini pestis*. Pathogen infections associated with acute bronchitis, severe pneumonia, aspergilloma, tuberculosis, bronchiectasis, coccidiodomycosis, toxoplasmosis, or listeriosis may also be treated and/or prevented according to the present method.

The patient to be treated can be a mammal who has or is at risk of developing a hemorrhagic condition. Preferably, the mammal is human, a non-human primate (e.g., chimp, orangutan, monkey, gorilla, etc.), a rodent (e.g., mouse or rat), dog, cat, horse, cow, sheep, pig, or other domesticated mammal.

By way of example, the patient to be treated can be an individual who either has deficient levels of endogenous PAI-1, endogenously produces defective PAI-1, or whose existing endogenous PAI-1 has become inhibited or inactivated or suppressed. The patient may also be an individual that otherwise should be able to produce functional PAI-1, but whose natural PAI-1 expression pathway has been interrupted, for example by bacterial toxins (e.g., pneumolysin), overexpression of CYLD, or injury caused by disease or infection.

In either acquired PAI-1 deficiency or dysfunction, PAI-1 and/or a CYLD inhibitor (and, optionally, a pneumolysin inhibitor) can be administered in a manner effective to reduce the severity of hemorrhage in the patient, and may also be administered prophylactically to such patients to prevent the onset of hemorrhage.

In either case, administration can be carried out in a manner effective to prevent onset of the hemorrhagic condition (when done before symptoms of the disorder develop), or to reduce hemorrhage (when done some time after initial onset of symptoms). Subjects at risk for a hemorrhagic condition that is caused or contributed to by aberrant CYLD or PAI-1 expression or activity can be identified by, for example, any or a combination of diagnostic or prognostic assays that are known in the art. Prophylactic administration can occur prior to the manifestation of symptoms characteristic of the aberrancy, such that a hemorrhagic condition is prevented or, alternatively, delayed in its progression.

According to one embodiment, PAI-1 is administered to the patient. Both natural and recombinant forms of PAI-1 may be used in the methods of the present invention. Preferably, the PAI-1 is a stable recombinant form, which has a longer half life than natural PAI-1. Suitable PAI-1 proteins include, e.g., GenBank Accession No. NP_000593 (wild type human), GenBank Accession No. AAA39887 (wild type mouse), CPAI (stable mutant human PAI-1, Molecular Innovations), Human Stable PAI-1 (Oxford Biomedical Research), Mouse Stable PAI-1 (Oxford Biomedical Research), Rat Stable PAI-1 (Oxford Biomedical Research), etc. Active fragments of PAI-1 can also be administered in accordance with the present invention. Gene therapy approaches can also be used to express the PAI-1 (or active fragments thereof) in affected hemorrhagic tissues, but these approaches are less preferred for non-prophylactic therapies, because the PAI-1 is active upon administration whereas the gene therapy approaches are not. The two approaches, however, can be used in combination so that a sustained increase in PAI-1 can be achieved in the affected hemorrhagic tissues.

PAI-1, when used, is preferably present in a substantially purified form (preferably at least about 80%, more preferably 90%, pure) by conventional techniques, either by isolation from cells that express the native PAI-1 protein or from recombinant host cells. Typically, the protein or polypeptide of the present invention is produced recombinantly in host cells. In such cases, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to sequential ammonium sulfate precipitation. The fraction containing the protein or polypeptide of interest can be subjected to gel filtration in an appropriately sized dextran or polyacrylamide column to separate the proteins. If necessary, the protein fraction may be further purified by HPLC.

According to a second embodiment, an inhibitor of the deubiquitinating enzyme CYLD can be administered. CYLD was initially identified as a tumor suppressor, because loss of its activity causes a benign human syndrome called cylindromatosis (Biggs et al, "The Cylindromatosis Gene (Cyld1) on Chromosome 16q May Be the Only Tumour Suppressor Gene Involved in the Development of Cylindromas," *Oncogene* 12:1375-7 (1996), which is hereby incorporated by reference in its entirety). In vitro studies have indicated that CYLD is a member of the deubiquitinating enzyme family (Bignell et al. "Identification of the Familial Cylindromatosis Tumour-suppressor Gene," *Nat. Genet.* 25:160-5 (2000); Wang et al., "The BRG1- and hBRM-associated Factor BAF57 Induces Apoptosis by Stimulating Expression of the Cylindromatosis Tumor Suppressor Gene," *Mol. Cell. Biol.* 25(18):7953-65 (2005); Saito et al., "The CAP-Gly Domain of CYLD Associates with the Proline-rich Sequence in NEMO/IKKγ," *Structure* 12(9):1719-28 (2004), each of which is hereby incorporated by reference in its entirety) that specifically digests polyubiquitin chains (Kim et al., "Deubiquitinating Enzymes as Cellular Regulators," *J. Biochem.* (Tokyo) 134: 9-18 (2003); Amerik & Hochstrasser, "Mechanism and Function of Deubiquitinating Enzymes," *Biochim. Biophys. Acta* 1695:189-207 (2004), each of which is hereby incorporated by reference in its entirety). Transfection studies have shown that CYLD deubiquitinates TRAF2 and TRAF6 and acts as a negative regulator for activation of NF-κB by tumor necrosis factor receptor and Toll-like receptor (Brummelkamp et al., "Loss of the Cylindromatosis Tumour Suppressor Inhibits Apoptosis by Activating NF-κB," *Nature* 424:797-801 (2003); Kovalenko et al., "The Tumour Suppressor CYLD Negatively Regulates NF-κB Signalling by Deubiquitination," *Nature* 424:801-5 (2003); Trompouki et al., "CYLD Is a Deubiquitinating Enzyme That Negatively Regulates NF-κB Activation by TNFR Family Members," *Nature* 424:793-6 (2003), each of which is hereby incorporated by reference in its entirety). CYLD has also been identified as a key negative regulator for NF-κB signaling, T-cell development, and tumor cell proliferation (Brummelkamp et al., "Loss of the Cylindromatosis Tumour Suppressor Inhibits Apoptosis by Activating NF-κB," *Nature* 424:797-801 (2003); Kovalenko et al., "The Tumour Suppressor CYLD Negatively Regulates NF-κB Signalling by Deubiquitination," *Nature* 424:801-5 (2003); Massoumi et al., "Cyld Inhibits Tumor Cell Proliferation by Blocking Bcl-3-dependent NF-κB Signaling," *Cell* 125:665-77 (2006); Reiley et al., "Regulation of T Cell Development by the Deubiquitinating Enzyme CYLD," *Nat. Immunol.* 7:411-7 (2006); Trompouki et al., "CYLD Is a Deubiquitinating Enzyme That Negatively Regulates NF-κB Activation by TNFR Family Members," *Nature* 424:793-6 (2003); Yoshida et al., "The Tumor Suppressor Cylindromatosis (CYLD) Acts as a Negative Regulator for Toll-like Receptor 2 Signaling via Negative Cross-talk with TRAF6 and TRAF7," *J. Biol. Chem.* 280:41111-21 (2005), each of which is hereby incorporated by reference in its entirety). CYLD is greatly induced by Gram-negative and Gram-positive bacterial pathogens (Jono et al., "NF-κB Is Essential for Induction of CYLD, the Negative Regulator of NF-κB: Evidence for a Novel Inducible Autoregulatory Feedback Pathway," *J. Biol. Chem.* 279:36171-4 (2004); Yoshida et al., "The Tumor Suppressor Cylindromatosis (CYLD) Acts as a Negative Regulator for Toll-like Receptor 2 Signaling via Negative Cross-talk with TRAF6 and TRAF7," *J. Biol. Chem.* 280: 41111-21 (2005), each of which is hereby incorporated by reference in its entirety).

Suitable inhibitors of CYLD include antibodies or antibody fragments that bind specifically to CYLD, antibody mimics that bind specifically to CYLD, nucleic acid aptamers that bind specifically to CYLD, inhibitory DNA or RNA molecules (e.g., antisense CYLD DNA or RNA, siRNA, shRNA), and expression vectors that encode the inhibitory nucleic acid molecules. Other CYLD inhibitors, whether now known or later-developed can also be employed.

Suitable anti-CYLD antibodies can be polyclonal antibodies or monoclonal antibodies, although monoclonal are preferred. The antibody may also be iso form-specific.

Various methods of producing antibodies with a known antigen are well-known to those ordinarily skilled in the art (ED HARLOW & DAVID LANE, ANTIBODIES: A LABORATORY MANUAL (1988), which is hereby incorporated by reference in its entirety). In particular, suitable antibodies may be produced by chemical synthesis, by intracellular immunization (i.e., intrabody technology), or preferably, by recombinant expression techniques. Methods of producing antibodies may further include the hybridoma technology well-known in the art.

In particular, monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. In this case, the antigen can be CYLD or an immunogenic conjugate that includes CYLD conjugated to an immunogenic toxin or the like. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Köhler & Milstein, "Continuous Cultures of Fused Cells Secreting Antibody of Predefined Specificity," *Nature* 256:495-7 (1975), which is hereby incorporated by reference in its entirety.

Mammalian lymphocytes are immunized by in vivo immunization of the animal (e.g., a mouse) with the protein or polypeptide of interest (i.e., CYLD or suitable fragments thereof). Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (see Köhler & Milstein, "Derivation of Specific Antibody-producing Tissue Culture and Tumor Lines by Cell Fusion," *Eur. J. Immunol.* 6:511-9 (1976), which is hereby incorporated by reference in its entirety). This immortal cell line (which is preferably murine, but may also be derived from cells of other mammalian species, including but not limited to rats and humans) is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of interest (e.g., CYLD or suitable fragments thereof or immunogenic conjugates that contain the same) subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbital (150 mg/Kg IV). This and other procedures for raising polyclonal antibodies are disclosed in ED HARLOW & DAVID LANE, ANTIBODIES: A LABORATORY MANUAL (1988), which is hereby incorporated by reference in its entirety.

In addition to utilizing whole antibodies, the methods of the present invention encompass use of binding portions of such antibodies. Such binding portions include Fab fragments, F(ab)2 fragments, Fab' fragments, F(ab')$_2$ fragments, Fd fragments, Fd' fragments, Fv fragments, and minibodies, e.g., 61-residue subdomains of the antibody heavy-chain variable domain (Pessi et al., "A Designed Metal-binding Protein with a Novel Fold," *Nature*, 362:367-369 (1993), which is hereby incorporated by reference in its entirety). Domain antibodies (dAbs) (see, e.g., Holt et al., "Domain Antibodies: Proteins for Therapy," *Trends Biotechnol.* 21:484-90 (2003), which is hereby incorporated by reference in its entirety) are also suitable for the methods of the present invention. These antibody fragments can be made by conventional procedures, such as proteolytic fragmentation procedures, as described in J. GODING, MONOCLONAL ANTIBODIES: PRINCIPLES AND PRACTICE 98-118 (1984), which is hereby incorporated by reference in its entirety.

Further, single chain antibodies are also suitable for the present invention (e.g., U.S. Pat. Nos. 5,476,786 to Huston and 5,132,405 to Huston & Oppermann; Huston et al., "Protein Engineering of Antibody Binding Sites: Recovery of Specific Activity in an Anti-digoxin Single-chain Fv Analogue Produced in *Escherichia coli*," *Proc. Nat'l Acad. Sci. USA* 85:5879-83 (1988); U.S. Pat. No. 4,946,778 to Ladner et al.; Bird et al., "Single-chain Antigen-binding Proteins," *Science* 242:423-6 (1988); Ward et al., "Binding Activities of a Repertoire of Single Immunoglobulin Variable Domains Secreted from *Escherichia coli*," *Nature* 341:544-6 (1989), each of which is hereby incorporated by reference in its entirety). Single chain antibodies are formed by linking the heavy and light immunoglobulin chain fragments of the Fv region via an amino acid bridge, resulting in a single chain polypeptide. Univalent antibodies are also embraced by the present invention.

As noted above, the antibodies or fragments thereof are intended to be administered in vivo. Antibodies can be produced in recombinant systems in which the appropriate cell lines are transformed, transfected, infected, or transduced with appropriate antibody-encoding DNA. Alternatively, the antibodies can be constructed by biochemical reconstitution of purified heavy and light chains.

The antibodies may be from humans, or from animals other than humans, preferably mammals, such as rat, mouse, guinea pig, rabbit, goat, sheep, and pig, or avian species such as chicken. Preferred are mouse monoclonal antibodies and antigen-binding fragments or portions thereof. In addition, chimeric antibodies and hybrid antibodies are embraced by the present invention. Techniques for the production of chimeric antibodies are described in, e.g., Morrison et al., "Chimeric Human Antibody Molecules: Mouse Antigen-binding Domains with Human Constant Region Domains," *Proc. Nat'l Acad. Sci. USA* 81:6851-5 (1984), Neuberger et al., "Recombinant Antibodies Possessing Novel Effector Functions," *Nature* 312:604-8 (1984), and Takeda et al., "Construction of Chimaeric Processed Immunoglobulin Genes Containing Mouse Variable and Human Constant Region Sequences," *Nature* 314:452-4 (1985), each of which is hereby incorporated by reference in its entirety. For human therapeutic purposes, humanized antibodies or fragments can be used.

Antibodies and antibody fragments that bind to and inhibit activity of CYLD may be identified using known screening assays, such as those described in U.S. Patent Application Publication No. 2006/0105344 to Bernards et al., which is hereby incorporated by reference in its entirety.

Exemplary antibodies that bind specifically to CYLD include, without limitation, mouse monoclonal antibody clones 1E9, 2C3, 2F9, 2G1 and 3A9 (all directed to human CYLD and available from Abnova Corp.); as well as mono-specific polyclonal antiserum and polyclonal antiserum (e.g., ab33929 and ab38320, both available from Abcam).

Antibody mimics that specifically bind to and inhibit CYLD can also be administered. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J. Mol. Biol.* 284:1141-1151 (1998); Koide et al., "Probing Protein Conformational Changes in Living Cells by Using Designer Binding Proteins: Application to the Estrogen Receptor," *Proc. Nat'l Acad. Sci. USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol.* 15(8):772-777 (1997), which is hereby incorporated by reference in its entirety). Variations in these antibody mimics can be created by substituting one or more domains of these polypeptides and then screening the modified monobodies or affibodies for CYLD binding and inhibitory activity. These antibody mimics can be delivered using similar strategies as described for antibody delivery.

Exemplary nucleic acids include nucleic aptamers (described in greater detail below) such as the dimer or di-dimer or multimer aptabodies described in PCT Publication No. WO/2005/106035 to Shi & L is, which is hereby incorporated by reference in its entirety. These aptamers, which are also antibody mimics, can be screened for activity as a CYLD inhibitor using known screening assays, such as those described in U.S. Patent Application Publication No. 2006/0105344 to Bernards et al., which is hereby incorporated by reference in its entirety.

Other suitable therapeutic nucleic acid molecules also include aptamers that specifically bind to and inhibit CYLD activity. This is intended to encompass aptamers that, from a structural perspective, are not necessarily considered antibody mimics. Aptamers are single-stranded, partially single-stranded, partially double-stranded, or double-stranded nucleotide sequences, advantageously a replicatable nucleotide sequence, capable of specifically recognizing a selected non-oligonucleotide molecule or group of molecules by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides, and nucleotides comprising backbone modifications, branchpoints, and non-nucleotide residues, groups, or bridges. Aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence.

Nucleic acid aptamers include multivalent aptamers and bivalent aptamers. Methods of making bivalent and multivalent aptamers and their expression in multi-cellular organisms are described in U.S. Pat. No. 6,458,559 to Shi & L is, which is hereby incorporated by reference in its entirety. A method for modular design and construction of multivalent nucleic acid aptamers, their expression, and methods of use are described in U.S. Patent Application Publication No. 2005/0282190 to Shi et al., which is hereby incorporated by reference in its entirety. Aptamers may be designed to inhibit expression of CYLD and/or to bind to and inhibit activity of CYLD.

Identifying suitable nucleic acid aptamers that inhibit CYLD expression basically involves selecting aptamers that bind CYLD mRNA with sufficiently high affinity (e.g., $K_d$=20-50 nM) and specificity from a pool of nucleic acids containing a random region of varying or predetermined length (Shi et al., "A Specific RNA Hairpin Loop Structure Binds the RNA Recognition Motifs of the *Drosophila* SR Protein B52," *Mol. Cell. Biol.* 17(5):2649-57 (1997); Shi, "Perturbing Protein Function with RNA Aptamers" (1997) (Ph.D. dissertation, Cornell University) (University Microfilms, Inc.), each of which is hereby incorporated by reference in its entirety).

For example, identifying suitable nucleic acid aptamers can be carried out using an established in vitro selection and amplification scheme known as SELEX. The SELEX scheme is described in detail in U.S. Pat. No. 5,270,163 to Gold & Tuerk, Ellington & Szostak, "In Vitro Selection of RNA Molecules That Bind Specific Ligands," *Nature* 346:818-22 (1990), and Tuerk & Gold, "Systematic Evolution of Ligands by Exponential Enrichment: RNA Ligands to Bacteriophage T4 DNA Polymerase," *Science* 249:505-10 (1990), each of which is hereby incorporated by reference in its entirety. The SELEX procedure can be modified so that an entire pool of aptamers with binding affinity can be identified by selectively partitioning the pool of aptamers. This procedure is described in U.S. Patent Application Publication No. 2004/0053310 to Shi et al., which is hereby incorporated by reference in its entirety.

Aptamers that bind to and inhibit activity of CYLD may be identified using known screening assays, such as those described in U.S. Patent Application Publication No. 2006/0105344 to Bernards et al., which is hereby incorporated by reference in its entirety.

Inhibitory RNA molecules include antisense nucleic acids that are capable of interfering with expression of endogenous CYLD. Antisense nucleic acids are DNA or RNA molecules, oligoribonucleotides, or oligodeoxyribonucleotides that are complementary to at least a portion of a specific mRNA molecule (Weintraub, "Antisense RNA and DNA," *Sci. Am.* 262:40-6 (1990), which is hereby incorporated by reference in its entirety). In the cell, the antisense nucleic acids are transcribed and hybridize to that specific mRNA molecule (known as the target, in this case CYLD mRNA). The specific hybridization of an antisense nucleic acid molecule with its target nucleic acid interferes with the normal function of the target nucleic acid. The functions of DNA to be interfered with include replication and transcription. The functions of RNA to be interfered with include all vital functions, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is the regulation of protein expression.

In this aspect of the present invention, expression of endogenous CYLD may be downregulated using an RNA-based form of gene-silencing known as RNA-interference (RNAi) (also known more recently as siRNA for short, interfering RNAs). RNAi is a form of post-transcriptional gene silencing ("PTGS"). PTGS is the silencing of an endogenous gene caused by the introduction of a homologous double-stranded RNA ("dsRNA"), transgene, or virus. In PTGS, the transcript of the silenced gene is synthesized, but does not accumulate because it is degraded. RNAi is a specific form of PTGS, in which gene silencing is induced by the direct introduction of dsRNA. Numerous reports have been published on critical advances in the understanding of the biochemistry and genetics of both gene silencing and RNAi (Matzke et al., "RNA-based Silencing Strategies in Plants," *Curr. Opin. Genet. Dev.* 11(2):221-7 (2001); Hammond et al., "Post-transcriptional Gene Silencing by Double-stranded RNA," *Nature Rev. Gen.* 2:110-9 (2001); Hamilton & Baulcombe, "A Species of Small Antisense RNA in Posttranscriptional Gene Silencing in Plants," *Science* 286:950-2 (1999); Hammond et al., "An RNA-directed Nuclease Mediates Post-transcriptional Gene Silencing in *Drosophila* Cells," *Nature* 404:293-6 (2000); Hutvágner & Zamore, "RNAi: Nature Abhors a Double-strand," *Curr. Opin. Gen. Devel.* 12:225-32 (2002), each of which is hereby incorporated by reference in its entirety). In RNAi, the introduction of dsRNA into animal cells leads to the destruction of the endogenous, homologous mRNA, phenocopying a null mutant for that specific gene. In siRNA, the dsRNA is processed in vivo to short interfering molecules of 21-, 22- or 23-nucleotide RNAs (siRNA), which are also called "guide RNAs" (Hammond et al., "Post-transcriptional Gene Silencing by Double-stranded RNA," *Nature Rev. Gen.* 2:110-9 (2001); Sharp, "RNA Interference—2001," *Genes Dev.* 15:485-90 (2001); Hutvágner & Zamore, "RNAi: Nature Abhors a Double-strand," *Curr. Opin. Gen. Devel.* 12:225-32 (2002), each of which is hereby incorporated by reference in its entirety), by the Dicer enzyme, which is a member of the RNAse III-family of dsRNA-specific ribonucleases (Hutvágner & Zamore, "RNAi: Nature Abhors a Double-strand," *Curr. Opin. Gen. Devel.* 12:225-32 (2002); Bernstein et al., "Role for a Bidentate Ribonuclease in the Initiation Step of RNA Interference," *Nature* 409:363-6 (2001); Tuschl, "RNA Interference and Small Interfering RNAs," *Chembiochem.* 2:239-45 (2001); Zamore et al., "RNAi: Double-stranded RNA Directs the ATP-dependent Cleavage of mRNA at 21 to 23 Nucleotide Intervals," *Cell* 101:25-33 (2000); U.S. Pat. No. 6,737,512 to Wu & Crooke, each of which is hereby incorporated by reference in its entirety). Successive cleavage events degrade the RNA to 19-21 by duplexes, each with 2-nucleotide 3' overhangs (Hutvágner & Zamore, "RNAi: Nature Abhors a Double-strand," *Curr. Opin. Gen. Devel.* 12:225-32 (2002); Bernstein et al., "Role for a Bidentate Ribonuclease in the Initiation Step of RNA Interference," *Nature* 409:363-6 (2001), each of which is hereby incorporated by reference in its entirety). The siRNAs are incorporated into an effector known as the RNA-induced silencing complex, which targets the homologous endogenous transcript by base pairing interactions and cleaves the mRNA approximately 12 nucleotides from the 3' terminus of the siRNA (Hammond et al., "Post-transcriptional Gene Silencing by Double-stranded RNA," *Nature Rev. Gen.* 2:110-9 (2001); Sharp, "RNA Interference—2001," Genes Dev. 15:485-90 (2001); Hutvágner & Zamore, "RNAi: Nature Abhors a Double-strand," *Curr. Opin. Gen. Devel.* 12:225-32 (2002); Nykänen et al., "ATP Requirements and Small Interfering RNA Structure in the RNA Interference Pathway," *Cell* 107:309-21 (2001), each of which is hereby incorporated by reference in its entirety).

There are several methods for preparing siRNA, including chemical synthesis, in vitro transcription, siRNA expression vectors, and PCR expression cassettes. In one aspect of the present invention, dsRNA can be generated by transcription in vivo. This involves preparing a nucleic acid molecule for the production of dsRNA, inserting the nucleic acid molecule into a suitable expression vector having the appropriate 5' and 3' regulatory nucleotide sequences operably linked for transcription and translation, and introducing the expression vector having the nucleic acid molecule into a suitable host or subject. For in vitro transcription, complementary sense and antisense RNAs derived from a substantial portion of the coding region of the CYLD nucleic acid molecule are synthesized in vitro (Fire et al., "Potent and Specific Genetic Interference by Double-stranded RNA in *Caenorhabditis elegans*," *Nature* 391:806-11 (1998); Timmons & Fire, "Specific Interference by Ingested dsRNA," *Nature* 395:854 (1998); Montgomery et al., "RNA as a Target of Double-stranded RNA-mediated Genetic Interference in *Caenorhabditis elegans*," *Proc. Nat'l Acad. Sci. USA* 95:15502-7; Tabara et al., "RNAi in *C. elegans*: Soaking in the Genome Sequence," *Science* 282:430-1 (1998), each of which is hereby incorporated by reference in its entirety). The resulting sense and antisense RNAs are annealed in an injection buffer, and dsRNA is administered to the subject using any method of administration described herein.

Using siRNA for gene silencing is a rapidly evolving tool in molecular biology, and guidelines are available in the literature for designing highly effective siRNA targets and making antisense nucleic acid constructs for inhibiting endogenous protein (U.S. Pat. No. 6,737,512 to Wu & Crooke; Brown et al., "RNA Interference in Mammalian Cell Culture: Design, Execution, and Analysis of the siRNA Effect," *Ambion TechNotes* 9(1):3-5 (2002); Sui et al., "A DNA Vector-based RNAi Technology to Suppress Gene Expression in Mammalian Cells," *Proc. Nat'l Acad. Sci. USA* 99(8):5515-20 (2002); Yu et al., "RNA Interference by Expression of Short-interfering RNAs and Hairpin RNAs in Mammalian Cells," *Proc. Nat'l Acad. Sci. USA* 99(9):6047-52 (2002); Paul et al., "Effective Expression of Small Interfering RNA in Human Cells," *Nat. Biotechnol.* 20:505-8 (2002); Brummelkamp et al., "A System for Stable Expression of Short Interfering RNAs in Mammalian Cells," *Science* 296:550-3 (2002), each of which is hereby incorporated by reference in its entirety). There are also commercially available sources for custom-made siRNAs, which can be custom-designed via algorithms accessible from the company's Internet services, such as those offered by GenScript Corp., Promega Corp., Ambion Inc., and ThermoFisher Inc. (via Dharmacon subsidiary).

Exemplary anti-CYLD siRNA (sense strand) include, without limitation,

```
(i)      aaguaccgaagggaaguauag;    (SEQ ID NO: 1)

(ii)     cgaagaggctgaatcataa;      (SEQ ID NO: 2)

(iii)    cgctgtaactctttagcat;      (SEQ ID NO: 3)

(iv)     gaactcacatggtctagaa;      (SEQ ID NO: 4)
and (v)      gcagagtcctaacgttgca.      (SEQ ID NO: 5)
```

These siRNA are described in Reiley et al., "Regulation of the Deubiquitinating Enzyme CYLD by IκB Kinase Gamma-dependent Phosphorylation," *Mol. Cell. Biol.* 25(10):3886-95 (2005), and Stegmeier et al., "The Tumor Suppressor CYLD Regulates Entry into Mitosis," *Proc. Nat'l Acad. Sci. USA* 104(21): 8869-74 (2007), each of which is hereby incorporated by reference in its entirety).

Exemplary anti-CYLD shRNA include, without limitation,

```
                                              (SEQ ID NO: 6)
(i)
cctcatgcagttctctttgttcaagagacaaagagaactgcatgagg;

(SEQ ID NO: 7)
(ii)
gaatgccgacctacaaagattcaagagatctttgtaggtcggcattc;

(SEQ ID NO: 8)
(iii)
cagttatattctgtgatgtttcaagagaacatcacagaatataactg;

(SEQ ID NO: 9)
(iv)
gaggtgttggggacaaaggttcaagagacctttgtcccaacacctc;
and (SEQ ID NO: 10)
(v)
gtgggctcattggctgaagttcaagagacttcagccaatgagcccac.
```

These shRNA are described in Kovalenko et al., "The Tumour Suppressor CYLD Negatively Regulates NF-κB Signalling by Deubiquitination," *Nature* 424:801-5 (2003), and Brummelkamp et al., "Loss of the Cylindromatosis Tumour Suppressor Inhibits Apoptosis by Activating NF-κB," *Nature* 424:797-801 (2003), each of which is hereby incorporated by reference in its entirety).

Additional RNAi agents are commercially available, including CYLD siRNA, SC-37326 (Santa Cruz Biotechnology); and CYLD shRNA, TR305137 (Origene) and NM-015247 (Sigma-Aldrich).

Optionally, PAI-1 and/or a CYLD inhibitor may be administered. In addition, other therapeutic agents can be administered with PAI-1 and/or the CYLD inhibitor, or combination thereof. The other therapeutic agents can be used to treat the underlying cause of the hemorrhagic condition or as a further therapeutic designed to reduce the severity or completely inhibit further hemorrhage in affected tissues or organs. One example of these other therapeutic agents is an inhibitor of a cholesterol-dependent cytolysin (e.g., pneumolysin, mitilysin, intermedilysin, vaginolysin, lectinolysin, suilysin, hemolysin, tetanolysin, listeriolysin, streptolysin, anthrolysin, etc.). Although any inhibitor of cholesterol-dependent cytolysin can be utilized in the present invention, exemplary inhibitors include, without limitation, cholesterol (Marquart et al., "Cholesterol as Treatment for Pneumococcal Keratitis: Cholesterol-specific Inhibition of Pneumolysin in the Cornea," *Invest. Opthalmol. Vis. Sci.* 48:2661-6 (2007), which is hereby incorporated by reference in its entirety), as well as Rac1-specific and Rho-associated kinase-specific inhibitors (Iliev et al., "Cholesterol-dependent Actin Remodeling via RhoA and Rac1 Activation by the *Streptococcus pneumoniae* Toxin Pneumolysin," *Proc. Nat'l Acad. Sci. USA* 104(8): 2897-902 (2007), which is hereby incorporated by reference in its entirety).

The methods of the present invention are intended to be carried out by administering the active therapeutic agents alone or in combination with one another, but preferably in the form of one or more pharmaceutical compositions that include a pharmaceutically acceptable carrier for the therapeutic agent(s).

As will be apparent to one of ordinary skill in the art, administering may be carried out using generally known methods. Typically, the agent is administered by introducing the agent into the subject. In some embodiments, for example when a polypeptide agent (e.g., PAI-1) is used, the agent may be administered by introducing into the subject a nucleic acid molecule that encodes the polypeptide (JOSEPH SAMBROOK & DAVID W. RUSSELL, 1 MOLECULAR CLONING: A LABORATORY MANUAL (3d ed. 2001); SHORT PROTOCOLS IN MOLECULAR BIOLOGY (Frederick M. Ausubel et al. eds., 1999); U.S. Pat. No. 4,237,224 to Cohen & Boyer, each of which is hereby incorporated by reference in its entirety).

Administration can be accomplished either via systemic administration to the subject or via targeted administration to affected cells. Exemplary routes of administration include, without limitation, by intratracheal inoculation, aspiration, airway instillation, aerosolization, nebulization, intranasal instillation, oral or nasogastric instillation, intraperitoneal injection, intravascular injection, topically, transdermally, parenterally, subcutaneously, intravenous injection, intra-arterial injection (such as via the pulmonary artery), intramuscular injection, intrapleural instillation, intraventricularly, intralesionally, by application to mucous membranes (such as that of the nose, throat, and/or bronchial tubes), or implantation of a sustained release vehicle adjacent to the affected tissue. In the case of hemorrhagic lung conditions, administration is preferably via intratracheal inoculation, aspiration, airway instillation, aerosolization, or nebulization.

Typically, the therapeutic agent (i.e., PAI-1, CYLD inhibitor, pneumolysin inhibitor) will be administered to a mammal as a pharmaceutical formulation that includes the therapeutic agent and any pharmaceutically acceptable suitable adjuvants, carriers, excipients, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of therapeutic agent together with the adjuvants, carriers and/or excipients. The amount of active compound in such therapeutically useful compositions is such that a suitable dosage unit will be obtained.

The agents may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of the agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient(s), sucrose as a sweetening agent, methyl and propylparabens as preservatives, a dye, and flavoring such as cherry or orange flavor.

The agents may also be administered parenterally. Solutions or suspensions of the agent can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents according to this aspect of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

As another alternative, the agents of the present invention may be administered to the airways in the form of a lung surfactant formulation. The lung surfactant formulation can include exogenous lung surfactant formulations (e.g., Infasurf® (Forest Laboratories), Survanta® (Ross Products), and Curosurf® (DEY, Calif., USA) or synthetic lung surfactant formulations (e.g., Exosurf® (GlaxoWellcome Inc.) and ALEC). These surfactant formulations are typically administered via airway instillation (i.e., after intubation) or intratracheally.

The agents of the present invention may be administered directly to the targeted tissue. Additionally and/or alternatively, the agent may be administered to a non-targeted area along with one or more agents that facilitate migration of the agent to (and/or uptake by) a targeted tissue, organ, or cell. While the targeted tissue can be any tissue subject to hemorrhagic conditions, a preferred target tissue is lung tissue. As will be apparent to one of ordinary skill in the art, the therapeutic agent itself be modified to facilitate its transport to (and uptake by) the desired tissue, organ, or cell. For example, PAI-1 and CYLD inhibitors can be modified as described above to facilitate their transport to a target cell, organ (e.g., lung), and/or tissue (e.g., lung tissue), including its transport across the blood-brain barrier; and/or its uptake by the target cell (e.g., its transport across cell membranes).

Exemplary delivery devices include, without limitation, nebulizers, atomizers, liposomes, transdermal patches, implants, implantable or injectable protein depot compositions, syringes, and gene therapy. Other delivery systems which are known to those of skill in the art can also be employed to achieve the desired delivery of the therapeutic agent to the desired organ, tissue, or cells in vivo to carry out this aspect of the present invention.

Any suitable approach for delivery of the agents can be utilized to practice this aspect of the present invention. Typically, the agent will be administered to a patient in a vehicle that delivers the agent(s) to the target cell, tissue, or organ.

One approach for delivering agents into cells involves the use of liposomes (including the surfactant formulations described above). Basically, this involves providing a liposome which includes agent(s) to be delivered, and then contacting the target cell, tissue, or organ with the liposomes under conditions effective for delivery of the agent into the cell, tissue, or organ.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner where the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., Wang & Huang, "pH-Sensitive Immunoliposomes Mediate Target-cell-specific Delivery and Controlled Expression of a Foreign Gene in Mouse," *Proc. Nat'l Acad. Sci. USA* 84:7851-5 (1987), which is hereby incorporated by reference in its entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane, which enzyme slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., "Diffusion of Univalent Ions Across the Lamellae of Swollen Phospholipids," *J. Mol. Biol.* 13:238-52 (1965), U.S. Pat. No. 5,653,996 to Hsu, U.S. Pat. No. 5,643,599 to Lee et al., U.S. Pat. No. 5,885,613 to Holland et al., U.S. Pat. No. 5,631,237 to Dzau & Kaneda, and U.S. Pat. No. 5,059,421 to Loughrey et al., each of which is hereby incorporated by reference in its entirety.

These liposomes can be produced such that they contain, in addition to the therapeutic agents of the present invention, other therapeutic agents, such as anti-inflammatory agents, which would then be released at the target site (e.g., Wolff et al., "The Use of Monoclonal Anti-Thy1 IgG1 for the Targeting of Liposomes to AKR-A Cells in Vitro and in Vivo," *Biochim. Biophys. Acta* 802:259-73 (1984), which is hereby incorporated by reference in its entirety).

An alternative approach for delivery of proteins or polypeptide agents (e.g., PAI-1) involves the conjugation of the desired protein or polypeptide to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of proteins or polypeptide agents involves preparation of chimeric proteins according to U.S. Pat. No. 5,817,789 to Heartlein et al., which is hereby incorporated by reference in its entirety. The chimeric protein can include a ligand domain and the polypeptide agent (e.g., PAI-1). The ligand domain is specific for receptors located on a target cell. Thus, when the chimeric protein is delivered intravenously or otherwise introduced into blood or lymph, the chimeric protein will adsorb to the targeted cell, and the targeted cell will internalize the chimeric protein.

Nucleic acid agents (including RNA and DNA) for use in the methods of the present invention can be delivered to a subject in a number of ways known in the art, including through the use of gene therapy vectors and methods as described above. The nucleic acid can be contained within a vector that can be one useful in gene therapy, for example, a vector that can be transferred to the cells of a subject and provide for expression of the therapeutic nucleic acid agent therein. Such vectors include chromosomal vectors (e.g., artificial chromosomes), non-chromosomal vectors, and synthetic nucleic acids. Vectors include plasmids, viruses, and phages, such as retroviral vectors, lentiviral vectors, adenoviral vectors, and adeno-associated vectors.

Nucleic acid agents can be transferred into a subject using ex vivo or in vivo methods. Ex vivo methods involve transfer of the nucleic acid into cells in vitro (e.g., by transfection, infection, or injection) that are then transferred into or administered to the subject. The cells can be, for example, cells derived from the subject (e.g., lymphocytes) or allogeneic cells. For example, the cells can be implanted directly into a specific tissue of the subject or implanted after encapsulation within an artificial polymer matrix. Examples of sites of implantation include the lungs or airways, skin, conjunctiva, central nervous system, peripheral nerve, a grafted kidney, or an inflamed joint. Nucleic acids can also be delivered into a subject in vivo. For example, nucleic acids can be administered in an effective carrier, e.g., any formulation or composition capable of effectively delivering the nucleic acid to cells in vivo. Nucleic acids contained within viral vectors can be delivered to cells in vivo by infection or transduction using virus. Nucleic acids and vectors can also be delivered to cells by physical means, e.g., by electroporation, lipids, cationic lipids, liposomes, DNA gun, calcium phosphate precipitation, injection, or delivery of naked nucleic acid.

As an alternative to non-infective delivery of nucleic acids as described above, naked DNA or infective transformation vectors can be used for delivery, whereby the naked DNA or infective transformation vector contains a recombinant gene that encodes the inhibitory RNA capable of inhibiting expression of CYLD (in the case of administering an inhibitor of CYLD), or a recombinant gene that encodes PAI-1 (in the case of administering PAI-1). The nucleic acid molecule is then expressed in the transformed cell.

The recombinant gene includes, operatively coupled to one another, an upstream promoter operable in mammalian cells and optionally other suitable regulatory elements (i.e., enhancer or inducer elements), a coding sequence that encodes the therapeutic nucleic acid (described above), and a downstream transcription termination region. Any suitable constitutive promoter or inducible promoter can be used to regulate transcription of the recombinant gene, and one of skill in the art can readily select and utilize such promoters, whether now known or hereafter developed. The promoter can also be specific for expression in cells that express CYLD. Tissue specific promoters can also be made inducible/repressible using, e.g., a TetO response element. Other inducible elements can also be used. Known recombinant techniques can be utilized to prepare the recombinant gene, transfer it into the expression vector (if used), and administer the vector or naked DNA to a patient. Exemplary procedures are described in SAMBROOK & RUSSELL, MOLECULAR CLONING: A LABORATORY MANUAL (2d ed. 1989), which is hereby incorporated by reference in its entirety. One of skill in the art can readily modify these procedures, as desired, using known variations of the procedures described therein.

Any suitable viral or infective transformation vector can be used. Exemplary viral vectors include, without limitation, adenovirus, adeno-associated virus, and retroviral vectors (including lentiviral vectors).

Adenovirus gene delivery vehicles can be readily prepared and utilized given the disclosure provided in Berkner, "Development of Adenovirus Vectors for the Expression of Heterologous Genes," *Biotechniques* 6:616-29 (1988), Rosenfeld et al., "Adenovirus-mediated Transfer of a Recombinant α1-antitrypsin Gene to the Lung Epithelium in Vivo," *Science* 252:431-434 (1991), PCT Publication No. WO/1993/007283 to Curiel et al., PCT Publication No. WO/1993/006223 to Perricaudet et al., and PCT Publication No. WO/1993/007282 to Curiel et al., each of which is hereby incorporated by reference in its entirety. Additional types of adenovirus vectors are described in U.S. Pat. No. 6,057,155 to Wickham et al., U.S. Pat. No. 6,033,908 to Bout & Hoeben, U.S. Pat. No. 6,001,557 to Wilson et al., U.S. Pat. No. 5,994,132 to Chamberlain & Kumar-Singh, U.S. Pat. No. 5,981,225 to Kochanek & Schniedner, U.S. Pat. No. 5,885,808 to Spooner & Epenetos, and U.S. Pat. No. 5,871,727 to Curiel, each of which is hereby incorporated by reference in its entirety.

Adeno-associated viral gene delivery vehicles can be constructed and used to deliver into cells a recombinant gene encoding a desired nucleic acid. The use of adeno-associated viral gene delivery vehicles in vitro is described in Chatterjee et al., "Dual-target Inhibition of HIV-1 in Vitro by Means of an Adeno-associated Virus Antisense Vector," *Science* 258:1485-8 (1992), Walsh et al., "Regulated High Level Expression of a Human γ-Globin Gene Introduced into Erythroid Cells by an Adeno-associated Virus Vector," *Proc. Nat'l Acad. Sci. USA* 89:7257-61 (1992), Walsh et al., "Phenotypic Correction of Fanconi Anemia in Human Hematopoietic Cells with a Recombinant Adeno-associated Virus Vector," *J. Clin. Invest.* 94:1440-8 (1994), Flotte et al., "Expression of the Cystic Fibrosis Transmembrane Conductance Regulator from a Novel Adeno-associated Virus Promoter," *J. Biol. Chem.* 268:3781-90 (1993); Ponnazhagan et al., "Suppression of Human α-Globin Gene EXPRESSION Mediated by the Recombinant Adeno-associated Virus 2-based Antisense Vectors," *J. Exp. Med.* 179:733-8 (1994), Miller et al., "Recombinant Adeno-associated Virus (rAAV)-mediated Expression of a Human γ-Globin Gene in Human Progenitor-derived Erythroid Cells," *Proc. Nat'l Acad. Sci. USA* 91:10183-7 (1994), Einerhand et al., "Regulated High-level Human β-Globin Gene Expression in Erythroid Cells Following Recombinant Adeno-associated Virus-mediated Gene Transfer," *Gene Ther.* 2:336-43 (1995), Luo et al., "Adeno-associated Virus 2-mediated Gene Transfer and Functional Expression of the Human Granulocyte-macrophage Colony-stimulating Factor," *Exp. Hematol.* 23:1261-7 (1995), and Zhou et al., "Adeno-associated Virus 2-mediated Transduction and Erythroid Cell-specific Expression of a Human β-Globin Gene," *Gene Ther.* 3:223-9 (1996), each of which is hereby incorporated by reference in its entirety. In vivo use of these vehicles is described in Flotte et al., "Stable in Vivo Expression of the Cystic Fibrosis Transmembrane Conductance Regulator with an Adeno-associated Virus Vector," *Proc. Nat'l Acad. Sci. USA* 90:10613-7 (1993), and Kaplitt et al., "Long-term Gene Expression and Phenotypic Correction Using Adeno-associated Virus Vectors in the Mammalian Brain," *Nat. Genet.* 8:148-54 (1994), each of which is hereby incorporated by reference in its entirety.

Retroviral vectors which have been modified to form infective transformation systems can also be used to deliver a recombinant gene encoding a desired nucleic acid product into a target cell. One such type of retroviral vector is disclosed in U.S. Pat. No. 5,849,586 to Kriegler & Perez, which is hereby incorporated by reference in its entirety. Lentivirus vectors can also be utilized, including those described in U.S. Pat. No. 6,790,657 to Arya, U.S. Patent Application Publication No. 2004/0170962 to Kafri et al., and U.S. Patent Application Publication No. 2004/0147026 to Arya, each of which is hereby incorporated by reference in its entirety.

Inhibitory RNA can be administered to the subject systemically or locally as described above. Delivery of inhibitory RNA is preferably administered alone or as a component of a composition of the present invention. Suitable compositions include the siRNA formulated or complexed with polyethylenimine (e.g., linear or branched PEI) and/or polyethylenimine derivatives, including for example grafted PEIs such as galactose PEI, cholesterol PEI, antibody derivatized PEI, and polyethylene glycol PEI derivatives thereof (see, e.g., Blazek-Welsh & Rhodes, "Maltodextrin-based Proniosomes," *AAPS Pharm. Sci.* 3(1):1-11 (2001); Furgeson et al., "Modified Linear Polyethylenimine-cholesterol Conjugates for DNA Complexation," *Bioconjug. Chem.* 14:840-7 (2003); Kunath et al., "The Structure of PEG-modified Poly(Ethylene Imines) Influences Biodistribution and Pharmacokinetics of Their Complexes with NF-κB Decoy in Mice," *Pharm. Res.* 19:810-7 (2002); Choi et al., "Effect of Poly(Ethylene Glycol) Grafting on Polyethylenimine as a Gene Transfer Vector in Vitro," *Bull. Korean Chem. Soc.* 22(1):46-52 (2001); Bettinger et al., "Size Reduction of Galactosylated PEI/DNA Complexes Improves Lectin-mediated Gene Transfer into Hepatocytes," *Bioconjug. Chem.* 10:558-61 (1999); Petersen et al., "Polyethylenimine-graft-poly(ethylene glycol) Copolymers: Influence of Copolymer Block Structure on DNA Complexation and Biological Activities as Gene Delivery System," *Bioconjug. Chem.* 13:845-54 (2002); Erbacher et al., "Transfection and Physical Properties of Various Saccharide, Poly(Ethylene Glycol), and Antibody-derivatized Polyethylenimines (PEI)," *J. Gene Med.* 1(3):210-22 (1999); Godbey et al., "Tracking the Intracellular Path of Poly(Ethylenimine)/DNA Complexes for Gene Delivery," *Proc. Nat'l Acad. Sci. USA* 96:5177-81 (1999); Godbey et al., "Poly (Ethylenimine) and Its Role in Gene Delivery," *J. Control. Release* 60:149-60 (1999); Diebold et al., "Mannose Polyethylenimine Conjugates for Targeted DNA Delivery into Dendritic Cells," *J. Biol. Chem.* 274:19087-94 (1999); Thomas & Klibanov, "Enhancing Polyethylenimine's Delivery of Plasmid DNA into Mammalian Cells," *Proc. Nat'l Acad. Sci. USA* 99:14640-5 (2002); U.S. Pat. No. 6,586,524 to Sagara, each of which is hereby incorporated by reference in its entirety).

The inhibitory RNA molecule can also be present in the form of a bioconjugate, for example a nucleic acid conjugate as described in U.S. Pat. No. 6,528,631 to Cook et al., U.S. Pat. No. 6,335,434 to Guzaev et al., U.S. Pat. No. 6,235,886 to Manoharan & Cook, U.S. Pat. No. 6,153,737 to Manoharan et al., U.S. Pat. No. 5,214,136 to Lin & Matteucci, and U.S. Pat. No. 5,138,045 to Cook & Guinosso, each of which is hereby incorporated by reference in its entirety.

The inhibitory RNA, or any composition or bioconjugate containing the same, can be administered via a liposomal delivery mechanism described above.

Many routes of delivery are known to the skilled artisan for delivery of anti-target antibodies. For example, direct injection may be suitable for delivering the antibody to the site of interest. It is also possible to utilize liposomes with antibodies in their membranes to specifically deliver the liposome to the area where CYLD expression or activity is to be inhibited. These liposomes can be produced such that they contain, in addition to monoclonal antibody, other therapeutic agents, such as those described above, which would then be released at the target site.

Administration can be carried out as frequently as required and for a duration that is suitable to provide effective treatment for the hemorrhagic condition being treated or prevented. For example, administration can be carried out with a single sustained-release dosage formulation or with multiple daily doses. Where more than one of PAI-1, a CYLD inhibitor, and a pneumolysin inhibitor are administered, they may be administered at the same time (e.g., present in the same pharmaceutical formulation), or separately (e.g., each present in a separate pharmaceutical formulation) but during the same course of treatment. Administration can be carried out before, concurrently with, and/or after the appearance of symptoms of the hemorrhagic condition.

The amount to be administered will, of course, vary depending upon the treatment regimen. Generally, an agent is administered to achieve an amount effective for amelioration of, or prevention of the development of symptoms of, the hemorrhagic condition (i.e., a therapeutically effective amount). Thus, a therapeutically effective amount can be an amount which is capable of at least partially preventing or reversing the hemorrhagic condition. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based on in vivo animal studies. A therapeutically effective amount can be determined empirically by those of skill in the art.

By way of example, PAI-1 can be administered in an amount between about 500 µg/kg and about 2.5 mg/kg, preferably between about 750 µg/kg and about 2.25 mg/kg, more preferably between about 1 mg/kg and 2 mg/kg. Inhibitors of CYLD can be administered in an amount between about 500 µg/kg and about 10 mg/kg, preferably between about 750 µg/kg and about 5 mg/kg. In the case of CYLD siRNA, the amount is preferably between about 25 nmol/kg and 10 mmol/kg, more preferably between about 100 nmol/kg and about 5 mmol/kg.

EXAMPLES

The following Examples are intended to illustrate, but by no means are intended to limit, the scope of the present invention as set forth in the appended claims.

Example 1

Reagents and Antibodies

SB203580, Wedelolactone, mouse recombinant PAI-1 (rPAI-1), and mouse α-PAI-1 neutralizing antibody MA-33H1F$_7$ were purchased from Calbiochem (California, U.S.A). Antibodies anti-phospho-MKK3/6 (Ser-189/207), anti-phospho-p38 MAPK (Thr-180/Tyr-182), anti-MKK3, anti-p38MPAK, HRP-conjugated anti-mouse IgG, and HRP-conjugated anti-Rabbit IgG were purchased from Cell Signaling Technology (Massachusetts, U.S.A). Anti-β-actin antibody was from Sigma-Aldrich (Missouri, U.S.A.). Anti-CYLD polyclonal antibody is described in Jono et al., "NF-κB Is Essential for Induction of CYLD, the Negative Regulator of NF-κB: Evidence for a Novel Inducible Autoregulatory Feedback Pathway," *J. Biol. Chem.* 279:36171-4 (2004), which is hereby incorporated by reference in its entirety. Anti-PAI-1 polyclonal antibody, anti-TRAF6 antibody, and anti-ubiquitin antibody were from Santa Cruz Biotechnology.

Example 2

Bacterial Strains and Cultures, Bacterial Lysate, and Pneumolysin

Clinical isolates of *S. pneumoniae* wild type strain D39 (serotype 2) ("WT"), strain TIGR4 (serotype 4), and a D39 isogenic mutant strain deficient in the pneumolysin gene ("Ply MT") were used in the present Examples.

Bacteria were grown on chocolate agar or in Todd-Hewitt broth supplemented with 0.5% yeast extract ("THY") at 37° C. in an atmosphere of 5% $CO_2$. Stocks were maintained at −80° C. in THY plus 15% glycerol, and all cultures of each strain were grown from the same frozen stock. To determine the virulence factor(s) responsible for causing lung hemorrhage and lethality as well as for PAI-1 induction, S.p. live bacteria, lysate of both WT and Ply MT strains, and purified pneumolysin were used in all the experiments. In experiments using live bacteria, the epithelial cells were incubated with live S.p. at a concentration of 10 bacteria/cell (moi). For in vivo experiments, S.p. was intratracheally inoculated at $5 \times 10^7$ CFU/mouse unless otherwise indicated. For making S.p. crude extract, S.p. was harvested from a plate of chocolate agar after overnight incubation and inoculated in 50 ml of THY. After overnight incubation, the early-stationary phase S.p. that was monitored by measurement of OD (optical density) value was centrifuged at 10,000×g for 20 minutes at 4° C., and the supernatant was discarded. The resulting pellet of S.p. was suspended in 15 ml of phosphate-buffered saline and sonicated. Subsequently, the lysate was collected and stored at −80° C. Efficient disruption of the live bacteria was monitored by bacterial colony formation assay. In experiments using pneumolysin, pneumolysin was used at a concentration of 100-200 ng/ml for in vitro experiments unless otherwise indicated. Based on the concentration of released pneumolysin by autolysis of $5 \times 10^7$ CFU of S.p. and previous in vivo studies (Benton et al., "Differences in Virulence for Mice Among *Streptococcus pneumonia* Strains of Capsular Types 2, 3, 4, 5, and 6 Are not Attributable to Differences in Pneumolysin Production," *Infect. Immun.* 65:1237-44 (1997); Maus et al., "Pneumolysin-induced Lung Injury Is Independent of Leukocyte Trafficking into the Alveolar Space," *J. Immunol.* 173:1307-12 (2004); Rijneveld et al., "Roles of Interleukin-6 and Macrophage Inflammatory Protein-2 in Pneumolysin-induced Lung Inflammation in Mice," J. Infect. Dis. 185:123-6 (2002); Paton et al., "Cloning and Expression in *Escherichia coli* of the *Streptococcus pneumoniae* Gene Encoding Pneumolysin," *Infect. Immun.* 54:50-5 (1986), each of which is hereby incorporated by reference in its entirety), pneumolysin was used at a concentration of 5-10 µg/kg (approximately 100-200 ng/mouse) for in vivo experiments unless otherwise indicated. The S.p. lysate used in these studies contains approximately 100-200 ng/ml of pneumolysin, a concentration comparable with that of the purified pneumolysin used in these experiments, as assessed by performing ELISA assay using a pneumolysin antibody (Novocastra Laboratory, UK).

Example 3

Purification of Pneumolysin

Native pneumolysin (Srivastava et al., "The Apoptotic Response to Pneumolysin Is Toll-like Receptor 4 Dependent and Protects Against Pneumococcal Disease," *Infect. Immun.* 73:6479-87 (2005), which is hereby incorporated by reference in its entirety) was used unless otherwise indicated. In addition, recombinant pneumolysin was also used to confirm the key results obtained from using the native pneumolysin. Similar to native pneumolysin, recombinant pneumolysin also induced up-regulation of PAI-1 expression, lung hemorrhage, and lethality. Native pneumolysin was purified according to Malley et al., "Recognition of Pneumolysin by Toll-like Receptor 4 Confers Resistance to Pneumococcal Infection," *Proc. Nat'l Acad. Sci. USA* 100:1966-71 (2003), Paton et al., "Purification and Immunogenicity of Genetically Obtained Pneumolysin Toxoids and Their Conjugation to *Streptococcus pneumoniae* Type 19F Polysaccharide," *Infect. Immun.* 59:2297-304 (1991), and Paton et al., "Effect of Immunization with Pneumolysin on Survival Time of Mice Challenged with *Streptococcus pneumoniae,*" *Infect. Immun.* 40:548-52 (1983), each of which is hereby incorporated by reference in its entirety. Briefly, native pneumolysin was purified from whole-cell lysates (Paton et al., "Effect of Immunization with Pneumolysin on Survival Time of Mice Challenged with *Streptococcus pneumoniae,*" *Infect. Immun.* 40:548-52 (1983), which is hereby incorporated by reference in its entirety). Fractions from a DEAE-cellulose column containing pneumolysin were pooled and concentrated by using an Amicon model 52 stirred cell ultrafiltration apparatus fitted with a YM10 membrane (10,000 molecular weight retention). The concentrate was then applied to a column of Sephacyryl S-200 and eluted with 50 mM sodium phosphate (pH 7.0) at 4° C. Fractions with peak activities were pooled, concentrated by ultrafiltration, and fractions were collected through electroelution and assayed for pneumolysin, and those with activities greater than 2,000 HU/ml were pooled, concentrated by ultrafiltration, and stored in 50% glycerol at −20° C.

The recombinant pneumolysin was purified as described in Srivastava et al., "The Apoptotic Response to Pneumolysin Is Toll-like Receptor 4 Dependent and Protects Against Pneumococcal Disease," *Infect. Immun.* 73:6479-87 (2005), which is hereby incorporated by reference in its entirety. In brief, chromosomal DNA was prepared from S.p., and the gene for pneumolysin was amplified and cloned into the pQE expression vector (Qiagen) that generates N-terminal 6×His-tagged fusion proteins. Expression was induced by the addition of IPTG (1.0 mM) in *E. coli* and then purified by binding to $Ni^{2+}$ immobilized on resin according to the manufacturer's instructions (Qiagen). The residual lipopolysaccharide was further removed by End-X endotoxin affinity resin (Associates of Cape Cod, East Falmouth, Mass.). The levels of endotoxin were determined by the QCL-1000 Chromogenic LAL Endpoint Assay (Cambrex).

Example 4

Mammalian Cell Culture

Human alveolar epithelial cell line A549 and bronchial epithelial cell line BEAS 2B were maintained as described in Wang et al., "Novel Cytoplasmic Proteins of Nontypeable *Haemophilus influenzae* Up-regulate Human MUC5AC Mucin Transcription via a Positive p38 Mitogen-activated Protein Kinase Pathway and a Negative Phosphoinositide 3-Kinase-Akt Pathway," *J. Biol. Chem.* 277:949-57 (2002), Andrew et al., "AP-1-dependent Induction of Plasminogen Activator Inhibitor-1 by Nickel Does not Require Reactive Oxygen," *Am. J. Physiol. Lung Cell. Mol. Physiol.* 281:L616-23 (2001), and Hasegawa et al., "Decreased Intracellular Iron Availability Suppresses Epithelial Cell Surface Plasmin Generation. Transcriptional and Post-transcriptional Effects on u-PA and PAI-1 Expression," *Am. J. Respir. Cell. Mol. Biol.* 21:275-82 (1999), each of which is hereby incorporated by reference in its entirety. Wild type and Cyld-deficient mouse embryonic fibroblasts were obtained from E13 embryos and maintained in DMEM supplemented with 10% FBS (Invitrogen). Primary normal human small airway epithelial cells and primary normal human bronchial epithelial cells were purchased from Cambrex and were maintained in Small Airway cell Basal Medium and Bronchial Epithelial cell Growth Medium, respectively (Shuto et al., "Glucocorticoids Synergistically Enhance Nontypeable *Haemophilus influenzae*-induced Toll-like Receptor 2 Expression via a Negative Crosstalk with p38 MAP Kinase," *J. Biol. Chem.* 277:17263-70 (2002); Sakai et al., "Glucocorticoids Synergize with IL-1β to Induce TLR2Expression via MAP Kinase Phosphatase-1-dependent Dual Inhibition of MAPK JNK and p38 in Epithelial Cells," *BMC Mol. Biol.* 4(5):2 (2004); Imasato et al, "Inhibition of p38 MAPK by Glucocorticoids via Induction of MAPK Phosphatase-1 Enhances Nontypeable *Haemophilus influenzae*-induced Expression of Toll-like Receptor 2," *J. Biol. Chem.* 277:47444-50 (2002); Watanabe et al., "Synergistic Activation of NF-κB by Nontypeable *Haemophilus influenzae* and Tumor Necrosis Factor α," *Proc. Nat'l Acad. Sci. USA.* 101:3563-8 (2004), each of which is hereby incorporated by reference in its entirety).

All cells were cultured in a humidified atmosphere of 5% saturated $CO_2$ and 95% air at 37° C.

Example 5

Plasmids, Transfections, and Luciferase Assays

The expression plasmids hTLR4 DN (dominant-negative mutant), TLR2 DN, MyD88 DN, TRAF2 DN, TRAF6 WT&DN, TRAF7 WT&DN, MKK3b(E), and CYLD WT and the deubiquitinase-deficient mutants of CYLD (C/S CYLD and H/N CYLD) were described previously (Kovalenko et al., "The Tumour Suppressor CYLD Negatively Regulates NF-κB Signalling by Deubiquitination," *Nature* 424:801-5 (2003); Trompouki et al., "CYLD Is a Deubiquitinating Enzyme That Negatively Regulates NF-κB Activation by TNFR Family Members," *Nature* 424:793-6 (2003); Shuto et al., "Glucocorticoids Synergistically Enhance Nontypeable *Haemophilus influenzae*-induced Toll-like Receptor 2 Expression via a Negative Cross-talk with p38 MAP Kinase," *J. Biol. Chem.* 277:17263-70 (2002); Sakai et al., "Glucocorticoids Synergize with IL-1β to Induce TLR2 Expression via MAP Kinase Phosphatase-1-dependent Dual Inhibition of MAPK JNK and p38 in Epithelial Cells," *BMC Mol. Biol.* 4(5):2 (2004); Imasato et al, "Inhibition of p38 MAPK by Glucocorticoids via Induction of MAPK Phosphatase-1 Enhances Nontypeable *Haemophilus influenzae*-induced Expression of Toll-like Receptor 2," *J. Biol. Chem.* 277:47444-50 (2002); Watanabe et al., "Synergistic Activation of NF-κB by Nontypeable *Haemophilus influenzae* and Tumor Necrosis Factor α," *Proc. Nat'l Acad. Sci. USA* 101:

3563-8 (2004); Li, "Exploitation of Host Epithelial Signaling Networks by Respiratory Bacterial Pathogens," *J. Pharmacol. Sci.* 91:1-7 (2003); Wang et al., "Novel Cytoplasmic Proteins of Nontypeable *Haemophilus influenzae* Up-regulate Human MUC5AC Mucin Transcription via a Positive p38 Mitogen-activated Protein Kinase Pathway and a Negative Phosphoinositide 3-Kinase-Akt Pathway," *J. Biol. Chem.* 277:949-57 (2002); Jono et al., "Transforming Growth Factor-β-Smad Signaling Pathway Cooperates with NF-κB to Mediate Nontypeable *Haemophilus influenzae*-induced MUC2 Mucin Transcription," *J. Biol. Chem.* 277:45547-57 (2002); Jono et al., "Transforming Growth Factor-β-Smad Signaling Pathway Negatively Regulates Nontypeable *Haemophilus Influenzae*-induced MUC5AC Mucin Transcription via Mitogen-activated Protein Kinase (MAPK) Phosphatase-1-dependent Inhibition of p38 MAPK," *J. Biol. Chem.* 278:27811-9 (2003); Shuto et al., "Activation of NF-κB by Nontypeable *Hemophilus influenzae* Is Mediated by Toll-like Receptor 2-TAK1-dependent NIK-IKK α/β-I κB α and MKK3/6-p38 MAP Kinase Signaling Pathways in Epithelial Cells," *Proc. Nat'l Acad. Sci. USA* 98:8774-9 (2001); Li et al., "Activation of NF-κB via a Src-dependent Ras-MAPK-pp 90rsk Pathway Is Required for *Pseudomonas aeruginosa*-induced Mucin Overproduction in Epithelial Cells," *Proc. Nat'l Acad. Sci. USA* 95:5718-23 (1998); Huang et al., "Differential Regulation of Interleukin 1 Receptor and Toll-like Receptor Signaling by MEKK3," *Nat. Immunol.* 5:98-103 (2004); Chen et al., "Nontypeable *Haemophilus influenzae* Lipoprotein P6 Induces MUC5AC Mucin Transcription via TLR2-TAK1-dependent p38 MAPK-AP1 and IKKβ-IκBα-NF-κB Signaling Pathways," *Biochem. Biophys. Res. Commun.* 324:1087-94 (2004); Wang et al., "Up-regulation of Interleukin-8 by Novel Small Cytoplasmic Molecules of Nontypeable *Haemophilus influenzae* via p38 and Extracellular Signal-regulated Kinase Pathways," *Infect. Immun.* 71:5523-30 (2003), each of which is hereby incorporated by reference in its entirety). The dominant-negative mutant expression plasmids for MKK3, p38α, and p38β were described in Imasato et al., "Inhibition of p38 MAPK by Glucocorticoids via Induction of MAPK Phosphatase-1 Enhances Nontypeable *Haemophilus influenzae*-induced Expression of Toll-like Receptor 2," *J. Biol. Chem.* 277:47444-50 (2002), which is hereby incorporated by reference in its entirety. The luciferase reporter construct for PAI-1 was also previously described (Jono et al., "Transforming Growth Factor-β-Smad Signaling Pathway Cooperates with NF-κB to Mediate Nontypeable *Haemophilus influenzae*-induced MUC2 Mucin Transcription," *J. Biol. Chem.* 277: 45547-57 (2002), which is hereby incorporated by reference in its entirety).

Cells were cultured on 12-well plates and transfected with various expression plasmids, as described in Examples 1-15 and the Brief Description of the Drawings. All transient transfections were carried out in triplicate using TransIT-LT1 reagent (Minis) following the manufacturer's instructions. TransIT-LT1 was chosen because of its superior transfection efficiency in a variety of cell lines and very low toxicity. Transfected cells were pretreated with or without chemical inhibitors including SB203580 (1 µM) for 2 hours. S.p. or pneumolysin was then added to the transfected cells 42 hours after transfection. After 5 hours, the cells were harvested for either RNA extraction and real-time quantitative PCR analysis as described in the Examples or luciferase assay. Luciferase activity was normalized with respect to β-galactosidase activity using the Galacton-Plus substrate system (Tropix) following manufacturer's instruction. In all co-transfections with expression plasmids of signaling molecules, an empty vector was used as a control.

Example 6

RNA-Mediated Interference

RNA-mediated interference for down-regulating gene expression was carried out by the transfection of either double-strand siRNA oligonucleotides or siRNA expression plasmid. Transfections of double-strand siRNA oligonucleotides were carried out with RNAiFect™ Transfection Reagent (Qiagen). Transfections of siRNA expression plasmid were carried out with TransIT-LT1 reagent (Mirus). Both transfections followed the manufacturers' instructions. The siRNA oligonucleotides are commercially available from QIAGEN (MKK3, p38α, and p38β, Ambion (TRAF6) and Dharmacon (TRAF7). The siRNA expression vector for CYLD and the control vector are described in Brummelkamp et al., "Loss of the Cylindromatosis Tumour Suppressor Inhibits Apoptosis by Activating NF-κB," *Nature* 424:797-801 (2003), Yoshida et al., "The Tumor Suppressor Cylindromatosis (CYLD) Acts as a Negative Regulator for Toll-like Receptor 2 Signaling via Negative Cross-talk with TRAF6 and TRAF7," *J. Biol. Chem.* 280:41111-21 (2005), and Jono et al., "NF-κB Is Essential for Induction of CYLD, the Negative Regulator of NF-κB: Evidence for a Novel Inducible Autoregulatory Feedback Pathway," *J. Biol. Chem.* 279:36171-4 (2004), each of which is hereby incorporated by reference in its entirety.

Example 7

Mice

Cyld-deficient mice were generated by homologous recombination as follows. The targeting construct was designed to disrupt exons 2 and 3 with an IRES-LacZ/MC1-Neo cassette. The targeting plasmid was linearized and transfected into embryonic stem cells of a 129/S mouse. Homologously recombined embryonic stem cells were injected into blastocysts, which were subsequently transferred to foster mothers to generate chimeric progeny. The chimeric progeny were backcrossed to C57BL/6J mice, and germline transmission was confirmed by PCR using tail DNA. Homozygous knockout of the Cyld gene was confirmed by RT-PCR for mRNA detection and western blot analysis for CYLD protein detection in mouse embryonic fibroblasts and lung tissues. MKK3-deficient mice are described in Lu et al., "Defective IL-12 Production in Mitogen-activated Protein (MAP) Kinase Kinase 3 (Mkk3)-deficient Mice," *EMBO J.* 18:1845-57 (1999), which is hereby incorporated by reference in its entirety. PAI/−/−deficient mice were purchased from The Jackson Laboratory (Maine, U.S.A). Sex- and age-matched background C57BL/6J mice were used as wild-type controls. BALB/c mice were also used to confirm the results using another mouse strain.

Example 8

Animal Experiments

For *S. pneumoniae*-induced lethal infections in wild type, Cyld$^{-/-}$, Mkk3$^{-/-}$, and PAI-1$^{-/-}$ mice, anaesthetized mice were intratracheally inoculated with live *S. pneumoniae, S. pneumoniae* wild type or pneumolysin mutant lysate, or pneumolysin ("PLY"), at a concentration of 5×10$^7$ CFU per mouse for live bacteria and bacterial lysate and 200 ng/mouse for PLY in all experiments unless otherwise indicated, and saline was inoculated as control. The mice were monitored for lethality every 2 hours for the first 12 hours and every 12 hours for 5 days thereafter. To assess the effect of perturbing p38 MAPK signaling on *S. pneumoniae-induced* lethality in Cyld$^{-/-}$ mice, Cyld$^{-/-}$ mice were pretreated with the p38 inhibitor SB203580 (10 mg/kg, intraperitoneally in Cyld$^{-/-}$ mice) 2 hours before *S. pneumoniae* inoculation, and mice were then intratracheally inoculated with *S. pneumoniae*. To determine the effect of administration of exogenous PAI-1 on *S. pneumoniae-induced* lethality, mice were intratracheally administered with mouse rPAI-1 (12.5 µg/mouse) or saline as control, followed by *S. pneumoniae* and PLY inoculation 1 day after PAI-1 administration. For PAI-1 neutralization in Cyld$^{-/-}$ mice, Cyld$^{-/-}$ mice were intraperitoneally injected with α-PAI-1 mAb (25 µg/mouse for histological analysis and 50 µg/mouse for lethality) 2 hours before *S. pneumoniae* inoculation. Mouse IgG was used as control. For *S. pneumoniae-* and PLY-induced MAPK phosphorylation, PAI-1 and CYLD mRNA and protein expression, and lung hemorrhage/acute lung injury, anaesthetized mice were intratracheally inoculated with *S. pneumoniae* or PLY with or without SB203580, rPAI-1, or α-PAI-1 mAb, and mice were then sacrificed at 6 hours after inoculation of *S. pneumoniae* unless otherwise indicated. Lung tissues were then subjected to histological analysis and total mRNA and protein extraction. In all Examples, saline was used as a control unless otherwise specified.

To assess the effect of perturbing NF-κB signaling on S.p.-induced lethality in Cyld$^{-/-}$ mice, Cyld$^{-/-}$ mice were pretreated with the IKK inhibitor Wedelolactone (10 mg/kg, intraperitoneally) 2 hours before S.p. inoculation, and mice were then intratracheally inoculated with S.p.

Example 9

RNA Extraction and Real-time Quantitative RT-PCR ("Q-PCR")

Total RNA was isolated with TRIzol reagent (Invitrogen) by following the manufacturer's instructions. Real-Time Quantitative RT-PCR analysis of PAI-1 and CYLD were performed as described in Jono et al., "NF-κB Is Essential for Induction of CYLD, the Negative Regulator of NF-κB: Evidence for a Novel Inducible Autoregulatory Feedback Pathway," *J. Biol. Chem.* 279:36171-4 (2004), which is hereby incorporated by reference in its entirety. The primers were: human PAI-1 forward primer 5'-gttctatgagggctgcgtcttt-3' (SEQ ID No: 11) and reverse primer 5'-ggctggagcacaccacatc-3' (SEQ ID No: 12); mouse PAI-1 forward primer 5'-aaagacaccagtagtcactcagcaa-3' (SEQ ID No: 13) and reverse primer 5'-ctgggaagtcagtgtcaaacca-3' (SEQ ID No: 14); and mouse CYLD forward primer (5'-ctcagcctatttagaaacagact-3' (SEQ ID No: 15) and reverse primer 5'-tctcctgggcctgcaaaat-3' (SEQ ID No: 16) (Jono et al., "Transforming Growth Factor-β-Smad Signaling Pathway Negatively Regulates Nontypeable *Haemophilus Influenzae-*induced MUC5AC Mucin Transcription via Mitogen-activated Protein Kinase (MAPK) Phosphatase-1-dependent Inhibition of p38 MAPK," *J. Biol. Chem.* 278:27811-9 (2003), which is hereby incorporated by reference in its entirety). Quantitative analysis of mRNA expression was performed using the ABI PRISM 7500 sequence detection system (Applied Biosystems) using the manufacturer's software according to the manufacturer's instructions (Yoshida et al., "The Tumor Suppressor Cylindromatosis (CYLD) Acts as a Negative Regulator for Toll-like Receptor 2 Signaling via Negative Cross-talk with TRAF6 and TRAF7," *J. Biol. Chem.* 280:41111-21 (2005), which is hereby incorporated by reference in its entirety). Relative quantity of PAI-1 mRNA was obtained using comparative CT Method and was normalized by Cyclophilin and GAPDH as an endogenous control for human and mouse, respectively (Applied Biosystems).

Example 10

Western Blot Analysis and Protein Kinase Assay

Western blot analysis was performed as described in Yoshida et al., "The Tumor Suppressor Cylindromatosis (CYLD) Acts as a Negative Regulator for Toll-like Receptor 2 Signaling via Negative Cross-talk with TRAF6 and TRAF7," *J. Biol. Chem.* 280:41111-21 (2005), which is hereby incorporated by reference in its entirety. Cell and whole lung lysates were prepared and incubated with anti-phospho-MKK3/6, anti-phospho-p38 MAPK, anti-MKK3, anti-p38MPAK, anti-β-actin, anti-CYLD, or anti-PAI-1. Quantitative protein expression was analyzed using Kodak MI Alias (Kodak, New York, U.S.A.).

p38 kinase assay was carried out following the instructions from New England Biolabs. In brief, cell lysate and immobilized phospho-p38 antibody were incubated with gentle rocking overnight at 4° C. The immunoprecipitates were washed twice with lysis buffer and twice with kinase buffer (25 mM Tris base, 5 mM β-Glycerolphosphate, 2 mM DTT, 0.1 mM Na$_3$VO$_4$, 10 mM MgCl$_2$, pH7.4). The kinase reactions were carried out in the presence of 200 µM ATP and 2 µg of GST-ATF-2 fusion protein at 30° C. for 30 minutes. ATF-2 phosphorylation was selectively measured by using phospho-ATF-2 antibody. Protein bands were visualized using secondary HRP-conjugated anti-Rabbit- or anti-Mouse-IgG and the ECL detection system (Amersham Biosciences), detected using Imaging Station 4000R (Kodak, New York, U.S.A). Quantitative protein expression was analyzed using Kodak MI Alias (Kodak, New York, U.S.A.).

Example 11

Histology

For histological analysis, dissected lungs were fixed with 10% buffered neutral formalin overnight with rocking followed by routine processing, embedded in paraffin, and sectioned at about 4 µm thickness. Sections were stained with hematoxylin and eosin ("H&E") to visualize lung inflammation and hemorrhage. H&E-stained lung tissue slides were evaluated by light microscopy using Axiovert 40 CFL (Carl Zeiss), and images were recorded with an AxioCam MRC (Carl Zeiss).

Example 12

Statistical Analysis

Differences in survival between wild-type, Cyld-deficient ("Cyld$^{-/-}$"), Mkk3-deficient ("Mkk3$^{-/-}$"), and PAI-/-deficient ("PAI-1$^{-/-}$") mice after saline, *S. pneumoniae*, *S. pneumoniae* lysate, and/or pneumolysin inoculation with or without SB203580, rPAI-1, or α-PAI-1 mAb were determined by Kaplan-Meier analysis. All tests were performed using SPSS14.0 software (SPSS Inc.). All in vivo survival rate data were evaluated by Log Lank test. All other in vivo and in vitro data were evaluated by Student t-test. Statistical significance was accepted at a value of p<0.05.

Example 13

Immunoprecipitation

Cells were lysed in lysis buffer (20 mM Tris base, 50 mM NaCl, 50 mM sodium pyrophosphate, 30 mM NaF, 5 µM zinc chloride, 2 mM iodoacetic acid, 1% Triton X-100, pH 7.4) supplemented with "Complete" protease inhibitors (Roche Applied Science). 500 µl cell lysate (400-500 µg of total cellular protein) were precleared with protein A/G-agarose beads (Santa Cruz Biotechnology) for 1 hour at 4° C. After centrifugation, supernatant was immunoprecipitated with 2 µg of the appropriate antibodies for 90 minutes at 4° C. and then conjugated to protein A/G-agarose beads overnight at 4° C. Immunoprecipitates were washed four times with the lysis buffer and suspended in a sample buffer (15% glycerol, 0.14M Tris-HCl, pH 6.8, 1% SDS, 0.5M dithiothreitol, 0.0006% bromphenol blue).

Example 14

Immunofluorescence

Cells were cultured on four-chamber slides and were co-transfected with the indicated combinations of TRAF6, HA-TRAF7, and FLAG-CYLD plasmids. Forty-eight hours after transfection, cells were fixed in 4% paraformaldehyde and permeabilized with 0.5% Triton X-100 in phosphate-buffered saline ("PBS") for 15 minutes. Fixed cells were subsequently blocked with 1.5% bovine serum albumin in PBS for 20 minutes and incubated with rabbit anti-TRAF6 antibody, rabbit anti-HA antibody (Santa Cruz Biotechnology), or mouse anti-FLAG antibody (Sigma). Primary antibodies were detected with fluorescein isothiocyanate-conjugated anti-mouse or rhodamine-conjugated anti-rabbit secondary antibody (Santa Cruz Biotechnology). Samples were examined and photographed by using an Axiophot microscope (Carl Zeiss).

Example 15

S. pneumoniae Pneumolysin Induces ALI and Lethality in Vivo

To investigate the molecular mechanism underlying S. pneumoniae-induced acute lung injury ("ALI") and lethality in severe pneumococcal pneumonia, lethal pneumonia was first induced in wild type mice by intratracheal inoculation of live S. pneumoniae strain D39 (a virulent serotype 2). As shown in FIG. 2A, live S. pneumoniae-inoculated mice started to die within 48 hours after inoculation, and nearly 66% of the inoculated mice died within 72 hours.

S. pneumoniae undergoes spontaneous autolysis. Autolysis can also be triggered in vivo under various conditions, including antibiotic treatment. Pneumolysin ("PLY"), a cytoplasmic protein released from lysed bacteria, is known to exert potent cytotoxic effects on host cells to cause tissue damage such as ALI (Cockeran et al., "The Role of Pneumolysin in the Pathogenesis of Streptococcus pneumoniae Infection," Curr. Opin. Infect. Dis. 15:235-9 (2002); Hollingshead & Briles, "Streptococcus pneumoniae: New Tools for an Old Pathogen," Curr. Opin. Microbiol. 4:71-7 (2001), each of which is hereby incorporated by reference in its entirety). Therefore, the effect of intratracheal inoculation of S. pneumoniae D39 lysate ("S. pneumoniae WT lysate") in wild type mice was also evaluated. As shown in FIG. 2A, in contrast to live S. pneumoniae-inoculated mice, mice inoculated with S. pneumoniae WT lysate started to die within a few hours after inoculation, and 91% of the inoculated mice died within 48 hours, implying that released virulence factors such as PLY play an important role in inducing lethality.

To further determine whether PLY plays a key role in S. pneumoniae-induced lethality, the lethality in mice inoculated with lysate from a D30 isogenic mutant strain lacking the pneumolysin gene ("S. pneumoniae Ply MT") was compared with that of mice inoculated with S. pneumoniae WT lysate or with saline as a control. As shown in FIG. 2B, all mice inoculated with S. pneumoniae Ply MT lysate survived (100% survival by the end of the experiment (approximately 120 hours)), as did vehicle-treated control mice, suggesting that PLY does play a crucial role in S. pneumoniae-induced lethality. Indeed, as shown in FIG. 2B, direct intratracheal inoculation with purified pneumolysin induced severe lethality, similar to S. pneumoniae WT lysate.

Since S. pneumoniae strain D39 is a virulent serotype 2 strain, it was predicted that another virulent strain would induce lethality in mice in a similar way. As shown in FIG. 3, as expected, virulent serotype 4 TIGR4, a S. pneumoniae strain that was used for sequencing the whole-genome of S. pneumoniae, induced lethality similarly to strain D39, indicating that S. pneumoniae D39-induced lethality may be also applied to other virulent strains of S. pneumoniae.

PLY is well known to exert direct cytotoxic effects on the alveolar-capillary barrier and thus induce ALI, one of the important pathological processes causing death in pneumonia-infected patients, especially during the early phase of severe pneumococcal pneumonia (Cockeran et al., "The Role of Pneumolysin in the Pathogenesis of Streptococcus pneumoniae Infection," Curr. Opin. Infect. Dis. 15:235-9 (2002); Grigoryev et al., "Science Review: Searching for Gene Candidates in Acute Lung Injury," Crit. Care 8:440-7 (2004); Hollingshead & Briles, "Streptococcus pneumoniae: New Tools for an Old Pathogen," Curr. Opin. Microbiol. 4:71-7 (2001); Kadioglu & Andrew, "The Innate Immune Response to Pneumococcal Lung Infection The Untold Story," Trends Immunol. 25:143-9 (2004), each of which is hereby incorporated by reference in its entirety). Indeed, as shown in FIG. 2C, pathological analysis of lung injury of S. pneumoniae WT- and PLY-inoculated mice revealed massive alveolar hemorrhage 6 hours after inoculation, while S. pneumoniae Ply MT-inoculated mice did not.

Together, these data suggest that PLY plays a crucial role in inducing ALI, hemorrhage, and lethality. The findings from this mouse model (a model of lethal S. pneumoniae infections) are completely in line with the typical pathological changes of pneumococcal lobar pneumonia at the early stage of infection in human patients (Lagoa et al., "The Role of Hepatic Type 1 Plasminogen Activator Inhibitor (PAI-1) During Murine Hemorrhagic Shock," Hepatol. 42:390-9 (2005); Ware et al., "Coagulation and Fibrinolysis in Human Acute Lung Injury—New Therapeutic Targets?" Keio J. Med. 54:142-9 (2005), each of which is hereby incorporated by reference in its entirety). Histologically, during the initial stage of invasion the affected human lung is fully filled with red blood cells and fibrin but few polymorphonuclear neutrophils ("PMNs"). This stage, seldom recognized although well described by Loeschcke, Beitr. Path. Anat. 86:201 (1931), which is hereby incorporated by reference in its entirety, is most often found in patients who die within a short time period after the onset of the disease. Indeed, clinical and pathological evidence directly obtained from a patient who died within a short time period from pneumococcal lobar pneumonia is in full agreement with the present animal studies. As shown in FIG. 4, light microscopic examination of the lung tissue revealed that the alveolar spaces were diffusely filled with red blood cells and only a few PMNs. Thus, the findings from the present animal studies are highly relevant to human diseases.

Example 16

CYLD Deficiency Protects Mice from Acute Lung Injury and Reduces the Mortality Rate in Lethal *S. pneumoniae* Infections To define the biological role of CYLD in vivo, Cyld-deficient mice (Cyld$^{-/-}$ mice) were generated by replacing exons 2 and 3 of the Cyld gene with a neomycin resistance-lacZ cassette, as shown in FIG. 5A. Disruption of the Cyld gene is compatible with normal viability, development, and fertility. Genotyping was performed by PCR on tail-derived genomic DNA, and germline transmission was confirmed by Southern blot analysis. RT-PCR analysis confirmed the absence of Cyld transcripts in homozygous mutant mice, as shown in FIG. 5B (top), and integrated backscatter ("IB") analysis of mouse embryonic fibroblasts ("MEF") using an antibody against CYLD showed a deficiency of CYLD in Cyld$^{-/-}$ mice, as shown in FIG. 5B (bottom). Interestingly, Cyld-deficient mice exhibited no overt abnormalities and had a normal lifespan.

Based on a study showing that CYLD is greatly induced by bacterial pathogens (Jono et al., "NF-κB Is Essential for Induction of CYLD, the Negative Regulator of NF-κB: Evidence for a Novel Inducible Autoregulatory Feedback Pathway," *J. Biol. Chem.* 279:36171-4 (2004); Yoshida et al., "The Tumor Suppressor Cylindromatosis (CYLD) Acts as a Negative Regulator for Toll-like Receptor 2 Signaling via Negative Cross-talk with TRAF6 and TRAF7," *J. Biol. Chem.* 280: 41111-21 (2005), each of which is hereby incorporated by reference in its entirety), it was hypothesized that CYLD may play an important role in bacterial infections. Since CYLD expression is highly induced in lung tissue, the initial focus was on elucidating the role of CYLD in lethal lung infections induced by *S. pneumoniae* PLY.

Whether CYLD is induced by *S. pneumoniae* was first determined. CYLD expression in lung tissues from wild type mice at the mRNA level was greatly up-regulated by intratracheal inoculation of wild type *S. pneumoniae* or pneumolysin, but not by *S. pneumoniae* Ply MT ("PLN"), as shown in FIG. 6A, implying a potential role of CYLD during *S. pneumoniae* infections.

To determine the role of CYLD in *S. pneumoniae*-induced lethality, wild type and Cyld$^{-/-}$ mice were intratracheally inoculated with *S. pneumoniae*, and viability was then assessed. As shown in FIG. 6B, *S. pneumoniae*-inoculated Cyld$^{-/-}$ mice started to die within 48 hours after inoculation and only 13% died within 5 days (87% survival). In contrast, wild type mice inoculated with *S. pneumoniae* started to die within a few hours after inoculation, and 91% of the inoculated mice died within 48 hours (9% survival). Similar results were also observed in Cyld$^{-/-}$ mice inoculated with PLY, as shown in FIG. 6C. Consistent with these findings, histological analysis showed that lungs from Cyld$^{-/-}$ mice exhibited almost no signs of hemorrhage in comparison with marked alveolar hemorrhage observed in lungs from wild type mice after *S. pneumoniae* or PLY inoculation, as shown in FIG. 6D. These data demonstrate that CYLD deficiency protects mice from *S. pneumoniae* PLY-induced ALI and lethality.

In addition to the pathological analysis, the body temperature was examined and gravimetric analysis was performed, including the extravascular lung water and protein concentration. As shown in FIG. 6E, wild type mice inoculated with *S. pneumoniae* WT lysate and PLY, but not with *S. pneumoniae* Ply MT lysate, showed significant decreases in body temperature as compared with Cyld$^{-/-}$ mice. Moreover, gravimetric analysis demonstrated that extravascular lung water weight and total protein concentration were significantly increased in lungs of wild type mice inoculated with *S. pneumoniae* WT lysate and PLY, but not with *S. pneumoniae* Ply MT lysate, as compared with Cyld$^{-/-}$ mice, as shown in FIGS. 6F-G. Thus, these data suggest that Cyld-deficiency also protects mice from hypothermia and microvascular leakage.

Next, the possibility that the protective role of Cyld-deficiency may work in part by preventing translocation of bacteria and bacterial dissemination by walling off the infection in the lung, not just by preventing local tissue injury in the lung, was explored. Bacterial counts were measured in the lung and blood of wild type and Cyld$^{-/-}$ mice 24 hours after intratracheal inoculation of *S. pneumoniae* WT D39 and *S. pneumoniae* Ply MT. As shown in FIG. 7A, bacterial counts in the lungs of wild type mice inoculated with *S. pneumoniae* WT D39 were significantly greater than those inoculated with *S. pneumoniae* Ply MT. Interestingly, the bacterial counts in the lungs from wild type mice inoculated with *S. pneumoniae* WT D39 strain were not statistically different from the counts of the inoculated Cyld$^{-/-}$ mice. By contrast, although bacterial culture in the blood was positive in 6/10(60%) of the inoculated Cyld$^{-/-}$ mice and positive in 7/10(70%) of the inoculated wild type mice, circulating bacterial counts in the blood from the inoculated Cyld$^{-/-}$ mice were significantly lower than those from the inoculated wild type mice, as shown in FIG. 7B. These data indicate that the protective role of CYLD deficiency may not only work by preventing ALI, but also at least in part by attenuating translocation of bacteria and bacterial dissemination by walling off the infection in the lung. Collectively, these data suggest that CYLD indeed plays a crucial role in regulating ALI and bacterial translocation in lethal *S. pneumoniae* infections, thus acting as a critical negative regulator for host survival.

Example 17

CYLD Deficiency Protects Against Pneumolysin-Induced Acute Lung Injury and Death via Enhancement of PAI-1 Expression in Lung Having demonstrated a critical role for CYLD in lethal *S. pneumoniae* infections, it was next sought to elucidate the molecular mechanisms by which CYLD deficiency protects against ALI, one of the major pathological processes contributing to *S. pneumoniae*-induced lethality during the early course of pneumococcal pneumonia (Bignell et al. "Identification of the Familial Cylindromatosis Tumour-suppressor Gene," *Nat. Genet.* 25:160-5 (2000); Grigoryev et al., "Science Review: Searching for Gene Candidates in Acute Lung Injury," *Crit. Care* 8:440-7 (2004); Schwarz, "Acute Lung Injury: Cellular Mechanisms and Derangements," *Pediatr. Respir. Rev.* 2:3-9 (2001), each of which is hereby incorporated by reference in its entirety). Thus, it was investigated whether CYLD acts as a negative regulator for PAI-1 expression and CYLD deficiency results in elevated PAI-1 expression, which in turn leads to diminished ALI and alveolar hemorrhage in lungs.

To test this hypothesis, the expression level of PAI-1 mRNA was assessed in mouse embryonic fibroblasts ("MEF") and lung tissue from wild type and Cyld$^{-/-}$ mice. As shown in FIG. 8A, the expression of PAI-1 at both mRNA and protein levels is much higher in MEF and lung tissues from Cyld$^{-/-}$ mice than that from wild type mice.

To further determine whether higher PAI-1 expression in MEF cells from Cyld$^{-/-}$ mice is a developmental defect or simply results from loss of the inhibitory function of CYLD on PAI-1 expression, the effects of CYLD knock-down on PAI-1 mRNA expression was evaluated using small interfering RNA against CYLD ("siRNA-CYLD") in MEF cells from wild type mice, and overexpression of wt-CYLD in MEF cells from Cyld$^{-/-}$ mice. As shown in FIG. 9A, CYLD knock-down using siRNA-CYLD increased PAI-1 mRNA expression in wild type MEF cells, whereas overexpression of wt-CYLD attenuated PAI-1 mRNA expression in Cyld$^{-/-}$ MEF cells. Similar results were also observed when PAI-1 promoter activity was measured. As shown in FIG. 9B, PAI-1 promoter activity was increased by siRNA-CYLD in wild type MEF cells, but attenuated by wt-CYLD in Cyld$^{-/-}$ MEF cells in a dose-dependent manner. S. pneumoniae WT lysate and purified PLY, but not S. pneumoniae Ply MT lysate, induced PAI-1 expression in the human alveolar epithelial cell line A549, primary human small airway bronchial epithelial (SAEC), and lungs of wild type mice, as shown in FIGS. 10A-C. Moreover, induction of PAI-1 mRNA by S. pneumoniae and PLY was observed in wild type MEF cells and mouse lung inoculated with S. pneumoniae 3 and 6 hours after treatment, respectively, and the expression levels of PAI-1 were much higher in Cyld$^{-/-}$ MEF and Cyld$^{-/-}$ lung in both the S. pneumoniae-treated and non-treated groups, as compared with that in wild type MEF and wild type mice lungs, as shown in FIG. 8B and FIG. 8C.

In addition to mRNA expression, PAI-1 protein expression was also measured in control tissue and live S. pneumoniae-inoculated lung tissues from wild type and Cyld$^{-/-}$ mice 24 hours after inoculation, using immunohistochemical analysis. As shown in FIGS. 11A-L, highly enhanced immunoreactivity signal for PAI-1 was detected in both control and infected lungs from Cyld$^{-/-}$ mice compared with those from wild type mice.

To determine whether elevated PAI-1 expression is indeed responsible for the diminished ALI and alveolar hemorrhage in Cyld$^{-/-}$ mice, the effect of neutralization of PAI-1 in S. pneumoniae-induced ALI and lethality was evaluated using a neutralizing monoclonal antibody against PAI-1. The neutralizing antibody used in the present Example has been shown to inhibit both mouse and rat PAI-1 activity (Declerck et al., "Identification of a Conformationally Distinct Form of Plasminogen Activator Inhibitor-1, Acting as a Noninhibitory Substrate for Tissue-type Plasminogen Activator," J. Biol. Chem. 267:11693-6 (1992), which is hereby incorporated by reference in its entirety), and its efficacy in neutralizing PAI-1 activity has been demonstrated both in vitro and in vivo (Berry et al., "Antithrombotic Activity of a Monoclonal Antibody Inducing the Substrate Form of Plasminogen Activator Inhibitor Type 1 in Rat Models of Venous and Arterial Thrombosis," Br. J. Pharmacol. 125:29-34 (1998); Roca et al., "Hyperthermia Inhibits Angiogenesis by a Plasminogen Activator Inhibitor 1-dependent Mechanism," Cancer Res. 63:1500-7 (2003), each of which is hereby incorporated by reference in its entirety). As shown in FIG. 8D, intraperitoneal pre-administration of α-PAI-1 neutralizing antibody enhanced ALI and alveolar hemorrhage in Cyld$^{-/-}$ mice inoculated with S. pneumoniae. Consistent with these findings, S. pneumoniae-induced lethality was also markedly exacerbated by intraperitoneal inoculation of α-PAI-1 neutralizing antibody in Cyld$^{-/-}$ mice, as shown in FIG. 8E.

To further confirm whether elevated PAI-1 expression is indeed responsible for diminished ALI and lethality, the effect of exogenous PAI-1 on S. pneumoniae-induced lethality and ALI in wild type mice was evaluated. As shown in FIG. 8F and FIG. 8G, intratracheal inoculation with mouse recombinant PAI-1 ("rPAI-1") greatly reduced the mortality rate in mice inoculated with S. pneumoniae or PLY. Consistent with these findings, S. pneumoniae and PLY-induced alveolar hemorrhage was also prevented in mice inoculated with rPAI-1, as assessed by pathological and histological analysis, as shown in FIG. 8H.

To further confirm whether PAI-1 deficiency indeed potentiates ALI and reduces survival rate, wild type and PAI-1$^{-/-}$ mice were intratracheally inoculated with live S. pneumoniae, S. pneumoniae WT lysate and PLY, and viability was then assessed for 5 days after inoculation. As shown in FIGS. 12A-C, PAI-1$^{-/-}$ mice were significantly more susceptible to S. pneumoniae-inoculation than were wild type mice. PAI-1$^{-/-}$ mice inoculated with live S. pneumoniae, S. pneumoniae WT lysate, and PLY started to die at earlier time points than wild type mice, and all PAI-1$^{-/-}$ mice died within 5 days after inoculation. Consistent with these findings, S. pneumoniae- and PLY-induced ALI and alveolar hemorrhage was also enhanced in PAI-1$^{-/-}$ mice in comparison with wild type mice, as shown in FIG. 12D.

These findings are in contrast to those of Rijneveld et al. ("Plasminogen Activator Inhibitor Type-1 Deficiency Does not Influence the Outcome of Murine Pneumococcal Pneumoniae," Blood 102:934-49 (2003), which is hereby incorporated by reference in its entirety), which showed no significant influence of PAI-1 deficiency on the outcome of murine pneumococcal pneumonia. The differences in the bacterial strain (D39 vs. ATCC 6303), inoculation route (intratracheal vs. intranasal), or inoculation dosage ($5 \times 10^7$ CFU vs. $2 \times 10^5$ CFU) used in these two studies may have contributed to this discrepancy. To experimentally address these differences, S. pneumoniae strain D39 was intranasally inoculated in both wild type and PAI-1$^{-/-}$ mice to determine whether a different inoculation route would affect the protective role of PAI-1 in S. pneumoniae-induced lethality. As shown in FIG. 13A, PAI-1$^{-/-}$ mice showed higher mortality than wild type mice when the mice were intranasally inoculated with $5 \times 10^7$ CFU of strain D39. Since S. pneumoniae ATCC 6303, which was used by Rijneveld et al. ("Plasminogen Activator Inhibitor Type-1 Deficiency Does not Influence the Outcome of Murine Pneumococcal Pneumoniae," Blood 102:934-49 (2003), which is hereby incorporated by reference in its entirety), is known to have a higher lethality in mice compared with other strains of S. pneumoniae, the lethality in wild type mice of the two different strains (D39 vs. ATCC 6303) was examined. As shown in FIG. 13B, when mice were intranasally inoculated with $5 \times 10^7$ CFU of the bacteria, all mice inoculated with strain ATCC 6303 died within 3 days, but only 40% of the strain D39-inoculated mice died by 5 days after inoculation. Moreover, wild type mice inoculated with $2 \times 10^5$ CFU of strain ATCC 6303 mice started to die 3 days after inoculation and showed a survival rate around 55%, but none of the wild type mice inoculated with $2 \times 10^5$ CFU of strain D39 died by the end of the experiment.

Since these two strains of S. pneumoniae have a different lethality in mice, it was thought that the higher toxicity of strain ATCC 6303 would affect the protective role of PAI-1 on ALI and death. Therefore, the protective role of PAI-1 against strain ATCC 6303 was examined in wild type and PAI-1$^{-/-}$ mice. As shown in FIG. 13C, consistent with the findings with strain D39, strain ATCC 6303-inoculated PAI-1$^{-/-}$ mice showed higher mortality (10% survival) than wild type mice (45% survival), when the animals were intranasally inoculated with 2×10⁵ CFU of the bacteria. Taken together, these data suggest that PAI-1 plays a critical protective role in lethal pneumococcal infections.

Example 18

S. pneumoniae Pneumolysin Induces PAI-1 Expression via the MKK3-p38 MAPK Signaling Pathway Having demonstrated that PAI-1 is greatly induced by S.p. and plays a critical role in preventing excessive hemorrhage and lethality in lethal S.p. infections, it was next sought to determine how PAI-1 expression is induced by S.p. in pneumococcal pneumonia infections.

In review of the known signaling pathways involved in PAI-1 regulation, the MKK3-p38 MAPK pathway has been shown to be critically involved in regulating PAI-1 expression (Kietzmann et al., "Regulation of the Hypoxia-dependent Plasminogen Activator Inhibitor 1 Expression by MAP Kinases," *Thromb. Haemost.* 89:666-73 (2003); Norata et al., "Oxidised-HDL3 Induces the Expression of PAI-1 in Human Endothelial Cells. Role of p38MAPK Activation and mRNA Stabilization," *Br. J. Haematol.* 127:97-104 (2004), each of which is hereby incorporated by reference in its entirety). Thus, whether MKK3-p38 MAPK signaling is required for *S. pneumoniae*-induced PAI-1 expression was investigated.

Whether *S. pneumoniae* induces activation of MKK3 and p38 was initially examined. As shown in FIG. 14A, *S. pneumoniae* WT and purified PLY, but not *S. pneumoniae* Ply MT ("PLN"), induced potent phosphorylation of both p38 and MKK3 in A549 cells.

To determine whether the MKK3-p38 signaling pathway is involved in *S. pneumoniae*-induced PAI-1 expression, the effects of perturbing MKK3-p38 signaling on PAI-1 expression was assessed using various approaches. As shown in FIG. 14B, treatment with SB203580, a specific inhibitor of p38, and overexpressing dominant-negative mutant forms of p38α, p38β, and MKK3, greatly reduced *S. pneumoniae*-induced PAI-1 expression in A549 cells. In addition, SB203580 also inhibited PAI-1 induction by *S. pneumoniae* WT and PLY in BEAS-2B, SAEC, and NHBE cells.

Next, the requirement of MKK3 in PAI-1 expression was confirmed using Mkk3-deficient mice (Lu et al., "Defective IL-12 Production in Mitogen-activated Protein (MAP) Kinase Kinase 3 (Mkk3)-deficient Mice," *EMBO J.* 18:1845-57 (1999), which is hereby incorporated by reference in its entirety). As shown in FIG. 14C, *S. pneumoniae*-induced PAI-1 expression was greatly reduced in Mkk3⁻/⁻ mouse lung as compared with that in wild type mouse lung. These data suggest that MKK3-p38 signaling is required for *S. pneumoniae*-induced PAI-1 expression in lung.

To determine whether Mkk3-deficiency also potentiates ALI and reduces survival rate, wild type and Mkk3⁻/⁻ mice were first intratracheally inoculated with live *S. pneumoniae*, *S. pneumoniae* WT, Ply MT lysate, and PLY, and viability was assessed for 5 days after inoculation. As shown in FIG. 14D, approximately 80% of the Mkk3⁻/⁻ mice inoculated with live *S. pneumoniae* died within 48 hours and 100% died within 72 hours. By contrast, only approximately 25% of the inoculated wild type mice died within 48 hours and 66% died within 72 hours. Interestingly, PLY-inoculated Mkk3⁻/⁻ mice started to die within a few hours after inoculation and 100% of these inoculated mice died within 6 hours, as shown in FIG. 14E. Similar results were also observed in Mkk3⁻/⁻ mice inoculated with *S. pneumoniae* WT lysate, but not with *S. pneumoniae* Ply MT lysate, as shown in FIG. 14F. Consistent with these findings, histological analysis showed that lungs from the Mkk3⁻/⁻ mice exhibited more massive alveolar hemorrhage after *S. pneumoniae* and PLY inoculation than did lungs from the wild type mice, as shown in FIG. 14G. Together, these data suggest that MKK3-p38 signaling is indeed required for *S. pneumoniae*-induced PAI-1 expression in vitro and in vivo.

Example 19

CYLD Acts as a Negative Regulator for PAI-1 Expression Via Negative Cross-Talk with the *S. Pneumoniae*-Induced Mkk3-p38 MAPK Signaling Pathway It was next sought to determine whether CYLD deficiency leads to enhancement of PAI-1 expression and protects against lethality via negative cross-talk with p38 MAPK.

Whether MKK3-p38 activity is higher in Cyld⁻/⁻ cells was first determined. As shown in FIG. 15A, activation of both MKK3 and p38 by *S. pneumoniae* appears to be more potent in Cyld⁻/⁻ MEF than activation in wild type MEF. Similar results were also observed in Cyld⁻/⁻ cells treated with PLY.

The effect of perturbing p38 signaling on PAI-1 expression was then assessed in Cyld⁻/⁻ cells treated with or without *S. pneumoniae* and PLY. As shown in FIGS. 15B-C, pretreatment with SB203580 reduced PAI-1 expression in Cyld⁻/⁻ cells treated with *S. pneumoniae* (FIG. 15B) or PLY (FIG. 15C). These data suggest that CYLD acts as a negative regulator for *S. pneumoniae*-induced PAI-1 expression via negative cross-talk with the MKK3-p38 MAPK signaling pathway.

To further determine whether CYLD deficiency indeed protects mice from *S. pneumoniae*-induced lethality via enhancement of p38 MAPK activity, the effect of perturbing p38 signaling on the survival rate of Cyld⁻/⁻ mice inoculated with *S. pneumoniae* was evaluated. As shown in FIG. 15D, SB203580-pretreated Cyld⁻/⁻ mice started to die 12 hours after inoculation and approximately 80% of the inoculated mice died within 48 hours (20% survival). By contrast, SB203580-non-pretreated Cyld⁻/⁻ mice inoculated with *S. pneumoniae* didn't start to die until 48 hours after inoculation and only 13% of the inoculated mice died by the end of the experiment (87% survival). Taken together, these data indicate that CYLD plays a crucial role in negatively regulating MKK3-p38 MAPK-dependent expression of PAI-1, thus potentiating ALI and *S. pneumoniae*-induced lethality.

Example 20

Administration of rPAI-1 Reduces Lung Hemorrhage and Mortality in *S. pneumoniae* Infections Despite being known as a hallmark of the initial phase of S.p.-induced pneumonia, the molecular basis underlying lung hemorrhage during lethal S.p. infections has remained largely unknown. Whether PAI-1 plays a critical role in preventing lung hemorrhage and lethality was investigated by evaluating the effect of exogenous PAI-1 on S.p.-induced lethality as well as lung hemorrhage in wild type mice.

The efficacy of intratracheal administration of rPAI-1 was evaluated by assessing the presence and function of recombinant PAI-1 in mice. It was first determined whether exogenous PAI-1 is evenly distributed in the lungs of mice after intratracheal inoculation of recombinant stable PAI-1. Recombinant stable wild-type PAI-1 was first labeled with fluorescent dyes using an Alexa Flour 488 protein-labeling kit (Molecular Probes, Eugene, Oreg.) (Herbein & Wright, "Enhanced Clearance of Surfactant Protein D During LPS-induced Acute Inflammation in Rat Lung," *Am. J. Physiol. Lung Cell. Mol. Physiol.* 281:L268-L277 (2001), which is hereby incorporated by reference in its entirety). Alexa dyes were selected because their magnitude of fluorescence is constant from pH 4 to 10 and they have a low level of photobleaching compared with similar fluorescent dyes used for protein labeling. To determine the distribution of exogenously inoculated rPAI-1 in mice lung tissues, fluorescently labeled rPAI-1 (0.6 mg/kg) was suspended in 50 µl of sterile physiological saline and intratracheally inoculated into wild-type mouse lung (Arndt et al., "Regulation of Lipopolysaccharide-induced Lung Inflammation by Plasminogen Activator Inhibitor-1 Through a JNK-mediated Pathway," *J. Immunol.* 175:4049-59 (2005), which is hereby incorporated by reference in its entirety). Mice were sacrificed 6, 12, 24, 36, or 48 hours after inoculation of rPAI-1, the lung tissues were embedded with OCT and snap frozen in liquid nitrogen, and then histological analysis was performed.

A rapid and great increase in total and active PAI-1 was observed in BALF 6 hours after inoculation, remained sustained thereafter, and still remained above the control level even 48 hours after inoculation as shown in FIG. 16A. Thus, these data demonstrate that the intratracheally inoculated rPAI-1 is not only present but also functional and widely distributed in the lungs of mice after inoculation in the relevant setting.

To determine whether the exogenously inoculated rPAI-1 is also functional, the in vivo functional activity of intratracheally inoculated rPAI-1 was measured in lungs of mice using ELISA kits from Molecular Innovations. Recombinant stable wild-type PAI-1 (0.6 mg/kg) was first intratracheally inoculated into wild-type mouse lung (Arndt et al., "Regulation of Lipopolysaccharide-induced Lung Inflammation by Plasminogen Activator Inhibitor-1 Through a JNK-mediated Pathway," *J. Immunol.* 175:4049-59 (2005), which is hereby incorporated by reference in its entirety), and mice were sacrificed 6, 12, 24, 36, or 48 hours after inoculation of rPAI-1 to collect bronchoalveolar lavage fluid ("BALF"). Next, BALF was recovered from the distal trachea according to standard procedures using 2 aliquots of 800 µl of cold PBS (Glaab et al., "Tidal Midexpiratory Flow as a Measure of Airway Hyperresponsiveness in Allergic Mice," *Am. J. Physiol. Lung Cell. Mol. Physiol.* 280:L565-L573 (2001), which is hereby incorporated by reference in its entirety). The lavage was centrifuged and the supernatant was frozen in liquid nitrogen and stored at −70° C. prior to analysis. Determination of total and active PAI-1 levels in BALF was performed using ELISA kits from Molecular Innovations, with assays performed per the manufacturer's protocol.

Intratracheal inoculation with recombinant PAI-1 protected mice from S.p.-induced lethality. Consistent with this finding, S.p.-induced lung hemorrhage was also prevented in mice inoculated with rPAI-1 as assessed by performing pathological and histological analysis. Moreover, activity of exogenous PAI-1 was limited to the lung and was not found in the blood, as shown in FIG. 16B. Collectively, these data demonstrate that PAI-1 indeed plays a critical role in preventing excessive hemorrhage and lethality in lethal S.p. infections, and that intratracheal administration of rPAI-1 represents a novel therapeutic strategy for reducing lung hemorrhage and mortality rate in these infections.

Discussion of Examples 1-20

Examples 1-16 show that tumor suppressor CYLD deficiency protects mice from *S. pneumoniae* PLY-induced acute lung injury ("ALI"), bacterial translocation, and lethality, thus acting as a negative regulator for host survival in lethal *S. pneumoniae* infections. The present data demonstrate that CYLD, highly induced by *S. pneumoniae*, negatively regulates MKK3-p38 MAPK-dependent PAI-1 expression in lung, which in turn leads to enhanced ALI, severe hemorrhage, and increased mortality, as shown in FIG. 1. Notably, CYLD actually acts as a negative regulator for host defense against lethal bacterial infections CYLD was originally identified as a deubiquitinase, loss of which causes a benign human syndrome called cylindromatosis (Bignell et al. "Identification of the Familial Cylindromatosis Tumour-suppressor Gene," *Nat. Genet.* 25:160-5 (2000), which is hereby incorporated by reference in its entirety). Subsequent in vitro studies identified CYLD as a key negative regulator for NF-κB signaling (Brummelkamp et al., "Loss of the Cylindromatosis Tumour Suppressor Inhibits Apoptosis by Activating NF-κB," *Nature* 424:797-801 (2003); Kovalenko et al., "The Tumour Suppressor CYLD Negatively Regulates NF-κB Signaling by Deubiquitination," *Nature* 424:801-5 (2003); Trompouki et al., "CYLD Is a Deubiquitinating Enzyme That Negatively Regulates NF-κB Activation by TNFR Family Members," *Nature* 424:793-6 (2003), each of which is hereby incorporated by reference in its entirety). Interestingly, CYLD also acts as a negative regulator for p38 MAPK (Yoshida et al., "The Tumor Suppressor Cylindromatosis (CYLD) Acts as a Negative Regulator for Toll-like Receptor 2 Signaling via Negative Cross-talk with TRAF6 and TRAF7," *J. Biol. Chem.* 280:41111-21 (2005), which is hereby incorporated by reference in its entirety). It is likely that CYLD may also inhibit MKK3-p38 MAPK-dependent PAI-1 expression.

Despite the experimental evidence for the negative regulation of p38 by CYLD in vitro, the biological consequence of the negative cross-talk between CYLD and p38 MAPK was unknown. The present Examples show for the first time that inhibition of p38 by CYLD leads to reduced expression of PAI-1 in lung, and contributes significantly to ALI and an increased mortality rate in lethal *S. pneumoniae* infections. Given the complex regulatory mechanisms of ALI during bacterial infections (Chapman et al., "Developmental Expression of Plasminogen Activator Inhibitor Type 1 by Human Alveolar Macrophages. Possible Role in Lung Injury," *J. Immunol.* 145:3398-405 (1990); Olman et al., "Changes in Procoagulant and Fibrinolytic Gene Expression During Bleomycin-induced Lung Injury in the Mouse," *J. Clin. Invest.* 96:1621-30 (1995); Prabhakaran et al., "Elevated Levels of Plasminogen Activator Inhibitor-1 in Pulmonary Edema Fluid Are Associated with Mortality in Acute Lung Injury," *Am. J. Physiol. Lung Cell. Mol. Physiol.* 285: L20-L28 (2003); Suffredini et al., "Promotion and Subsequent Inhibition of Plasminogen Activation after Administration of Intravenous Endotoxin to Normal Subjects," *N. Engl. J. Med.* 320:1165-72 (1989), each of which is hereby incorporated by reference in its entirety), other molecular mechanisms may be involved in this complicated pathological process. Taken together, the present Examples provide new insights into the biological role of CYLD in negatively regulating p38-dependent PAI-1 expression and potentiating ALI in lethal *S. pneumoniae* infections, thereby unveiling an unknown mechanism underlying the high early mortality of *S. pneumoniae* infections. This mechanism provides novel therapeutic strategies for reducing high early mortality in lethal *S. pneumoniae* infections.

Despite the widespread use of antibiotics, mortality during the first several days of pneumococcal pneumonia has not decreased appreciably over the past 30 years. The early mortality rate from *S. pneumoniae* pneumonia is highest in the first 48 hours of hospitalization and remains unchanged from the pre-antibiotic era (Austrian & Gold, "Pneumococcal Bacteremia with Especial Reference to Bacteremic Pneumococcal Pneumonia," *Ann. Intern. Med.* 60:759-76 (1964); Kramer et al., "Pneumococcal Bacteremia—No Change in Mortality in 30 Years: Analysis of 104 Cases and Review of the Literature," *Isr. J. Med. Sci.* 23:174-80 (1987), each of which is hereby incorporated by reference in its entirety). Moreover, Austrian & Gold ("Pneumococcal Bacteremia with Especial Reference to Bacteremic Pneumococcal Pneumonia," *Ann. Intern. Med.* 60:759-76 (1964), which is hereby incorporated by reference in its entirety), demonstrated that patients who died during the first few days after diagnosis were generally not protected by treatment with antibiotics. The earliest stage of infection is seldom recognized and is most likely to be found in patients who die after illness lasting for a very short time period, because the disease progresses very rapidly in some of the infected patients. The molecular mechanism underlying this early higher mortality in pneumococcal pneumonia, however, was unknown.

In addition, many animal models of pneumococcal pneumonia have provided insights into critical aspects of pathogenesis but have focused on death during the later stage of infection, which is characterized by extensive PMNs recruitment. These models are very useful for antimicrobial studies and for evaluating pneumonia pathogenesis, but they provide less information concerning host defense or pathological changes in the early stage of infection (Dockrell et al., "Alveolar Macrophage Apoptosis Contributes to Pneumococcal Clearance in a Resolving Model of Pulmonary Infection," *J. Immunol.* 171:5380-8 (2003), which is hereby incorporated by reference in its entirety). The present Examples present clear evidence for the establishment of a mouse model of higher death during the early stage of lethal pneumococcal pneumonia. Moreover, the Examples show that pneumolysin plays a critical role in inducing ALI and death in the earlier stage of severe infection. The present Examples thus bring novel insights into the molecular mechanism underlying this early higher mortality in pneumoccal pneumonia and provide novel therapeutic strategies for reducing the early mortality rate in lethal pneumococcal pneumonia.

In addition, Examples 17-20 demonstrate the protective role of PAI-1 in reducing the early mortality rate in lethal pneumococcal pneumonia. PAI-1 is a very complex protein that is tightly regulated at the transcriptional level, and its role in bacterial infections still remains largely unknown. Here, a mouse model of PLY-induced ALI and lethality was used to investigate the role of PAI-1 in severe pneumococcal pneumonia. Endogenous PAI-1 was found to be up-regulated at the levels of both mRNA and protein in the lungs of wild type mice inoculated with *S. pneumoniae*, as shown in FIGS. 8A-H, 10A-C, and 11A-L. Further, enhanced lung injury and alveolar hemorrhage was observed, as well as a reduced survival rate in PAI-1$^{-/-}$ mice, thereby demonstrating the protective role of endogenous PAI-1 during pneumococcal pneumonia. Moreover, intratracheal administration of exogenous rPAI-1 was shown to prevent tissue injury and to reduce the mortality rate, as shown in FIGS. 8A-H.

The present Examples provide direct evidence for the first time of the protective role of PAI-1 during severe pneumococcal pneumonia in vivo. These findings are in line with a report showing that PAI-1$^{-/-}$ mice are more susceptible to Gram-negative bacterial infection (Renckens et al., "Plasminogen Activator Inhibitor Type 1 Is Protective During Severe Gram-negative Pneumonia," *Blood* 109:1593-1601 (2007), which is hereby incorporated by reference in its entirety). In addition to its role in reducing lung injury, PAI-1 was also shown to prevent bacterial translocation from lung into blood circulation. Considering the present data, it is evident that PAI-1 plays a critical role in reducing the mortality rate during the early stage of severe pneumococcal pneumonia, not only by preventing tissue damage but also by reducing bacterial translocation into systemic circulation. Administration of exogenous PAI-1 should help to reduce high early mortality in otherwise lethal pneumococcal pneumonia.

Example 21

TLR4-MyD88 Signaling Is Required for *S. Pneumoniae* Pneumolysin-Induced PAI-1 Expression It was next sought to determine which host surface receptors are involved in mediating PAI-1 induction by pneumolysin.

In review of the surface receptors involved in interacting with bacteria, human Toll-like receptors ("TLRs") have been shown recently to play a critical role in the recognition of various bacterial components (Kopp & Medzhitov, "Recognition of Microbial Infection by Toll-like Receptors," *Curr. Opin. Immunol.* 15:396-401 (2003); Kawai & Akira, "TLR Signaling," *Cell Death Differ.* 13:816-25 (2006), each of which is hereby incorporated by reference in its entirety). To date, at least 11 mammalian TLRs have been reported (Kopp & Medzhitov, "Recognition of Microbial Infection by Toll-like Receptors," *Curr. Opin. Immunol.* 15:396-401 (2003); Kawai & Akira, "TLR Signaling," *Cell Death Differ.* 13:816-25 (2006); Lauw et al., "Of Mice and Man: TLR11 (Finally) Finds Profilin," *Trends Immunol.* 26:509-11 (2005), each of which is hereby incorporated by reference in its entirety). TLR2 and TLR4, and their immediate downstream signaling transducer MyD88, play an important role in the pathogenesis of *S. pneumoniae* infections. TLR4 has also been shown to be the receptor for PLY (Srivastava et al., "The Apoptotic Response to Pneumolysin Is Toll-like Receptor 4 Dependent and Protects Against Pneumococcal Disease," *Infect. Immun.* 73:6479-87 (2005), which is hereby incorporated by reference in its entirety), and TLR4 is reportedly required for pneumolysin-induced IL-6 expression (Malley et al., "Recognition of Pneumolysin by Toll-like Receptor 4 Confers Resistance to Pneumococcal Infection," *Proc. Nat'l Acad. Sci. USA* 100:1966-71 (2003), which is hereby incorporated by reference in its entirety). Therefore, it was next sought to determine whether TLR2 and/or TLR4 is also involved in *S. pneumoniae* PLY-induced PAI-1 expression.

Overexpressing a dominant-negative mutant of TLR4 and MyD88 inhibited both *S. pneumoniae*- and PLY-induced PAI-1 expression in A549 cells, as shown in FIG. 17A, suggesting that TLR4-MyD88 signaling is required for PLY-induced PAI-1 expression. PAI-1 induction was not perturbed by TLR2 signaling. The requirement for TLR4 signaling in PLY-induced PAI-1 mRNA expression was further confirmed in vivo using TLR4-deficient mice. As shown in FIG. 17B, PLY-induced PAI-1 expression was much lower in the lungs of Tlr4$^{-/-}$ mice than that in wild type mice.

To further determine whether exogenous rPAI-1 also reduces mortality rate in Tlr4$^{-/-}$ mice, Tlr4$^{-/-}$ mice were intratracheally inoculated with PLY with or without mouse rPAI-1 pre-administration, and viability was assessed. As shown in FIG. 17C, rPAI-1 inoculation fully protected mice from lethal challenge. Together, these data suggest that TLR4-MyD88 signaling is indeed required for PLY-induced PAI-1 expression in vitro and in vivo.

Example 22

TLR4-MyD88-TRAF6/7 Signaling Cascade is Crucial for PAI-1 Induction by *S. Pneumoniae*

The signaling cascade immediately downstream of TLR4 was next investigated.

The adaptor molecule MyD88 appears to be the first molecule recruited to the TLR receptor complex, which in turn promotes association with the interleukin-1 receptor-associated kinase ("IRAK") (Kopp & Medzhitov, "Recognition of Microbial Infection by Toll-like Receptors," *Curr. Opin. Immunol.* 15:396-401 (2003); Kawai & Akira, "TLR Signaling," *Cell Death Differ.* 13:816-25 (2006); Fitzgerald et al., "Endotoxin Recognition and Signal Transduction by the TLR4/MD2-complex," *Microbes Infect.* 6:1361-7 (2004), each of which is hereby incorporated by reference in its entirety) and then the interaction of tumor necrosis factor receptor-associated factor 6 ("TRAF6") with the receptor complex. Once the MyD88-IRAK-TRAF6 complex is formed, the IRAK-TRAF6 disengages from the receptor complex and further interacts with the downstream signaling pathways, including MAPK and NF-κB signaling pathways.

To determine the involvement of the MyD88-TRAF signaling cascade in PAI-1 induction, the effects of perturbing their signaling on PAI-1 induction was assessed. It was then determined whether CYLD negatively regulates MKK3-p38-dependent PAI-1 expression via inhibiting their further upstream signaling transducer TRAFs. As shown in FIG. 18A-C, perturbing the signaling of TRAF6 and TRAF7, but not TRAF2, inhibited S.p.-induced PAI-1 expression in CYLD-deficient cells. Moreover, CYLD physically interacts and co-localizes with TRAF6 and TRAF7. Overexpression of WT CYLD reduced, whereas siRNA knock-down of CYLD enhanced, the ubiquitination of TRAF6 and TRAF7. These data demonstrate that CYLD inhibits MKK3-p38-dependent PAI-1 expression likely by deubiquitinating TRAF6 and TRAF7 (see also FIGS. 14A-C).

Example 23

CYLD Deficiency Protects Cyld$^{-/-}$ Mice from Lethality in *S. Pneumoniae* Infections Independently of the NF-κB Pathway Since S.p. induces an inflammatory response via a NF-κB-dependent mechanism and CYLD is known as a negative regulator for NF-κB (Brummelkamp et al., "Loss of the Cylindromatosis Tumour Suppressor Inhibits Apoptosis by Activating NF-κB," *Nature* 424:797-801 (2003); Kovalenko et al., "The Tumour Suppressor CYLD Negatively Regulates NF-κB Signalling by Deubiquitination," *Nature* 424:801-5 (2003); Trompouki et al., "CYLD Is a Deubiquitinating Enzyme That Negatively Regulates NF-κB Activation by TNFR Family Members," *Nature* 424:793-6 (2003); Kadioglu & Andrew, "The Innate Immune Response to Pneumococcal Lung Infection: The Untold Story," *Trends Immunol.* 25:143-9 (2004), each of which is hereby incorporated by reference in its entirety), whether CYLD deficiency protects Cyld$^{-/-}$ mice from lung hemorrhage and lethality in S.p. infections via a NF-κB-dependent mechanism was determined.

As shown in FIGS. 19A-C, perturbing inhibitor of KB kinase ("IKK") signaling using wedelolactone did not greatly alter the survival rate of Cyld$^{-/-}$ mice inoculated with S.p. Moreover, perturbing IKKβ-IκBα signaling did not block S.p.-induced PAI-1 expression in A549 cells. Thus, it appears that CYLD deficiency protects Cyld$^{-/-}$ mice from lethality in S.p. infections independently of the NF-κB pathway.

Example 24

Cytolytic Activity of Pneumolysin is a Critical Factor of Pneumolysin-Induced Early Lethality in Severe *S. Pneumoniae* Infection To determine whether the cytolytic effect of PLY is involved in PLY-induced early lethality, mice were inoculated (10 mice for each inoculation) with cytolytic activity-deficient mutant PLY ("PdT"), a control, or WT PLY. The early lethality caused by PdT was compared to WT and control ("CON"). As shown in FIG. 20, all mice inoculated with PdT survived (100% survival), suggesting that the cytolytic effect of PLY is crucial for PLY-induced early lethality.

Pneumolysin is a member of a family of cholesterol-binding toxins (CBTs, known as cholesterol-dependent cytolysin), which also includes numerous toxins from four genera of Gram-positive bacteria (perfringolysin from *Clostridium perforingens*, listeriolysin from *Listerio monocytogenes*, streptolysin from *Streptococcus pyogenes*, and anthrolysin from *Bacillus anthraxis*). These toxins share similar mechanisms of action for the cytolytic toxins, and therefore it is expected that the CYLD antagonist and/or PAI-1 will similarly be useful in treating or preventing hemorrhage caused by these and other cholesterol-dependent cytolysins.

Example 25

Alveolar Hemorrhage is a Hallmark of Severe *S. pneumoniae* Infection at the Early Stage Although a mouse model was used to study severe S.p. infection, the findings from the mouse model are completely in line with the typical pathological changes of pneumococcal lobar pneumonia at the early stage not only in other animal (e.g. rat) models but also in human patients.

Histologically, during the initial stage of invasion, the affected human lung is fully filled with red blood cells and fibrin but few polymorphonuclear neutrophils ("PMNs"). This stage, though seldom recognized, was well described by Loeschcke (*Beitr. Path. Anat.* 86:201 (1931), which is hereby incorporated by reference in its entirety) and is often found in patients who died within a short time period after the onset of the disease. Indeed, as shown in FIG. 21A, histological analysis of lungs of PLY-inoculated WT mice showed marked alveolar damage and hemorrhage but few PMN cells. PMN cell counts from lungs of S.p. lysate-inoculated mice also indicate that no significant increase of PMN cell migration into alveolar spaces was found 6 hours after intratracheal inoculation in severe S.p. infection, as shown in FIG. 21B.

Next, extravasation of red blood cells ("RBCs") from lungs of S.p. WT- or Ply MT-inoculated mice was measured (Asti et al., "Lipopolysaccharide Induced Lung Injury in Mice. I. Concomitant Evaluation of Inflammatory Cells and Haemorrhagic Lung Damage," *Pulm. Pharmacol. Ther.* 13:61-9 (2000), which is hereby incorporated by reference in its entirety). As shown in FIG. 21C, extravasation of RBCs into airspace was significantly induced by intratracheal inoculation of WT lysate (1352.44±192.20%), but not by Ply MT lysate (109.88±12.38%). In contrast to severe alveolar damage and hemorrhage, expression of inflammatory cytokines was not significantly changed in S.p. lysate- or PLY-inoculated mice in severe infections.

Example 26

*Haemophilus influenza* Infection Leads to Upregulation of CYLD

Based in part on the results presented in Examples 16, 17, 19, 22, and 23 showing that CYLD upregulation is implicated in *S. pneumoniae* infections, the role of CYLD in lung infection by other pathogens was assessed using nontypeable *Haemophilus influenzae* ("NTHi").

A clinical isolate of NTHi wild-type strain 12 was used in in vivo animal experiments (Shuto et al., "Activation of NF-κB by Nontypeable *Hemophilus influenzae* Is Mediated by Toll-like Receptor 2-TAK1-dependent NIK-IKK α/β-I κB α and MKK3/6-p38 MAP Kinase Signaling Pathways in Epithelial Cells," Proc. Nat'l Acad. Sci. USA 98:8774-9 (2001), which is hereby incorporated by reference in its entirety). Bacteria was grown on chocolate agar at 37° C. in an atmosphere of 5% $CO_2$ for overnight and inoculated in brain heart infusion broth supplemented with 3.5 μg of NAD per ml (BHI). After overnight incubation, bacteria were subcultured into 5 ml of fresh BHI and the log phase NTHi, which was monitored by measurement of optical density value, was washed and suspended in isotonic saline. NTHi was inoculated into the lung (for pneumonia model) at a concentration of $5 \times 10^7$ CFU.

For a NTHi-induced pneumonia model in WT and Cyld$^{-/-}$ mice, anaesthetized mice were intratracheally inoculated with $5 \times 10^7$ CFU of NTHi, and saline was inoculated as control. The inoculated mice were then sacrificed by intraperitoneal inoculation of 100 mg/kg sodium pentobarbital at 3, 6, 9, 24, 72, and 168 hours after inoculation of NTHi. For histological analysis, dissected lung was inflated and fixed with 10% buffered formaldehyde, embedded in paraffin, and sectioned at 5-μM thickness. Sections were then stained and inspected as described above. To assess the mRNA expression of inflammatory mediators, total RNA was extracted from the NTHi- and saline-inoculated lungs at the time points indicated above and Q-PCR was performed as described previously (Yoshida et al., "The Tumor Suppressor Cylindromatosis (CYLD) Acts as a Negative Regulator for Toll-like Receptor 2 Signaling via Negative Cross-talk with TRAF6 AND TRAF7," *J. Biol. Chem.* 280: 41111-21 (2005), which is hereby incorporated by reference in its entirety). All animal experiments were approved by the Institutional Animal Care and Use Committee at University of Rochester.

It was hypothesized that CYLD is induced by NTHi and increased CYLD expression will in turn lead to inhibition of NTHi-induced inflammatory response, thereby preventing overactive inflammatory response that is detrimental to the host. This hypothesis was tested by first evaluating the effect of NTHi on CYLD expression. As shown in FIGS. 22A-B, marked induction of CYLD by NTHi was observed in the lungs of NTHi-inoculated WT mice along with down-regulation of pro-inflammatory mediators IL-1β and MIP-2. The peak of CYLD induction was clearly preceded by the peak of the induction of IL-1β and MIP-2, thereby suggesting that NTHi-induced CYLD is responsible for down-regulation of inflammatory response.

In age- and sex-matched WT and Cyld$^{-/-}$ mice inoculated with NTHi, the inflammatory response in the lung of infected mice was monitored for up to 7 days. Histological evaluation of the lung of NTHi-inoculated mice showed enhanced leukocyte infiltration in peribroncheal and interstitial area in Cyld$^{-/-}$ mice compared with WT mice, as shown in FIG. 22C, confirming that CYLD is responsible for negative regulation of the inflammatory response. Additional experiments demonstrated that the NTHi inflammatory response was induced through TLR2-MyD88-TRAF6/7-NF-κB signaling pathway and, further, that CYLD inhibition of this inflammatory response was achieved via deubiquitinating TRAF6 and TRAF7. These results are consistent with the results reported in Examples 1-25, and it is believed that CYLD upregulation is a common occurrence during pathogen infection. We have found that CYLD expression is up-regulated not only by *S. pneumoniae* and NTHi, but also by bacterial agonists for TLR2 including peptidoglycan, MALP-2, and Pam3CSK4.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

---

What is claimed:

1. A method for treatment of a hemorrhagic lung condition in a patient comprising:
 administering to a lung of a patient having a pathogen-induced hemorrhagic lung condition an amount of plasminogen activator inhibitor-1 ("PAI-1") under conditions effective to treat the hemorrhagic lung condition in the patient.

2. The method according to claim 1, wherein PAI-1 is recombinant human PAI-1.

3. The method according to claim 1, wherein said administering is carried out via intratracheal inoculation, via aspiration, via airway instillation, intranasally, via aerosolization, or via nebulization.

4. The method according to claim 1, wherein said administering further comprises administering an inhibitor of a cholesterol-dependent cytolysin.

5. The method according to claim 1, wherein the PAI-1 is present in a pharmaceutical formulation.

6. The method according to claim 5, wherein the pharmaceutical formulation is a surfactant formulation, a liquid formulation suitable for aspiration, aerosolization or nebulization, or a powder formulation for nebulization.

7. The method according to claim 5, wherein the pharmaceutical formulation further comprises an antibiotic.

8. The method according to claim 1, wherein the pathogen is a virus, a Gram negative bacteria, a Gram positive bacteria, an atypical bacteria, a fungus, or a parasite.

9. The method according to claim 1, wherein the pathogen-induced hemorrhagic lung condition is associated with acute bronchitis, severe pneumonia, aspergilloma, tuberculosis, bronchiectasis, coccidiodomycosis, toxoplasmosis, or listeriosis.

10. The method according to claim 1, wherein the patient is a mammal.

11. A method for treatment of a hemorrhagic lung condition in a patient comprising:
 administering to a lung of a patient having a pathogen-induced hemorrhagic lung condition an effective amount of a therapeutic agent consisting of plasminogen activator inhibitor-1 ("PAI-1") alone or in combination with one or more of an inhibitor of a cholesterol-dependent cytolysin, an antibiotic agent, or an inhibitor of CYLD, wherein said administering is effective to treat the hemorrhagic lung condition in the patient.

12. The method according to claim 11, wherein PAI-1 is administered alone.

13. The method according to claim 11, wherein PAI-1 is administered in combination with an antibiotic agent.

14. The method according to claim 11, wherein PAI-1 is administered in combination with an inhibitor of a cholesterol-dependent cytolysin.

15. The method according to claim 11, wherein PAI-1 is recombinant human PAI-1.

16. The method according to claim 11, wherein the therapeutic agent is present in a formulation suitable for said administering via intratracheal inoculation, via aspiration, via airway instillation, intranasally, via aerosolization, or via nebulization.

17. The method according to claim 16, wherein the formulation is a surfactant formulation, a liquid formulation suitable for aspiration, aerosolization or nebulization, or a powder formulation for nebulization.

18. The method according to claim 11, wherein the pathogen is a virus, a Gram negative bacteria, a Gram positive bacteria, an atypical bacteria, a fungus, or a parasite.

19. The method according to claim 11, wherein the pathogen infection is associated with acute bronchitis, severe pneumonia, aspergilloma, tuberculosis, bronchiectasis, coccidiodomycosis, toxoplasmosis, or listeriosis.

20. The method according to claim 11, wherein the patient is a mammal.

21. The method according to claim 11 further comprising repeating said administering.

22. The method according to claim 11 wherein the method consists of said administering.

23. A method for treatment of *Streptococcus pneumonia* lung infection in a patient consisting of:
 administering to a lung of a patient having a *Streptococcus pneumonia* lung infection an effective amount of plasminogen activator inhibitor-1 ("PAI-1") alone or in combination with one or more of an inhibitor of a cholesterol-dependent cytolysin, an antibiotic agent, or an inhibitor of CYLD, wherein said administering is effective to treat the *Streptococcus pneumonia* lung infection in the patient.

24. The method according to claim 23, wherein PAI-1 is administered alone.

25. The method according to claim 23, wherein PAI-1 is administered in combination with an antibiotic agent.

26. The method according to claim 23, wherein PAI-1 is administered in combination with an inhibitor of a cholesterol-dependent cytolysin.

27. The method according to claim 23, wherein PAI-1 is recombinant human PAI-1.

28. The method according to claim 23, wherein the PAI-1 is present in a formulation suitable for said administering via intratracheal inoculation, via aspiration, via airway instillation, intranasally, via aerosolization, or via nebulization.

* * * * *

SEQUENCE LISTING

```
<160> NUMBER OF SEQ ID NOS: 16

<210> SEQ ID NO 1
<211> LENGTH: 21
<212> TYPE: RNA
<213> ORGANISM: artificial
<220> FEATURE:
<223> OTHER INFORMATION: anti-CYLD siRNA

<400> SEQUENCE: 1
aaguaccgaa gggaaguaua g                                          21

<210> SEQ ID NO 2
<211> LENGTH: 19
<212> TYPE: DNA
<213> ORGANISM: artificial
<220> FEATURE:
<223> OTHER INFORMATION: DNA encoding anti-CYLD siRNA
```

```
<400> SEQUENCE: 2
cgaagaggct gaatcataa                                              19

<210> SEQ ID NO 3
<211> LENGTH: 19
<212> TYPE: DNA
<213> ORGANISM: artificial
<220> FEATURE:
<223> OTHER INFORMATION: DNA encoding anti-CYLD siRNA

<400> SEQUENCE: 3
cgctgtaact ctttagcat                                              19

<210> SEQ ID NO 4
<211> LENGTH: 19
<212> TYPE: DNA
<213> ORGANISM: artificial
<220> FEATURE:
<223> OTHER INFORMATION: DNA encoding anti-CYLD siRNA

<400> SEQUENCE: 4
gaactcacat ggtctagaa                                              19

<210> SEQ ID NO 5
<211> LENGTH: 19
<212> TYPE: DNA
<213> ORGANISM: artificial
<220> FEATURE:
<223> OTHER INFORMATION: DNA encoding anti-CYLD siRNA

<400> SEQUENCE: 5
gcagagtcct aacgttgca                                              19

<210> SEQ ID NO 6
<211> LENGTH: 47
<212> TYPE: DNA
<213> ORGANISM: artificial
<220> FEATURE:
<223> OTHER INFORMATION: DNA encoding anti-CYLD shRNA

<400> SEQUENCE: 6
cctcatgcag ttctctttgt tcaagagaca aagagaactg catgagg                47

<210> SEQ ID NO 7
<211> LENGTH: 47
<212> TYPE: DNA
<213> ORGANISM: artificial
<220> FEATURE:
<223> OTHER INFORMATION: DNA encoding anti-CYLD shRNA

<400> SEQUENCE: 7
gaatgccgac ctacaaagat tcaagagatc tttgtaggtc ggcattc                47

<210> SEQ ID NO 8
<211> LENGTH: 47
<212> TYPE: DNA
<213> ORGANISM: artificial
<220> FEATURE:
<223> OTHER INFORMATION: DNA encoding anti-CYLD shRNA

<400> SEQUENCE: 8
cagttatatt ctgtgatgtt tcaagagaac atcacagaat ataactg                47

<210> SEQ ID NO 9
<211> LENGTH: 47
<212> TYPE: DNA
```

```
<213> ORGANISM: artificial
<220> FEATURE:
<223> OTHER INFORMATION: DNA encoding anti-CYLD shRNA

<400> SEQUENCE: 9
gaggtgttgg ggacaaaggt tcaagagacc tttgtcccca acacctc                    47

<210> SEQ ID NO 10
<211> LENGTH: 47
<212> TYPE: DNA
<213> ORGANISM: artificial
<220> FEATURE:
<223> OTHER INFORMATION: DNA encoding anti-CYLD shRNA

<400> SEQUENCE: 10
gtgggctcat tggctgaagt tcaagagact tcagccaatg agcccac                    47

<210> SEQ ID NO 11
<211> LENGTH: 22
<212> TYPE: DNA
<213> ORGANISM: artificial
<220> FEATURE:
<223> OTHER INFORMATION: Human PAI-1 forward primer

<400> SEQUENCE: 11
gttctatgag ggctgcgtct tt                                               22

<210> SEQ ID NO 12
<211> LENGTH: 19
<212> TYPE: DNA
<213> ORGANISM: artificial
<220> FEATURE:
<223> OTHER INFORMATION: Human PAI-1 reverse primer

<400> SEQUENCE: 12
ggctggagca caccacatc                                                   19

<210> SEQ ID NO 13
<211> LENGTH: 25
<212> TYPE: DNA
<213> ORGANISM: artificial
<220> FEATURE:
<223> OTHER INFORMATION: Mouse PAI-1 forward primer

<400> SEQUENCE: 13
aaagacacca gtagtcactc agcaa                                            25

<210> SEQ ID NO 14
<211> LENGTH: 22
<212> TYPE: DNA
<213> ORGANISM: artificial
<220> FEATURE:
<223> OTHER INFORMATION: Mouse PAI-1 reverse primer

<400> SEQUENCE: 14
ctgggaagtc agtgtcaaac ca                                               22

<210> SEQ ID NO 15
<211> LENGTH: 23
<212> TYPE: DNA
<213> ORGANISM: artificial
<220> FEATURE:
<223> OTHER INFORMATION: Mouse CYLD forward primer

<400> SEQUENCE: 15
ctcagcctat ttagaaacag act                                              23
```

```
<210> SEQ ID NO 16
<211> LENGTH: 19
<212> TYPE: DNA
<213> ORGANISM: artificial
<220> FEATURE:
<223> OTHER INFORMATION: Mouse CYLD reverse primer

<400> SEQUENCE: 16
tctcctgggc ctgcaaaat                                              19
```